US012668626B2

(12) United States Patent
Li et al.

(10) Patent No.: US 12,668,626 B2
(45) Date of Patent: Jun. 30, 2026

(54) ANTI-IL31 ANTIBODIES FOR VETERINARY USE

(71) Applicant: Elanco US Inc., Greenfield, IN (US)

(72) Inventors: Shyr Jiann Li, Millbrae, CA (US);
Lam Nguyen, Union City, CA (US);
Hangjun Zhan, Foster City, CA (US)

(73) Assignee: Elanco US Inc., Greenfield, IN (US)

( * ) Notice: Subject to any disclaimer, the term of this patent is extended or adjusted under 35 U.S.C. 154(b) by 1160 days.

(21) Appl. No.: 17/638,372

(22) PCT Filed: Aug. 28, 2020

(86) PCT No.: PCT/US2020/048618
§ 371 (c)(1),
(2) Date: Feb. 25, 2022

(87) PCT Pub. No.: WO2021/041972
PCT Pub. Date: Mar. 4, 2021

(65) Prior Publication Data
US 2022/0324960 A1      Oct. 13, 2022

Related U.S. Application Data

(60) Provisional application No. 62/894,526, filed on Aug. 30, 2019, provisional application No. 62/893,799, filed on Aug. 29, 2019.

(51) Int. Cl.
*A61K 39/395* (2006.01)
*C07K 16/24* (2006.01)

(52) U.S. Cl.
CPC ........ *C07K 16/244* (2013.01); *C07K 2317/24* (2013.01); *C07K 2317/565* (2013.01); *C07K 2317/92* (2013.01)

(58) Field of Classification Search
CPC .... C07K 2317/565; A61P 17/04; A61P 17/00; A61K 2039/505
See application file for complete search history.

(56) References Cited

U.S. PATENT DOCUMENTS

| | | | |
|---|---|---|---|
| 5,760,185 A | 6/1998 | Kimachi et al. | |
| 5,795,965 A | 8/1998 | Tsuchiya et al. | |
| 6,194,551 B1 | 2/2001 | Idusogie et al. | |
| 7,514,077 B2 | 4/2009 | Yao et al. | |
| 7,531,636 B2 | 5/2009 | Siadak et al. | |
| 7,531,637 B2 | 5/2009 | Siadak et al. | |
| 7,615,213 B2 | 11/2009 | Kasaian et al. | |
| 7,638,126 B2 | 12/2009 | Yao et al. | |
| 7,939,068 B2 | 5/2011 | Yao et al. | |
| 8,017,122 B2 | 9/2011 | Siadak et al. | |
| 8,101,183 B2 | 1/2012 | Siadak et al. | |
| 8,105,590 B2 | 1/2012 | Yao et al. | |
| 8,133,899 B2 | 3/2012 | Milton-Fry et al. | |
| 8,377,438 B2 | 2/2013 | Yao et al. | |
| 8,388,964 B2 | 3/2013 | Leung et al. | |

| | | |
|---|---|---|
| 8,460,667 B2 | 6/2013 | Blanc et al. |
| 8,466,262 B2 | 6/2013 | Siadak et al. |
| 8,470,979 B2 | 6/2013 | Bondeensgaard et al. |
| 8,568,723 B2 | 10/2013 | Siadak et al. |
| 8,637,015 B2 | 1/2014 | Yao et al. |
| 8,790,651 B2 | 7/2014 | Bammert et al. |
| 8,968,732 B2 | 3/2015 | Yao et al. |
| 9,156,909 B2 | 10/2015 | Siadak et al. |
| 9,206,253 B2 | 12/2015 | Bammert et al. |
| 9,328,164 B2 | 5/2016 | Gearing |
| 9,409,986 B2 | 8/2016 | Wu et al. |
| 9,447,183 B2 | 9/2016 | Wu et al. |
| 9,447,184 B2 | 9/2016 | Wu et al. |
| 9,512,219 B2 | 12/2016 | Siadak et al. |
| 9,556,280 B2 | 1/2017 | Murphy et al. |
| 9,592,293 B2 | 3/2017 | Wu et al. |
| 9,605,062 B2 | 3/2017 | Sprecher et al. |
| 9,683,037 B2 | 6/2017 | Siadak et al. |
| 9,822,177 B2 | 11/2017 | Siadak et al. |
| 10,011,647 B2 | 7/2018 | Murphy et al. |
| 10,086,076 B2 | 10/2018 | Wu et al. |
| 10,093,731 B2 | 10/2018 | Li et al. |
| 10,150,810 B2 | 12/2018 | Li et al. |
| 10,259,868 B2 | 4/2019 | Siadak et al. |
| 10,273,297 B2 | 4/2019 | Siadak et al. |
| 10,633,449 B2 | 4/2020 | Shih et al. |
| 10,669,337 B2 | 6/2020 | Irving et al. |
| 10,815,305 B2 | 10/2020 | Orengo et al. |
| 10,836,796 B2 | 11/2020 | Zhao et al. |
| 10,845,365 B2 | 11/2020 | Datta et al. |
| 12,435,132 B2 | 10/2025 | Li |
| 12,448,438 B2 | 10/2025 | Li |
| 2003/0224487 A1 | 12/2003 | Sprecher et al. |
| 2006/0073145 A1 | 4/2006 | Leturcq et al. |
| 2006/0141579 A1 | 6/2006 | Sprecher et al. |
| 2006/0182743 A1 | 8/2006 | Bilsborough |

(Continued)

FOREIGN PATENT DOCUMENTS

| | | |
|---|---|---|
| CN | 105722992 A | 6/2016 |
| EP | 1270595 A1 | 1/2003 |

(Continued)

OTHER PUBLICATIONS

Tominaga et al., "In Vitro Model for Penetration of Sensory Nerve Fibers on a Matrigel Basement Membrane: Implication for Possible Application to Intractable Pruritus," British Journal of Dermatology, 2009, 161:1028-1037.

(Continued)

*Primary Examiner* — Dong Jiang
(74) *Attorney, Agent, or Firm* — McBee Moore & Vanik IP, LLC

(57) ABSTRACT

Provided are various embodiments relating to anti-IL31 antibodies having enhanced binding to canine IL31 and feline IL31. Such antibodies can be used in methods to treat IL31-induced conditions in companion animals, such as canines and felines. Antibodies with enhanced binding to canine IL31 and feline IL31 are provided. Antibody heavy chains and light chains that are capable of forming antibodies that bind canine and feline IL31 are also provided.

20 Claims, 1 Drawing Sheet
Specification includes a Sequence Listing.

(56) References Cited

U.S. PATENT DOCUMENTS

| | | |
|---|---|---|
| 2006/0228329 A1 | 10/2006 | Brady et al. |
| 2006/0275296 A1 | 12/2006 | Siadak et al. |
| 2007/0160610 A1 | 7/2007 | Yao et al. |
| 2007/0160611 A1 | 7/2007 | Yao et al. |
| 2008/0260686 A1 | 10/2008 | Bilsborough et al. |
| 2009/0110685 A1 | 4/2009 | Patel et al. |
| 2009/0208494 A1 | 8/2009 | Bondensgaard et al. |
| 2009/0220417 A1 | 9/2009 | Siadak et al. |
| 2009/0252732 A1 | 10/2009 | Siadak et al. |
| 2009/0280121 A1 | 11/2009 | Leung et al. |
| 2009/0300776 A1 | 12/2009 | Lecron et al. |
| 2010/0061988 A1 | 3/2010 | Hansen |
| 2010/0075996 A1 | 3/2010 | Milton-Fry et al. |
| 2010/0221244 A1 | 9/2010 | Yao et al. |
| 2010/0297125 A1 | 11/2010 | Yao et al. |
| 2011/0002926 A1 | 1/2011 | Matthews |
| 2011/0008820 A1 | 1/2011 | Bilsborough et al. |
| 2011/0123440 A1 | 5/2011 | Hansen et al. |
| 2011/0165063 A1 | 7/2011 | Hsieh et al. |
| 2011/0177072 A1 | 7/2011 | Yao et al. |
| 2011/0287454 A1 | 11/2011 | Wagner |
| 2011/0318343 A1 | 12/2011 | Kaisheva et al. |
| 2012/0083456 A1 | 4/2012 | Bilsborough et al. |
| 2012/0100155 A1 | 4/2012 | Stoloff et al. |
| 2012/0107310 A1 | 5/2012 | Yao et al. |
| 2012/0275996 A1 | 11/2012 | Hsieh |
| 2013/0022616 A1 | 1/2013 | Bammert et al. |
| 2013/0177563 A1 | 7/2013 | Leung et al. |
| 2013/0216542 A1 | 8/2013 | Siadak et al. |
| 2013/0266562 A1 | 10/2013 | Siadak et al. |
| 2013/0295611 A1 | 11/2013 | Bondensgaard et al. |
| 2014/0271658 A1 | 9/2014 | Murphy et al. |
| 2014/0286958 A1 | 9/2014 | Bammert et al. |
| 2015/0004161 A1 | 1/2015 | Zhu et al. |
| 2015/0037331 A1 | 2/2015 | Siadak et al. |
| 2015/0368336 A1 | 12/2015 | Siadak et al. |
| 2016/0024201 A1 | 1/2016 | Leung et al. |
| 2016/0137739 A1 | 5/2016 | Amett et al. |
| 2016/0272703 A1 | 9/2016 | Hsieh et al. |
| 2016/0333101 A1 | 11/2016 | Zhou et al. |
| 2017/0058027 A1 | 3/2017 | Wu et al. |
| 2017/0096484 A1 | 4/2017 | Leung et al. |
| 2017/0158671 A1 | 6/2017 | Zhu et al. |
| 2017/0306019 A1 | 10/2017 | Carriere et al. |
| 2018/0066050 A1 | 3/2018 | Yao et al. |
| 2018/0079817 A1 | 3/2018 | Kaneko et al. |
| 2018/0155418 A1 | 6/2018 | Sprecher et al. |
| 2018/0215805 A1 | 8/2018 | Hjerrild et al. |
| 2018/0244766 A1 | 8/2018 | Li et al. |
| 2018/0244767 A1 | 8/2018 | Li |
| 2019/0010242 A1 | 1/2019 | Eckelman et al. |
| 2019/0038743 A1 | 2/2019 | Siadak et al. |
| 2019/0040125 A1 | 2/2019 | Leung et al. |
| 2019/0119372 A1 | 4/2019 | Yao et al. |
| 2019/0169285 A1 | 6/2019 | Li et al. |
| 2019/0284272 A1 | 9/2019 | Bammert et al. |
| 2019/0330366 A1 | 10/2019 | Eckelman et al. |
| 2019/0338020 A1 | 11/2019 | Sprecher et al. |
| 2019/0389944 A1 | 12/2019 | Bammert et al. |
| 2020/0048325 A1 | 2/2020 | Zhan et al. |
| 2020/0048627 A1 | 2/2020 | Igawa et al. |
| 2020/0062840 A1 | 2/2020 | Li et al. |
| 2020/0069773 A1 | 3/2020 | Xu et al. |
| 2020/0069814 A1 | 3/2020 | Zhao et al. |
| 2020/0102396 A1 | 4/2020 | Kaneko et al. |
| 2020/0181258 A1 | 6/2020 | Leger et al. |
| 2020/0190203 A1 | 6/2020 | Shih et al. |
| 2020/0216536 A1 | 7/2020 | Brondyk et al. |
| 2020/0276261 A1 | 9/2020 | Zhao et al. |
| 2020/0277348 A1 | 9/2020 | Kitten et al. |
| 2020/0345843 A1 | 11/2020 | Asrat et al. |
| 2020/0362035 A1 | 11/2020 | Brondyk et al. |
| 2021/0009678 A1 | 1/2021 | Hammerberg et al. |
| 2021/0047406 A1 | 2/2021 | Irving et al. |
| 2021/0079105 A1 | 3/2021 | Orengo et al. |
| 2021/0163587 A1 | 6/2021 | Li et al. |
| 2021/0169896 A1 | 6/2021 | Zhao et al. |
| 2021/0268103 A1 | 9/2021 | Brewer et al. |
| 2021/0308277 A1 | 10/2021 | Zhao et al. |
| 2021/0363270 A1 | 11/2021 | Park et al. |
| 2021/0388053 A1 | 12/2021 | Zhan et al. |
| 2021/0393790 A1 | 12/2021 | Zhao et al. |
| 2021/0395340 A1 | 12/2021 | Zhan et al. |
| 2022/0009994 A1 | 1/2022 | Brondyk et al. |
| 2022/0049002 A1 | 2/2022 | Li et al. |
| 2022/0064263 A1 | 3/2022 | Zhan et al. |
| 2022/0324960 A1 | 10/2022 | Li et al. |

FOREIGN PATENT DOCUMENTS

| | | |
|---|---|---|
| EP | 1500329 A2 | 1/2005 |
| EP | 1827485 A2 | 9/2007 |
| EP | 2215124 A1 | 8/2010 |
| EP | 2301965 A1 | 3/2011 |
| EP | 2493925 A1 | 9/2012 |
| EP | 2611462 A2 | 7/2013 |
| EP | 2703486 A1 | 3/2014 |
| EP | 2705053 A1 | 3/2014 |
| EP | 2710040 A1 | 3/2014 |
| EP | 2734549 A1 | 5/2014 |
| EP | 2734549 B1 | 5/2014 |
| EP | 2764026 A2 | 8/2014 |
| EP | 2842573 A1 | 3/2015 |
| EP | 2968454 A1 | 1/2016 |
| EP | 3219729 A1 | 9/2017 |
| EP | 3227342 A1 | 10/2017 |
| EP | 2829551 B1 | 12/2017 |
| EP | 2644698 B1 | 1/2018 |
| JP | 2014-529295 A | 11/2014 |
| JP | 6022563 B2 | 11/2016 |
| RU | 2444528 A | 6/2009 |
| RU | 2009/111884 A | 10/2010 |
| WO | 2003/060080 A2 | 7/2003 |
| WO | 2006081573 A2 | 8/2006 |
| WO | 2006088855 A1 | 8/2006 |
| WO | 2006088955 A2 | 8/2006 |
| WO | 2006122079 A1 | 11/2006 |
| WO | 2007143231 A2 | 12/2007 |
| WO | 2008028192 A2 | 3/2008 |
| WO | 2008086505 A2 | 7/2008 |
| WO | 2009071696 A2 | 6/2009 |
| WO | 2007133816 A3 | 11/2010 |
| WO | 2011/047262 A2 | 4/2011 |
| WO | 2011065935 A1 | 6/2011 |
| WO | 2011106528 A1 | 9/2011 |
| WO | 2013011407 A1 | 1/2013 |
| WO | 2014191391 A1 | 12/2014 |
| WO | 2014208645 A1 | 12/2014 |
| WO | 2015042596 A1 | 3/2015 |
| WO | 2015/067755 A2 | 5/2015 |
| WO | 2015086830 A1 | 6/2015 |
| WO | 2015151079 A2 | 10/2015 |
| WO | 2017025698 A1 | 2/2017 |
| WO | 2018073185 A1 | 4/2018 |
| WO | 2018156180 A1 | 8/2018 |
| WO | 2018156367 A1 | 8/2018 |
| WO | 2019/118512 A2 | 6/2019 |
| WO | 2019/177697 A2 | 9/2019 |
| WO | 2020073345 A1 | 4/2020 |
| WO | 2020155017 A1 | 8/2020 |
| WO | 2020257998 A1 | 12/2020 |
| WO | 2020258893 A1 | 12/2020 |
| WO | 2021041972 A1 | 3/2021 |
| WO | 2021115240 A1 | 6/2021 |
| WO | 2021123092 A1 | 6/2021 |
| WO | 2021123094 A1 | 6/2021 |
| WO | 2021165417 A1 | 8/2021 |
| WO | 2021188631 A1 | 9/2021 |
| WO | 2021212081 A1 | 10/2021 |
| WO | 2021212638 A1 | 10/2021 |
| WO | 2021216810 A1 | 10/2021 |
| WO | 2021216899 A1 | 10/2021 |

(56)  References Cited

FOREIGN PATENT DOCUMENTS

| WO | 2022029447 A1 | 2/2022 |
| WO | 2022049614 A1 | 3/2022 |

OTHER PUBLICATIONS

UniProt Database, IL31 Ra, *Canis lupus familiaris* (Dog), UniProtKB—F1 PTZ6, 7 pages.
UniProt Database, Interleukin 31, *Canis lupus familiaris* (Dog), UniProtKB—C7GOW1, 4 pages.
UniProt Database, OSMR, *Canis lupus familiaris* (Dog), UniProtKB—E2QWS7, 8 pages.
Venereau et al., "Definition and Characterization of an Inhibitor for Interleukin-31," Journal of Biological Chemistry, 2010, 285(20):14955-14963.
Wai et al., "Interleukin-31 Induces Cytokine and Chemokine Production from Human Bronchial Epithelial Cells Through Activation of Mitogen-Activated Protein Kinase Signalling Pathways: Implications for the Allergic Response," Immunology, 2007, 122:532-541.
Winthrop, "The Emerging Safety Profile of JAK Inhibitors in Rheumatic Disease," Nat Rev Rheumatol, 2017, 13(4):234-243, and correction (1 page).
Wood et al., "Despite Identifying Some Shared Gene Associations with Human Atopic Dermatitis the use of Multiple Dog Breeds from Various Locations Limits Detection of Gene Associations in Canine Atopic Dermatitis," Vet Immunol and Immunopath, 2010, 138:193-197.
Wood et al., "Gene Expression in Canine Atopic Dermatitis and Correlation with Clinical Severity Scores," J Dermatol Sci, 2009, 55(1):27-33.
Wood et al., "Reference Genes for Canine Skin When Using Quantitative Real-Time PCR," Vet Immunol Immunopathol, 2008, 126(3-4):392-395.
Xia et al., "Interleukin 31 and Atopic Dermatitis," Intl Journal of Immunol, 2008, 31 (5):383-386.
Yagi et al., "Interleukin-31 Stimulates Production of Inflammatory Mediators from Human Colonic Subepithelial Myofibroblasts." Int J Mol Med, 2007, 19(6):941-946.
Yasukawa et al., "Low-Dose Recombinant Canine Interferon-y for Treatment of Canine Atopic Dermatitis: An Open Randomized Comparative Trial of Two Doses," Vet Dermatol, 2010, 21 (1):42-49.
Zhang et al., "Structures and Biological Functions of IL-31 and IL-31 Receptors," Cytokine Growth Factor Rev., 2008, 19(5-6):347-356, NIH public access version, 18 pages.
"Amended Claims With Annotations", filed Jul. 16, 2020 in Opposition of EP 2734549 (156 pages).
Akira, Shizuo, "Functional Roles of STAT Family Proteins: Lessons from Knockout Mice," Stem Cells, (1999), vol. 17:138-146.
Anti-Feline IL-31 Functional Assay Data, filed in Opposition in EP 3219729 on Nov. 25, 2022 (1 page).
Bachmann et al., "Vaccination against IL-31 for the treatment of atopic dermatitis in dogs," Letters to the Editor, J Allergy Clin Immunol, (2018), vol. 142, No. 1: 279-281.e1, 4 pages.
Bammert et al., "Genome-Wide Expression Patterns in *Saccharomyces cerevisiae*: Comparison of Drug Treatments and Genetic Alterations Affecting Biosynthesis of Ergosterol," Antimicrobial Agents and Chemotherapy, (2000), vol. 44, No. 5: 1255-1265.
Barber et al., "GAPDH as a housekeeping gene: analysis of GAPDH mRNA expression in a panel of 72 human issues," Physiol Genomics, (2005), vol. 21: 389-395.
Bergeron et al., "Comparative functional characterization of canine IgG subclasses," Veterinary Immunology and Immunopathology, (2014), vol. 157, No. 1: 31-41.
Butler et al., "Porcine IgG: structure, genetics, and evolution," IMMUNOGENETICS, (2008), Springer, Berlin, DE, vol. 61, No. 3: 209-230.

Canidae family information submitted in EP 2734549—12748547, dated Jul. 18, 2019, 2 pages.
Carter, Paul J., "Potent antibody therapeutics by design," Nature Reviews Immunology, (2006), Nature Pub. Group, GB, vol. 6: 343-357.
Colman, "Effects of amino acid sequence changes on antibody-antigen interactions," Res Immunol., 1994, 145 1):33-36.
Data and sequence alignments submitted in EP 2734549-12748547, dated Jul. 18, 2019, 9 pages.
Data submitted in EP 2734549-12748547, dated Jul. 18, 2019, 2 pages.
De Bellis, Filippo, "Latest Thinking on Atopic Dermatitis in Cats and Dogs," Apr. 7, 2014, Vet Times, 23 pages.
Decision (Preliminary and Non-binding Opinion of the Opposition Division) and Summons to Attend Oral Proceedings, dated Feb. 28, 2022 in Opposition of EP 3219729 (18 pages).
Decision of the Board of Appeal, EP Opposition EP12748547.2-EP 2734549, dated Apr. 1, 2022, 8 pages.
Declaration of Assistant Prof. Adam Rudinsky, DVM, MS, DACVIM, submitted in Opposition to EP 2734549, dated Jul. 16, 2019, 12 pages.
Declaration of Dr. Anthony Yu, BSc, DVM, MS, ADCD, submitted in Opposition to EP 2734549, dated Jul. 15, 2019, 20 pages.
Declaration of Gary F. Bammert (Second), EP 2734549, EP 12748547, dated Jul. 14, 2020, 3 pages.
Declaration of Gary F. Bammert, EP 2734549, EP 12748547, dated Aug. 28, 2019, 6 pages.
Declaration of Prof. Dr. Ralf Mueller (First), EP 2734549—12748547, dated Jul. 21, 2018, 16 pages.
Declaration of Prof. Dr. Ralf Mueller (Second), EP 2734549—12748547, dated Aug. 22, 2019, 6 pages.
Declaration of Prof. Kun-Liang Guan, Ph.D., submitted in Opposition to EP 2734549, dated Jun. 23, 2019, 40 pages.
Dreuw et al., "Characterization of the Signaling Capacities of the Novel gp130-like Cytokine Receptor*," The Journal of Biological Chemistry, (2004), vol. 279, No. 34, Issue of Aug. 20: 36112-36120.
Emboss Needle alignment canine IL31-mouse IL-31, submitted in Opposition in EP 3219729, (Nov. 2, 2021), 1 page.
Emboss Needle alignment feline IL31-human IL-31, submitted in Opposition in EP 3219729, (Nov. 2, 2021), 1 page.
Emboss Needle alignment feline IL31-mouse IL-31, submitted in Opposition in EP 3219729, (Nov. 2, 2021), 1 page.
Emboss Needle alignment IL-31_felis catus (SEQ ID No. 70)_1L-31 canis lupus, Rundate: Oct. 31, 2021 (1 page).
Emboss Needle alignment, submitted in Opposition in EP 3219729, (Nov. 2, 2021), 1 page.
Experimental Report of IL-31-Induced Stat1-6 Phosphorylation, extracted from WO 2019177697, submitted in EP 2734549 Opposition, Mar. 11, 2011, 3 pages.
Experimental Report of IL-31-Induced Stati-6 Phosphorylation, Filed in the European Patent Office Opposition to European Patent EP 2734549 B1, Jul. 18, 2019, 3 pages.
Experimental report submitted in EP 2734549—12748547, dated Jul. 18, 2019, 3 pages.
Favrot, C. "Feline allergic dermatitis: clinical aspects and diagnosis," (2013), ESVD-ECVD Annual Meeting, 5 pages.
File History of U.S. Appl. No. 17/638,372, filed Feb. 25, 2022.
Finkelstein et al., "Protein Physics," Institute of Protein Research, (2016), Second, Updated and Extended Edition, Lecture 1, p. 11.
Further Written Submissions of Opponent 01, filed Nov. 25, 2022 in Opposition of EP 3219729 (22 pages).
Schulz et al., "A common haplotype of the IL-31 gene influencing gene expression is associated with nonatopic eczema," J Allergy Clin Immunol, (2007), vol. 120, No. 5: 1097-1102.
Sequence Alignment performed Jul. 2, 2019, 3 pages.
Stat3, Wikipedia, from Sep. 3, 2010, using the Internet archive service "Wayback Machine," 1 page.
Statement of grounds of appeal, EP Opposition EP12748547.2-EP 2734549, dated Feb. 28, 2020, 39 pages.
Strohl, W. R., "Fusion Proteins for Half-Life Extension of Biologics as a Strategy to Make Biobetters," Biodrugs, (2015), vol. 29, No. 4: 215-239.

(56) References Cited

OTHER PUBLICATIONS

Table of Antibodies—Excerpt from WO 2019-177697, cited in Opposition of EP 3219729 on Nov. 25, 2022 (1 page).

Third Party Observations According to Art. 115 EPC, dated Apr. 14, 2015, filed in EP 2734549 (9 pages).

Third Party Observations, EP Opposition EP 19196963.3-EP 3653645, dated Aug. 22, 2022, 12 pages.

Tomasco et al., "Comparison of commercial DNA preparation kits for the detection of Brucellae in tissue using quantitative real-time PCR," BMC Infectious Diseases, (2010), vol. 10: 100, 5 pages.

Torres et al., "The immunoglobulin constant region contributes to affinity and specificity," Trends in Immunology, (2008), vol. 29, No. 2: 91-97.

Tricarico et al., "Quantitative real-time reverse transcription polymerase chain reaction: normalization to rRNA or single housekeeping genes is inappropriate for human tissue biopsies," Analytical Biochemistry, (2002), vol. 309: 293-300.

UniProtKB—A0A3Q7TBT9 (A0A3Q7TBT9_VULVU), "Interleukin-31," last modified Jun. 5, 2019, 3 pages.

Vandesompele et al., "Accurate normalization of real-time quantitative RT-PCR data by geometric averaging of multiple internal control genes," Genome Biology, (2002), vol. 3(7): research0034. 1-0034.11.

Weber et al., "Assessment of mRNA and microRNA Stabilization in Peripheral Human Blood for Multicenter Studies and Biobanks," Biomarker Insights, (2010), vol. 5: 95-102.

Wisselink et al., "The efficacy of cyclosporine A in cats with presumed atopic dermatitis: A double blind, randomised prednisolone-controlled study," The Veterinary Journal, (2009), vol. 180: 55-59.

Yaseen et al., "Interleukin-31 promotes pathogenic mechanisms underlying skin and lung fibrosis in sclerodema," Rheumatology, (2020), vol. 0: 1-12.

Zoetis Press Release, Zoetis Receives European Commission Marketing Authorization for Cytopoint (lokivetmab), Apr. 26, 2017, 4 pages.

Zoetis Press Release, "Zoetis Receives USDA License for CYTOPOINT," Dec. 21, 2016, 4 pages.

Aaronson et al., "A Road Map for Those Who Don't Know JAK-STAT," Science, 2002, 296:1653-1655.

Abdi, et al., "IL-31 Is an Inflammatory Pro-Fibrotic Factor Elevated in a Subset of Scleroderma Patients with Severe Pruritus," Abstract No. 821, Arthritis Rheumatol, 2016 68(suppl 10), 2 pages.

Advancing the Science of Atopic Dermatitis Treatment, Canine Atopic Dermatitis Immunotherapeutic Brochure, Zoetis, 2016, 8 pages.

AlphaScreen kits brochure, Perkins Elmer, Mar. 2011, 2 pages.

Bando et al., "Complete Overlap of Interleukin-31 Receptor A and Oncostatin M Receptor B in the Adult Dorsal Root Ganglia with Distinct Developmental Expression Patterns," Neuroscience, 2006, 142(4): 1263-1271.

Bieber et al., "Pathogenesis of Atopic Dermatitis: New Developments," Allergic Dermatosis and Urticaria, (2009), vol. 9: 291-294.

Bilsborough et al., "IL-31 is Associated with Cutaneous Lymphocyte Antigen-Positive Skin Homing T Cells in Patients with Atopic Dermatitis," J Allergy and Clin Immunol, 2006, 117(2):418-425.

Bilsborough et al., "IL-31 Receptor (IL-31 Ra) Knockout Mice Exhibit Elevated Responsiveness to Oncostatin M," J Immunol, 2010, 185:6023-6030.

Bogiatzi et al., "Cutting Edge: Proinflammatory and Th2 Cytokines Synergize to Induce Thymic Stromal Lymphopoietin Production by Human Skin Keratinocytes," J Immunol, 2007, 178:3373-3377.

Boguniewicz et al., "Atopic Dermatitis: A Disease of Altered Skin Barrier and Immune Dysregulation," Immunol Rev., (2011), vol. 242, No. 1: 233-246.

Brandt et al., Th2 Cytokines and Atopic Dermatitis, J Clin Cell Immunol., 2011, 2(3):110, 25 pages.

Buddenkotte et al., "Pathophysiology and Therapy of Pruritus in Allergic and Atopic Diseases," Allergy, 2010, 65:805-821.

Canine Atopic Dermatitis Immunotherapeutic, First to Know Slides, 2015, found at http://o.zoetisus.com/rs/686-BYD-443/images/canine-il-31-first-to-know-slide-deck.pdf, 160 pages.

Canine Atopic Dermatitis Immunotherapeutic: A Caninized Anti-cIL-31 Monoclonal Antibody, FAQ's, o.zoetisus.com/rs/686-BYD-443/images/canine-il-31-faqs.pdf, 16 pages.

Carmi-Levy, et al., "A Modular View of Cytokine Networks in Atopic Dermatitis," Clinic Rev Allerg Immunol, 2011, 41:245-253.

Carr et al., "Investigation of the Pruitogenic Effects of Histamine, Serotonin, Tryptase, Substance P and Interleukin-2 in Healthy Dogs," Vet Dermatol, 2009, 20(2): 105-110.

Castellani et al., "IL-31 a TH2 Cytokine Involved in Immunity and Inflammation," Int J Immunopathol Pharmacol, 2010, 23(3):709-713.

Cevikbas et al., "Interleukin-31 Directly Regulates Neuronal Function in Inflammation and Itch," Journal Inv. Derm. Abstract No. 700, 2010, 130:S117, 2 pages.

Cevikbas et al., "A Sensory Neuron-Expressed IL-31 Receptor Mediates T helper Cell-Dependent Itch: Involvement of TRPV1 and TRPA1 ," J Allergy Clin Immunol, 2014, 133:448-60, 460.e1-e7.

Chattopadhyay et al., "Interleukin-31 and Oncostatin-M Mediate Distinct Signaling Reactions and Response Patterns in Lung Epithelial Cells," Journal of Biological Chemistry, 2007, 282(5):3014-3026.

Chen et al., "Restoration of Tight Junction Structure and Barrier Function by Down-Regulation of the Mitogen-Activated Protein Kinase Pathway in Ras-Transformed Madin-Darby Canine Kidney Cells," Mol Biol Cell, 2000, 11 :849-862.

Cheung et al., "Activation of Human Eosinophils and Epidermal Keratinocytes by Th2 Cytokine IL-31: Implication for the Immunopathogenesis of Atopic Dermatitis," Int Immunol, 2010, 22(6):453-467.

Cornelissen et al., "Signaling by IL-31 and Functional Consequences," European Journal of Cell Biology, 2012, 91 :552-566.

Cosgrove et al., "A Multicentre Clinical Trial to Evaluate the Efficacy and Field Safety of Oclacitinib," Abstract FC-35, Veterinary Dermatology, 2012, 23(Suppl. 1), 1 page.

Cytopoint, European Medicines Agency, European public assessment report (EPAR), 2017, 2 pages.

Cytopoint™ ALK Technical Memo, Apr. 2017, Medical Scientific Affairs, 2 pages.

Dambacher et al., "Interleukin 31 Mediates MAP Kinase and STAT1/3 Activation in Intestinal Epithelial Cells and its Expression is Upregulated in Inflammatory Bowel Disease," Gut, 2007, 56:1257-1265.

Darnell et al., "Jak-STAT Pathways and Transcriptional Activation in Response to IFNs and Other Extracellular Signaling Proteins," Science, 1994, 264(5164):1415-1421, 7 pages.

Dillon et al., "Interleukin 31, a Cytokine Produced by Activated T Cells, Induces Dermatitis in Mice," Nature Immunology, 2004, 5(7):752-760.

Diveu et al., "Predominant Expression of the Long Isoform of GP130-like (GPL) Receptor is Required for Interleukin-31 Signaling," Eur. Cytokine Netw., 2004, 15(4): 291-302.

Estep et al., "High Throughput Solution-Based Measurement of Antibody-Antigen Affinity and Epitope Binning," mAbs, 2013, 5(2):270-278.

Extended European Search Report for European Patent Application No. 18756690.6 dated Nov. 2, 2020, 9 pages.

Ezzat et al., "Serum Measurement of Interleukin-31 (IL-31) in Paediatric Atopic Dermatitis: Elevated Levels Correlate with Severity Scoring," JEADV, 2011, 25:334-339.

Felsburg, "Overview of Immune System Development in the Dog: Comparison with Humans," Hum Exp Toxicol, 2002, 21(9-10):487-92.

File History of U.S. Appl. No. 15/467,464, filed Mar. 23, 2017.

File History of U.S. Appl. No. 15/844,142, filed Dec. 15, 2017.

File History of U.S. Appl. No. 16/186,013, filed Nov. 9, 2018.

File History of U.S. Appl. No. 16/488,045, filed Aug. 22, 2019.

Fleck, et al., "Comparison of the Janus Kinase (JAK) Inhibitor, Oclacitinib, and Prednisolone in Canine Models of Pruritus," Abstract FC-36, Veterinary Dermatology, 2012, 23(Suppl. 1), 1 page.

(56)     References Cited

OTHER PUBLICATIONS

Gonzales et al., "Interleukin-31: Its Role in Canine Pruritus and Naturally Occurring Canine Atopic Dermatitis," Vet Dermatol, 2013, 24:48-53 and e11-e12.

Gonzales et al., "Oclacitinib (Apoquel®) is a novel Janus kinase inhibitor with activity against cytokines involved in allergy," Journal of Veterinary Pharmacology and Therapeutics, 2014, 37:317-24.

Gonzales et al., "Oclacitinib (Apoquel®; Zoetis) is a novel Janus kinase inhibitor that has activity against canine pro-allergic and pro-inflammatory cytokines," Abstracts of the 25th Annual Congress of the ECVD-ESVD, Sep. 19-21, 2013, Valencia, Spain, Veterinary Dermatology, 2013, 24:377-397, at pp. 384-385.

Gonzolas, et al., "IL-31: Its Role in Canine Pruritus and Prevalence in Naturally Occurring Canine Atopic Dermatitis," Abstract Supporting Original Study 5, Veterinary Dermatology, 2012, 23(Suppl. 1):6.

Grimstad et al., "Anti-Interleukin-31-Antibodies Ameliorate Scratching Behaviour in NC/Nga Mice: A Model of Atopic Dermatitis," Experimental Dermatology, 2009, 18(1):35-43.

Gutzmer et al., "Pathogenetic and therapeutic implications of the histamine H4 receptor in inflammatory skin diseases and pruritus," Frontiers in Bioscience S3, (2011), pp. 985-994.

Gutzwiller, M. E. R., "Canine Dendritic Cells and Their Involvement in Atopic Dermatitis," Dissertation, Bern, (2010), 69 pages.

Haitina et al., The G Protein-Coupled Receptor Subset of the Dog Genome is More Similar to that in Humans than Rodents, BMC Genomics, 2009, 10:24, 13 pages.

Halliwell et al., "The ACVD task force on canine atopic dermatitis (111): the role of antibodies in canine atopic dermatitis," Veterinary Immunology and Immunpathology, 2001, 81 (3-4):159-167.

Hashimoto et al., "Itch-Associated Scratching Contributes to the Development of Dermatitis and Hyperimmunoglobulinaemia E in NC/Nga Mice," Experimental Dermatology, 2011, 20:820-825.

Hashizume et al., "IL-6 Plays an Essential Role in Neutrophilia Under Inflammation," Cytokine, 2011, 54:92-99.

Grau-Vorster, et al., "Levels of IL-17F and IL-33 correlate with HLA-DR activation in clinical-grade human bone marrow-derived multipotent mesenchymal stromal cell expansion cultures," Cytotherapy. Jan. 2019;21(1):32-40. (Abstract provided).

Chunxiu, et al., "Research progress on the correlation between interleukin-31 and atopic dermatitis," China Medical Innovation. 2016 Issue 36 133-136 (Abstract Provided).

Moyaert et al., "A Blinded, Randomized Clinical Trial Evaluating the Efficacy and Safety of Lokivetmab Compared to Ciclosporin in Client-Owned Dogs with Atopic Dermatitis," Vet Dermatol, 2017, 28(6):593-603 and e144-e145.

Nakamura et al., "Pruritogenic mediators in psoriasis vulgaris: comparative evaluation of itch-associated cutaneous factors," British J of Dermatol, 2003, 149:718-730.

National Human Genome Research Institute (NHGRI), "Researchers Publish Dog Genome Sequence," 2005, 2 pages.

Nattkemper et al., "Cutaneous T-cell Lymphoma and Pruritus: The Expression of IL-31 and its Receptors in the Skin," Acta Derm Venereal, 2016, 96:894-898.

Neis et al., "Enhanced Expression Levels of IL-31 Correlate with IL-4 and IL-13 in Atopic and Allergic Contact Dermatitis," J Allergy Clin Immunol, 2006, 118(4):930-937.

Niyonsaba et al., "Antimicrobial Peptides Human 13-Defensins and Cathelicidin LL-37 Induce the Secretion of a Pruritogenic Cytokine IL-31 by Human Mast Cells," J Immunol, 2010, 184:3526-3534.

Nobbe et al., "IL-31 Expression by Inflammatory Cells is Preferentially Elevated in Atopic Dermatitis," Acta Derm Venereal, 2012, 92:24-28, comment on same at 92:5-6.

Nuttall et al., "Expression of Th1, Th2 and Immunosuppressive Cytokine Gene Transcripts in Canine Atopic Dermatitis," Clin Exp Allergy, 2002, 32(5):789-795.

Nuttall et al., "T-Helper 1, T-helper 2 and Immunosuppressive Cytokines in Canine Atopic Dermatitis," Veterinary Immunol Immunopathol, 2002, 87(3-4):379-384.

O'Kennedy et al., "A Review of Enzyme-Immunoassay and a Description of a Competitive Enzyme-Linked Immunosorbent Assay for the Detection of Immunoglobulin Concentrations," Biochemical Education, 1990, 18(3):136-140.

Olivry et al., "Interventions for Atopic Dermatitis in Dogs: A Systematic Review of Randomized Controlled Trials," Vet Dermatol, 2010, 21 :4-22.

Olivry et al., "The ACVD Task Force on Canine Atopic Dermatitis: Forewords and Lexicon," Veterinary Immunology and Immunpathology, 2001, 81 (3-4):143-146.

Olivry et al., "Toward a Canine Model of Atopic Dermatitis Amplification of Cytokine-Gene Transcripts in the Skin of Atopic Dogs," Exp Dermatol, 1999, 8(3):204-211.

Olivry et al., "Treatment of Canine Atopic Dermatitis: 2010 Clinical Practice Guidelines from the International Task Force on Canine Atopic Dermatitis," Vet Dermatol, 2010, 21 (3):233-248.

O'Shea et al., "A New Modality for Immunosuppression: Targeting the JAK/STAT Pathway," Nat Rev Drug Discov, 2004, 3(7):555-564.

Pedersen et al., "Identification of Monoclonal Antibodies that Cross-React with Cytokines from Different Animal Species," Vet Immunol and Immunopath, 2002, 88:111-122.

Perrigoue et al., "IL-31-IL-31 R Interactions Limit the Magnitude of Th2 Cytokine-Dependent Immunity and Inflammation Following Intestinal Helminth Infection," J Immunol, 2009, 182(10):6088-6094.

Picco et al., "A Prospective Study on Canine Atopic Dermatitis and Food-Induced Allergic Dermatitis in Switzerland," Vet. Dermatol, 2008, 19(3): 150-155.

Post-published data from Zoetis for two anti-feline IL-31 antibodies (extracted from WO 2019/177697), submitted in Opposition in EP 3219729, (submitted on Mar. 11, 2011), 4 pages.

Prelaud et al., "Reevaluation of Diagnostic Criteria of Canine Atopic Dermatitis," Revue de Medecine Veterinaire, 1998, 149:1057-1064, English abstract only.

Product Sheet, DH82, CRL-10389(TM), ATCC, 2021, 7 pages.

Prost, C., "Feline atopic dermatitis: Clinical signs and diagnosis," EJCAP, (2009), vol. 19, No. 3: 223-229.

Pucheu-Haston et al., "A Canine Model of Cutaneous Late-Phase Reactions: Prednisolone Inhibition of Cellular and Cytokine Responses," Immunology, 2005, 117:177-187.

Raap et al., "Correlation of IL-31 Serum Levels with Severity of Atopic Dermatitis," J Allergy Clin Immunol, 2008, 122(2):421-423.

Raap et al., "Increased Levels of Serum IL-31 in Chronic Spontaneous Urticaria," Exp. Dermatol., 2010, 19(5):464-466.

Rawlings et al., The JAK/STAT Signaling Pathway, J Cell Science, 2004, 117:1281-1283.

Reichmann et al., "Reshaping Human Antibodies for Therapy," Nature, 1988, 332:323-327.

Reply to appeal, EP Opposition EP12748547.2-EP 2734549, dated Jul. 16, 2020, 58 pages.

Rudikoff et al. Proc. Natl. Acad. Sci. USA vol. 79, pp. 1979-1983 (Mar. 1982).

Saeki et al., Thymus and Activation Regulated Chemokine (TARC)/CCL 17 and Skin Diseases, J Derma Science, 2006, 43:75-84.

Saleem, et al., "Interleukin-31 Pathway and Its Role in Atopic Dermatitis: A Systematic Review," J Dermatolg Treat., 2017, 28(7):591-599.

Sandilands et al., "Filaggrin in the Frontline: Role in Skin Barrier Function and Disease," J Cell Science, 2009, 122:1285-1294.

Santoro, et al., "Canine and Human Atopic Dermatitis: Two Faces of the Same Host-Microbe Interaction," J Investigative Dermatol, 2016, 136:1087-1089.

Scheerlinck et al., "Functional and Structural Comparison of Cytokines in Different Species, " Vet Immunol mmunopathol, 1999, 72(1-2):39-44.

Schlothauer et al., "Novel human IgG1 and IgG4 Fc-engineered antibodies with completely abolished immune effector functions," Protein Engineering, Design and Selection, (2016), vol. 29, No. 10: 457-466.

Schlotter et al., "Lesional Skin in Atopic Dogs Shows a Mixed Type-1 and Type-2 Immune Responsiveness," Vet Immunol Immunopathol, 2011, 143(1-2):20-26.

(56) References Cited

OTHER PUBLICATIONS

Schwartzman et al., "Canine Reaginic Antibody: Characterization of the Spontaneous Anti-Ragweed and Induced Anti-Dinitrophenyl Reaginic Antibodies of the Atopic Dog," Clin. exp. Immunol., (1971), vol. 9: 549-569.

Scott et al., "Treatment of Canine Atopic Dermatitis with a Commercial Homeopathic Remedy: A Single-Blinded, Placebo-Controlled Study," Can Vet J, 2002, 43(8):601-603.

Shen et al., "Single Variable Domain-IgG Fusion: A Novel Recombinant Approach to Fc Domain-Containing Bispecific Antibodies," The Journal of Biological Chemistry, (2006), vol. 281, No. 16: 10706-10714.

Song et al., "JAK1 Activates STAT3 Activity in Non-Small-Cell Lung Cancer and IL-6 Neutralizing Antibodies Can Suppress JAK1-STA T3 Signaling," Mol Cancer Ther, 2011, 10(3):481-494.

Sonkoly et al., "IL-31: A New Link Between T Cells and Pruritus in Atopic Skin Inflammation," J Allergy Clin Immunol, 2006, 117(2):411-417.

Soumelis et al., "Human Epithelial Cells Trigger Dendritic Cell-Mediated Allergic Inflammation by Producing TSLP," Nat Immunol, 2002, 3(7):673-680.

Sousa et al., "The ACVD Task Force on Canine Atopic Dermatitis (II): Genetic Factors," Veterinary Immunology and Immunopathology, 2001, 81 (3-4):153-157.

Strachan et al., "Family Size, Infection, and Atopy: The First Decade of the Hygiene Hypothesis," Thorax, 2000, 55 (Suppl 1): S2-S10.

Strietzel et al., "In Vitro functional characterization of feline IgGs," Veterinary Immunology and Immunopathology, (2014), vol. 158, No. 3: 214-223.

Suter et al., "The keratinocyte in epidermal renewal and defence," Veterinary Dermatology, (2009), vol. 20, 515-532.

Takaoka et al., "Expression of IL-31 Gene Transcripts in NC/Nga Mice with Atopic Dermatitis," European Journal of Pharmacology, 2005, 516(2):180-181.

Takaoka et al., "Involvement of IL-31 on Scratching Behavior in NC/Nga Mice with Atopic-Like Dermatitis," Experimental Dermatology, 2006, 15(3):161-167.

Tang, "Molecular Cloning of Canine IL-13 Receptor a Chain (a1 and a2) cDNAs and Detection of Corresponding mRNAs in Canine Tissues, " Veterinary Immunology and Immunopathology, 2001, 79(3-4):181-195.

Terada et al., "Clinical Comparison of Human and Canine Atopic Dermatitis Using Human Diagnostic Criteria: Proposal of Provisional Diagnostic Criteria for Canine Atopic Dermatitis," Journal of Dermatology, 2011, 38:784-790.

Hashizume et al., The Roles of Interleukin-6 in the Pathogenesis of Rheumatoid Arthritis, Arthritis, 2011, Article ID 765624, 8 pages.

Mizuno et al., "Molecular Cloning of Canine Interleukin-31 and its Expression in Various Tissues," Veterinary Immunology and Immunopathology, 2009, 131 :140-143.

Hawro et al., "Interleukin-31 Does Not Induce Immediate Itch in Atopic Dermatitis Patients and Healthy Controls after Skin Challenge," Allergy, 2014, 69:113-117.

Hill et al., "Pilot Study of the Effect of Individualised Homeopathy on the Pruritus Associated with Atopic Dermatitis in Dogs," Vet. Rec., 2009, 164(12):364-70.

Hill, R. E., "Center for Veterinary Biologics Notice No. 13-05," United States Department of Agriculture, Animal and Plant Health Inspection Service, Veterinary Services, Center for Veterinary Biologics, Ames, Iowa, dated Mar. 4, 2013.

Hillier et al., The ACVD Task Force on Canine Atopic Dermatitis (I): Incidence and Prevalence, Veterinary Immunology and Immunopathology, 2001, 81 :147-151.

Hirano et al., "Signaling Mechanisms Through gp130: A Model of the Cytokine System," Cytokme & Growth Factor Reviews, (1997), vol. 8., No. 4: 241-252.

Holsapple et al., "Species Comparison of Anatomical and Functional Immune System Development," Birth Defects Res B Dev Reprod Toxicol., 2003, 68(4):321-34.

Hong et al., "Functional Regulation of Interleukin-31 Production by its Genetic Polymorphism in Patients with Extrinsic Atopic Dermatitis," Acta Derm Venereal, 2012, 92(4): 430-432.

Humphrey, et al., "Development of a Model of IL-31 Induced Pruritus in Beagle Dogs," Abstract FC-30, Veterinary Dermatology, 2012, 23(Suppl. 1), 1 page.

Hvid et al., "IL-25 in Atopic Dermatitis: A Possible Link Between Inflammation and Skin Barrier Dysfunction," J Invest Dermatol, 2011, 131 (1): 150-157.

IL-31 Antibody (Aviva Systems Biology) Oct. 11, 2016 [retrieved on Apr. 24, 2018, www.avivasysbio.com/en/il31-antibody-n-terminal-region-oaab05980.html], 2 pages.

IL-31 Antibody: (Aviva Systems Biology) Publication date [retrieved on Apr. 24, 2018, www.google.com/search?q=I L31 +Antibody+-+N-terminal+reg ion+-%280AAB05980%29+from+Aviva+Systems+Biology&rlz=1 C1 Ggrv _ en U S769US769&source=I nt&tbs=cdr%3A 1 %2Ccd_min%3A %2Ccd_max%3A2.24.2017 &tbm=], 1 page.

IL-31 sequence alignments, submitted in Opposition in EP 3219729, (submitted on Jun. 9, 2021), 1 page.

ImmunoGlobe® product information, Antikorpertechnik GmbH, 2 pages.

Incorvaia et al., "Allergy and the skin," Clinical and Experimental Immunology, (2008), vol. 153, Suppl. 1: 27-29.

International Nonproprietary Names for Pharmaceutical Substances (INN) excerpt for Lokivetmab, WHO Drug Information, 2015, 29(3):407-408.

International Search Report and Written Opinion for PCT/US2018/017623, dated May 15, 2018, 15 pages.

International Search Report received in PCT/US2017/023788, dated Jun. 6, 2017, 12 pages.

Janeway et al. Immunology, 3rd ed., 1997, Garland Publications, Inc., pp. 3:1-3: 11.

Javens et al., "Oclacitinib Inhibits Canine IL-4 and IL-13-activated JAK-STAT Pathways in Canine DH82 Cells," 2018 3pt Proceedings of the North American Veterinary Dermatology Forum, May 1-5, 2018, p. 104.

Jin et al., "Animal Models of Atopic Dermatitis," J Invest Dermatol, 2009, 129(1):31-40.

Michels et al., "A blinded, randomized, placebo-controlled, dose determination trial of lokivetmab (ZTS-00103289), a caninized, anti-canine IL-31 monoclonal antibody in client owned dogs with atopic dermatitis," Vet Dermatol, 2016, 27 (6): 478-e129.

Kanda et al., "Characterization of Canine Filaggrin: Gene Structure and Protein Expression in Dog Skin," Vet Dermatol, 2013, 24:25-31, e7.

Kasraie et al., "Interleukin (IL)-31 Induces Pro-Inflammatory Cytokines in Human Monocytes and Macrophages Following Stimulation with Staphylococcal Exotoxins," Allergy, 2010, 65:712-721.

Kasraie et al., "Functional Effects of Interleukin 31 in Human Primary Keratinocytes," Allergy, 2011, 66:845-852.

Kasraie et al., "Interleukin (IL)-31 Activates Signal Transducer and Activator of Transcription (STAT)-1, STAT-5 and Extracellular Signal-Regulated Kinase 1/2 and Down-Regulates IL-12p40 Production in Activated Human Macrophages," Allergy, 2013, 68:739-747.

Kasutani et al., "Anti-IL-31 Receptor Antibody is Shown to be a Potential Therapeutic Option for Treating Itch and Dermatitis in Mice," British Journal of Pharmacology, 2014, 171 :5049-5058.

Kindred Biosciences' (KIN) CEO Richard Chin on Q1 2017 Results—Earnings Call Transcript, 2017, 3 pages.

Kovalik et al., "The Use of Ciclosporin A in Veterinary Dermatology," Vet J, 2012, 193(2):317-25.

Le Saux et al., "Molecular Dissection of Human Interleukin-31-Mediated Signal Transduction through Site-Directed Mutagenesis," Journal of Biological Chemistry, 2010, 285(5):3470-3477.

Leung et al., "Atopic Dermatitis," Lancet, 2003, 361 :151-60.

Leung, "Human Atopic Dermatitis: From Laboratory Research to Bedside," Scientific Session Presentations, 2010, found at http://ssms.weblinkconnect.com/CWT/EXTERNAL/WCPAGES_NAVDF/PDF/ARCHIVES/ 201 Oscientific.PDF; 60 pages.

(56) References Cited

OTHER PUBLICATIONS

Maeda et al., "Expression Analysis of CCL27 and CCL28 mRNA in Lesion al and Non-Lesional Skin of Dogs with Atopic Dermatitis," J Vet. Med. Sci., 2008, 70(1):51-55.

Maeda et al., "Expression of CC Chemokine Receptor 4 (CCR4) mRNA in Canine Atopic Skin Lesion," Veterinary Immunology and Immunopathology, 2002, 90(3-4): 145-154.

Maeda et al., "Lesional Expression of Thymus and Activation-Regulated Chemokine in Canine Atopic Dermatitis," Vet Immunol Immunopathol, 2002, 88(1-2):79-87.

Maeda S. et al., "Production of a Monoclonal Antibody to Canine Thymus and Activation-Regulated Chemokine (TARC) and Detection of TARC in Lesional Skin from Dogs with Atopic Dermatitis," Veterinary Immunology and mmunopathology, 2005, 103(1-2):83-92.

Marsella et al., "Animal Models of Atopic Dermatitis," Clinics in Dermatology, 2003, 21(2):122-133.

Marsella et al., "Canine Models of Atopic Dermatitis: A Useful Tool with Untapped Potential," Journal of Investigative Dermatology, 2009, 129:2351-2357.

Marsella et al., "Current evidence of skin barrier dysfunction in human and canine atopic dermatitis," Veterinary Dermatology, (2011), vol. 22, 239-248.

Marsella et al., "Current Understanding of the Pathophysiologic Mechanisms of Canine Atopic Dermatitis," Journal of the American Veterinary Medical Association, 2012, 241 :194-207.

Marsella et al., "Pilot Investigation of a Model for Canine Atopic Dermatitis: Environmental House Dust Mite Challenge of High-Ig-E-Producing Beagles, Mite Hypersensitive Dogs with Atopic Dermatitis and Normal Dogs, " Veterinary Dermatology, 2006, 17:24-35.

Marsella et al., "Transmission Electron Microscopy Studies in an Experimental Model of Canine Atopic Dermatitis," Veterinary Dermatology, 2010, 21 :81-88.

McCandless et al., "Allergen-Induced Production of IL-31 by Canine Th2 Cells and Identification of Immune, Skin, and Neuronal Target Cells," Veterinary Immunology and Immunopathy, 2014, 157:42-48.

McCandless et al., "Production of IL-31 by Canine Th2 Cells and Identification of Inflammatory and Neuronal Target Cells," Abstract FC-65, Veterinary Dermatology, 2012, 23(Suppl. 1), 1 page.

Meng, et al., "New mechanism underlying IL-31-induced atopic dermatitis," J Allergy Clin Immunol, 2018, 141:1677-89, 1689.e1-e8.

Merryman-Simpson et al., "Gene (mRNA) Expression in Canine Atopic Dermatitis: Microarray Analysis," Vet Dermatol, 2008, 19(2):59-66.

Metz et al., "Pruritus: an Overview of Current Concepts," Vet Dermatol, 2011, 22(2):121-31.

Further Written Submissions of Opponent 02, filed Nov. 24, 2022 in Opposition of EP 3219729 (36 pages).

GenBank NCBI Sequence XM_011287838.1, "Predicted: Felis catus interleuikin 31 (IL31), mRNA," Feb. 10, 2015, 1 page.

Gibbs et al., "Role of the Pruritic Cytokine IL-31 in Autoimmune Skin Diseases," Frontiers in Immunololgy, (2019), vol. 10, Article 1383: 1-6.

Grimstad et al., "The Effect of Anti-Interleukin-31-Antibodies on Scratching Behaviour and Development of Dermatitis on NC/NGA Mice," Inflamm. Res., (2007), Supplement 3, FC09.7, S396-S397.

Halliwell, R. E. W., "The immunopathogenesis of allergic skin diseases in dogs and cats," EJCAP, (2009), vol. 19, No. 3: 213-218.

Harrison et al., "The use of quantitative RT-PCR to measure mRNA expression in a rat model of focal ischemia—caspase-3 as a case study," Molecular Brain Research, (2000), vol. 75: 143-149.

Heise et al., "IL-31 Receptor Alpha Expression in Epidermal Keratinocytes Is Modulated by Cell Differentiation and Interferon Gamma," Journal of Investigative Dermatology, (2009) vol. 129, 240-243.

Hill et al., "Survey of the prevalence, diagnosis and treatment of dermatological conditions in small animals in general practice, " Veterinary Record, (2006), vol. 158: 533-539.

Hobi et al., "Clinical characteristics and causes of pruritus in cats: a multicentre study on feline hypersensitivity-associated dermatoses," Vet. Dermatol., (2011), 1-8.

IL-31 Sequence Alignments, Filed in the European Patent Office Opposition to European Patent EP 3219729, Jun. 9, 2021, 2 pages.

Interdog: Canine Interferon-y Preparation (Genetically Modified), Toray Group, accessed at https://www.toray.com/products/chemicals/che_0060.html, on Aug. 27, 2019.

International Preliminary Report on Patentability and Written Opinion for PCT/US2020/048618, dated Mar. 1, 2022, 7 pages.

International Search Report and Written Opinion for PCT/US2020/048618, mailed Jan. 21, 2021, 11 pages.

International Search Report and Written Opinion received in PCT/US2021/028548, mailed Sep. 2, 2021, 8 pages.

Ip et al., "Interleukin-31 induces cytokine and chemokine production from human bronchial epithelial cells through activation of mitogen-activated protein kinase signalling pathways: implications for the allergic response," Immunology, (2007), vol. 122: 532-541.

Jarilin, "Osnovy immunologii", M. Medicina: pp. 172-174, with Machine Translation.

King, Stephen, et al. "A randomized double-blinded placebo-controlled study to evaluate an effective ciclosporin dose for the treatment of feline hypersensitivity dermatitis" Veterinary Dermatology, vol. 23, pp. 440-e84, Oct. 2012.

Kruse et al., "Transcriptome and proteome responses in RNAlater preserved tissue of *Arabidopsis thaliana*," PLoS One, (2017), vol. 12, No. 4: e0175943, 10 pages.

Lai et al., "Interleukin-31 expression and relation to disease severity in human asthma," Scientific Reports, (2016), vol. 6: 22835, 1-9.

Lewis et al., "The different effector function capabilities of the seven equine IgG subclasses have implications for vaccine strategies," Molecular Immunology, (2008), vol. 45, No. 3: 818-827.

Liu et al., "A SYBR Green I real-time RT-PCR assay for detection and differentiation of influenza A(H1N1) virus in swine populations," Journal of Virological Methods, (2009), vol. 162: 184-187.

Maeda et al., "Engineering of Functional Chimeric Protein G-Vargula Luciferase," Analytical Biochemistry, (1997), vol. 249: 147-152.

Marsella et al., "Atopic Dermatitis in Animals and People: An Update and Comparative Review," Vet. Sci., (2017), vol. 4: 37, 19 pages.

Medina-Cucurella et al., "Feline Interleukin-31 Shares Overlapping Epitopes with the Oncostatin M Receptor and IL-31RA," Biochemistry, (2020), vol. 59: 2171-2181, and S1-S10.

Menotti-Raymond et al., "Mutation in CEP290 Discovered for Cat Model of Human Retinal Degeneration," Journal of Heredity, (2007), vol. 98, No. 3: 211-220.

Minutes of the oral proceedings, EP Opposition EP12748547.2-EP 2734549, dated Mar. 31, 2022, 4 pages.

Nagaoka et al., "Single amino acid substitution in the mouse IgG1 Fc region induces drastic enhancement of the affinity to protein A," Protein Engineering, (2003), vol. 16, No. 4: 243-245.

Noli, Chiara, et al. "A double-blinded, randomized, methylprednisolone-controlled study on the efficacy of oclacitinib in the management of pruritus in cats with nonflea nonfood-induced hypersensitivity dermatitis" Veterinary Dermatology, vol. 30, pp. 440-e30, Apr. 2019.

Notice of Appeal, EP Opposition EP12748547.2-EP 2734549, dated Dec. 19, 2019, 3 pages.

Notice of Opposition 1, EP Opposition EP12748547.2-EP 2734549, dated Feb. 21, 2018, 41 pages.

Notice of Opposition 1, EP Opposition EP17168574.6-EP 3219729, dated Jun. 9, 2021, 43 pages.

Notice of Opposition 2, EP Opposition EP12748547.2-EP 2734549, dated Feb. 23, 2018, 24 pages.

Notice of Opposition 2, EP Opposition EP17168574.6-EP 3219729, dated Jun. 9, 2021, 26 pages.

Olivry et al., "Early Activation of Th2/Th22 Inflammatory and Pruritogenic Pathways in Acute Canine Atopic Dermatitis Skin Lesions," Journal of Investigative Dermatology, (2016), vol. 136: 1961-1969.

(56)             References Cited

OTHER PUBLICATIONS

Passow et al., "Nonrandom RNAseq gene expression associated with RNAlater and flash freezing storage methods," Mol Ecol Resour., (2019), vol. 19(2): 456-464.

Plager et al., "Gene transcription abnormalities in canine atopic dermatitis and related human eosinophilic allergic diseases," Vet Immunol Immunopathol., (2012), vol. 149(0): 136-142.

Pontius et al., "Initial sequence and comparative analysis of the cat genome," Genome Research, (2007), vol. 17: 1675-1689.

Preliminary Opinion Board of Appeal, EP Opposition EP12748547.2-EP 2734549, dated Feb. 23, 2020, 12 pages.

Radstrom et al., "Pre-PCR Processing: Strategies to Generate PCR-Compatible Samples," Molecular Biotechnology, (2004), vol. 26: 133-146.

Rejection of the Opposition, EP Opposition EP12748547.2-EP 2734549, dated Oct. 21, 2019, 25 pages.

Reply to Opposition Proceedings in EP 3219729, dated Nov. 3, 2021 (218 pages).

Reply to Opposition, EP Opposition EP12748547.2-EP 2734549, dated Jul. 23, 2018, 47 pages.

Reply to Opposition, EP Opposition EP17168574.6-EP 3219729, dated Nov. 3, 2021, 66 pages.

Reply to the Summons to Attend Oral Proceedings, filed Nov. 25, 2022 in Opposition of EP 3219729 (19 pages).

Robinson et al., "Clinical Consequences of Targeting IL-17 and TH17 in Autoimmune and Allergic Disorders," Curr Allergy Asthma Rep, (2013), vol. 13, No. 6: 1-14.

Roosje et al., "Feline Atopic Dermatitis: A Model for Langerhans Cell Participation in Disease Pathogenesis," American Journal of Pathology, (1997), vol. 151, No. 4: 927-932.

Roosje et al., "Increased Nos. of CD4+ and CD8+ T Cells in Lesional Skin of Cats with Allergic Dermatitis," Vet Pathol, (1998), vol. 35: 268-273.

Rugg et al., "Immunohistochemical Evaluation of IL-31 Receptor A Localization in Neuronal and Cutaneous Tissues of Beagle Dogs," Zoetis Inc., Florham Park, NJ, USA.

Safdari et al., "Antibody humanization methods—a review and update," Biotechnology and Genetic Engineering Reviews, (2013), vol. 29, No. 2: 175-186.

Sapunar et al., "Dorsal root ganglion—a potential new therapeutic target for neuropathic pain," Journal of Pain Research, (2012), vol. 5: 31-38.

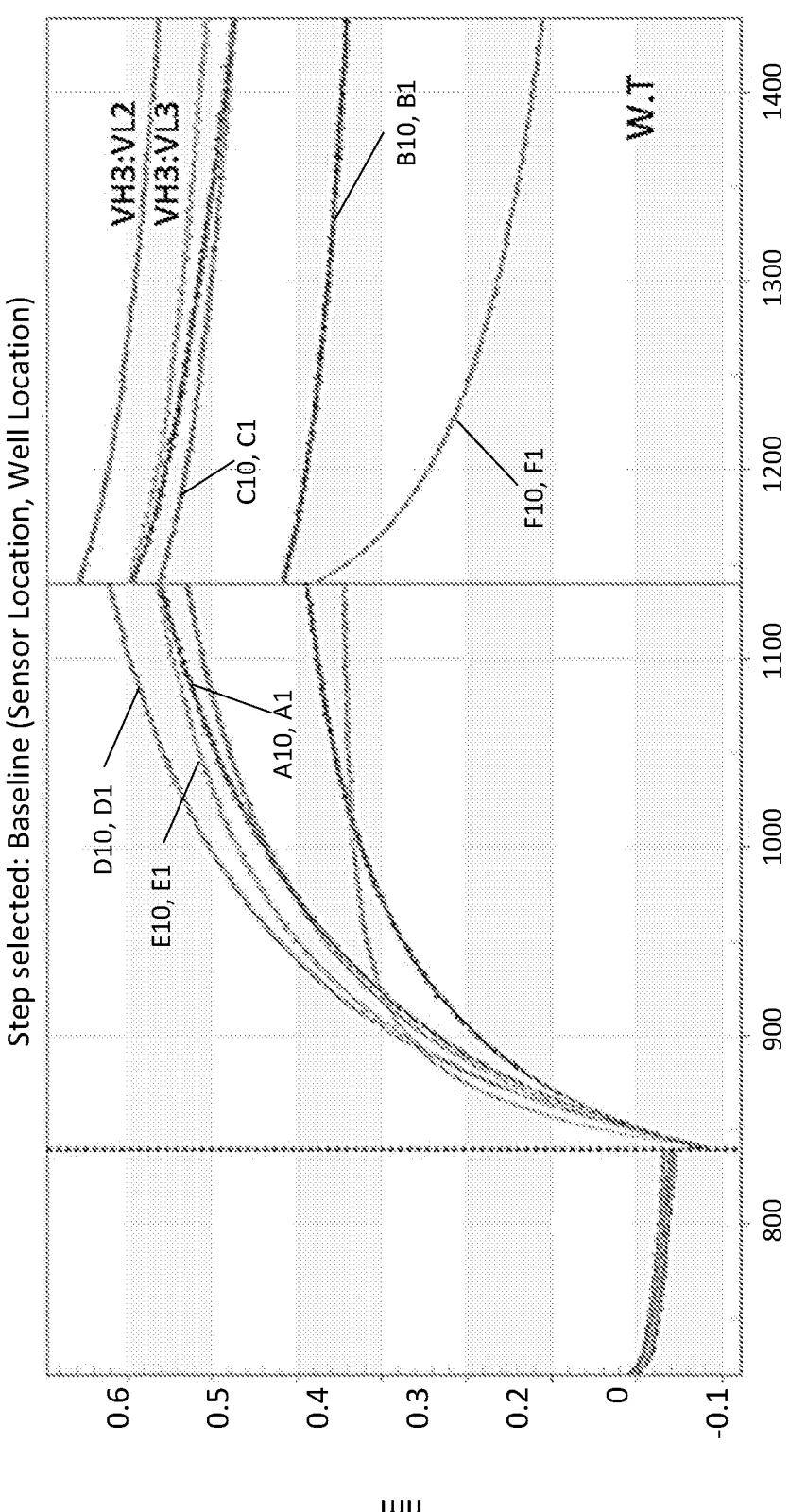

ANTI-IL31 ANTIBODIES FOR VETERINARY USE

CROSS-REFERENCE TO RELATED APPLICATIONS

This application is a national stage entry of International Patent Application No. PCT/US2020/048618, filed Aug. 28, 2020, which claims the benefit of priority of U.S. Provisional Application No. 62/893,799, filed Aug. 29, 2019, and U.S. Provisional Application No. 62/894,526, filed Aug. 30, 2019, each of which is incorporated by reference herein in its entirety for any purpose.

FIELD

This invention relates to isolated anti-IL31 antibodies, for example, with enhanced binding to canine IL31 and feline IL31, and methods of using the same, for example, treating IL31-induced conditions or reducing IL31 signaling function in cells, for instance in companion animals, such as canines and felines.

BACKGROUND

Interleukin 31 (IL31) is a cytokine mostly produced by Th2 cells and understood to be involved in promoting skin disease, such as pruritic and other forms of allergic diseases (for example, atopic dermatitis). IL31 functions by binding its receptor complex (a complex of IL31 receptor A (IL-31Ra) and Oncostatin M receptor (OSMR) subunits) and activating downstream activities, such as activation of JAK kinases and subsequent phosphorylation and activation of STAT1, STAT3, and STATS. Activation of this pathway is thought to cause many of the clinical problems associated with dermatitis and other disorders.

Companion animals such as cats, dogs, and horses, suffer from many skin diseases similar to human skin diseases, including atopic dermatitis. However, the IL31 sequence is divergent between human, cat, dog, and horse. There remains a need, therefore, for methods and compounds that can be used specifically to bind companion animal IL31 for treating IL31-induced conditions and for reducing IL31 signaling.

SUMMARY

Embodiment 1. An isolated antibody that binds to canine IL31 or feline IL31, wherein the antibody comprises:
  a) a heavy chain comprising a CDR-H3 sequence having the amino acid sequence of SEQ ID NO: 14 or SEQ ID NO: 15; and/or
  b) a light chain comprising a CDR-L1 sequence having the amino acid sequence of SEQ ID NO: 20; and/or
  c) a light chain comprising a CDR-L3 sequence having the amino acid sequence of SEQ ID NO: 23 or SEQ ID NO: 24.

Embodiment 2. An isolated antibody that binds to canine IL31 or feline IL31, wherein the antibody comprises:
  a) a heavy chain comprising a CDR-H1 sequence having the amino acid sequence of SEQ ID NO: 11, a CDR-H2 sequence having the amino acid sequence of SEQ ID NO: 12, and a CDR-H3 sequence having the amino acid sequence of SEQ ID NO: 13, SEQ ID NO: 14, or SEQ ID NO: 15; and/or
  b) a light chain comprising a CDR-L1 sequence having the amino acid sequence of SEQ ID NO: 20, a CDR-L2 sequence having the amino acid sequence of SEQ ID NO: 21, and a CDR-L3 sequence having the amino acid sequence of SEQ ID NO: 22, SEQ ID NO: 23, or SEQ ID NO: 24.

Embodiment 3. The antibody of any one of the preceding embodiments, wherein the antibody binds to canine IL31 or feline IL31 with a dissociation constant (Kd) of less than less than $5 \times 10^{-8}$ M, less than $1 \times 10^{-8}$ M, less than $5 \times 10^{-9}$ M, less than $1 \times 10^{-9}$ M, less than $5 \times 10^{-10}$ M, less than $1 \times 10^{-10}$ M, less than $5 \times 10^{-11}$ M, less than $1 \times 10^{-11}$ M, less than $5 \times 10^{-12}$ M, or less than $1 \times 10^{-12}$ M, as measured by biolayer interferometry.

Embodiment 4. The antibody of any one of the preceding embodiments, wherein the antibody reduces IL31 signaling function in a companion animal species, as measured by a reduction in STAT-3 phosphorylation.

Embodiment 5. The antibody of embodiment 4, wherein the companion animal species is canine or feline.

Embodiment 6. The antibody of any one of the preceding embodiments, wherein the antibody binds to canine IL31 or feline IL31 as determined by immunoblot analysis and/or biolayer interferometry.

Embodiment 7. The antibody of any one of the preceding embodiments, wherein the antibody competes with monoclonal M14 antibody in binding to canine IL31.

Embodiment 8. The antibody of any one of the preceding embodiments, wherein the antibody competes with monoclonal M14 antibody in binding to feline IL31.

Embodiment 9. The antibody of any one of the preceding embodiments, wherein the antibody does not bind to human IL31 as determined by immunoblot analysis and/or biolayer interferometry.

Embodiment 10. The antibody of any one of the preceding embodiments, wherein the antibody is a monoclonal antibody.

Embodiment 11. The antibody of any one of the preceding embodiments, wherein the antibody is a caninized, a felinized, or a chimeric antibody.

Embodiment 12. The antibody of any one of the preceding embodiments, further comprising one or more of (a) a variable region heavy chain framework 1 (HC-FR1) sequence of SEQ ID NO: 16; (b) a HC-FR2 sequence of SEQ ID NO: 17; (c) a HC-FR3 sequence of SEQ ID NO: 18; (d) a HC-FR4 sequence of SEQ ID NO: 19; (e) a variable region light chain framework 1 (LC-FR1) sequence of SEQ ID NO: 25; (0 an LC-FR2 sequence of SEQ ID NO: 26; (g) an LC-FR3 sequence of SEQ ID NO: 27; or (h) an LC-FR4 sequence of SEQ ID NO: 28.

Embodiment 13. The antibody of any one embodiments 1 to 11, further comprising one or more of (a) a variable region heavy chain framework 1 (HC-FR1) sequence of SEQ ID NO: 55 or SEQ ID NO: 56; (b) a HC-FR2 sequence of SEQ ID NO: 57, SEQ ID NO: 58, SEQ ID NO: 59; (c) a HC-FR3 sequence of SEQ ID NO: 60 or SEQ ID NO: 61; (d) a HC-FR4 sequence of SEQ ID NO: 62 or SEQ ID NO: 63; (e) a variable region light chain framework 1 (LC-FR1) sequence of SEQ ID NO: 64 or SEQ ID NO: 65; (0 an LC-FR2 sequence of SEQ ID NO: 66, SEQ ID NO: 67, or SEQ ID NO: 68; (g) an LC-FR3 sequence of SEQ ID NO: 69 or SEQ ID NO: 70; or (h) an LC-FR4 sequence of SEQ ID NO: 71 or SEQ ID NO: 72.

Embodiment 14. The antibody of any one of the preceding embodiments, wherein the antibody comprises:
  a) (i) a variable heavy chain sequence having at least 85%, at least 90%, at least 95%, at least 97%, at least 98%, or at least 99% sequence identity to the amino acid sequence of SEQ ID NO: 5, SEQ ID NO: 6, or SEQ ID NO: 7; (ii) a variable light chain sequence having at least 85%, at least 90%, at least 95%, at least 97%, at least 98%, or at least 99% sequence identity to the amino acid sequence of SEQ ID NO: 8, SEQ ID NO: 9, or SEQ ID NO: 10; or (iii) a variable heavy chain sequence as in (i) and a variable light chain sequence as in (ii); or b) (i) a variable heavy chain sequence having at least 85%, at least 90%, at least 95%, at least 97%, at least 98%, or at least 99% sequence identity to the amino acid sequence of SEQ ID NO: 49, SEQ ID NO: 50, SEQ ID NO: 51, or SEQ ID NO: 90; (ii) a variable light chain sequence having at least 85%, at least 90%, at least 95%, at least 98%, or at least 99% sequence identity to the amino acid sequence of SEQ ID NO: 52, SEQ ID NO: 53, or SEQ ID NO: 54; or (iii) a variable heavy chain sequence as in (i) and a variable light chain sequence as in (ii).

Embodiment 15. The antibody of any one of the preceding embodiments, wherein the antibody comprises a variable heavy chain sequence of SEQ ID NO: 5, SEQ ID NO: 6, SEQ ID NO: 7, SEQ ID NO: 49, SEQ ID NO: 50, SEQ ID NO: 51, or SEQ ID NO: 90.

Embodiment 16. The antibody of any one of the preceding embodiments, wherein the antibody comprises a variable light chain sequence of SEQ ID NO: 8, SEQ ID NO: 9, SEQ ID NO: 10, SEQ ID NO: 52, SEQ ID NO: 53, or SEQ ID NO: 54.

Embodiment 17. The antibody of any one of the preceding embodiments, wherein the antibody comprises:

a) a variable heavy chain sequence of SEQ ID NO:5, SEQ ID NO: 7, or SEQ ID NO: 8; and a variable light chain sequence of SEQ ID NO: 9, SEQ ID NO: 10, or SEQ ID NO: 11; or b) a variable heavy chain sequence of SEQ ID NO: 49, SEQ ID NO: 50, SEQ ID NO: 51, or SEQ ID NO: 90; and a variable light chain sequence of SEQ ID NO: 52, SEQ ID NO: 53, or SEQ ID NO: 54.

Embodiment 18. The antibody of any one of the preceding embodiments, wherein the antibody comprises a canine or feline constant heavy chain region and/or a canine or feline constant light chain region.

Embodiment 19. The antibody of any one of the preceding embodiments, wherein the antibody comprises (a) a canine heavy chain constant region selected from an IgG-A, IgG-B, IgG-C, and IgG-D constant region; or (b) a feline heavy chain constant region selected from an IgG1, IgG2a, and IgG2b constant region.

Embodiment 20. The antibody of any one of the preceding embodiments, wherein the antibody comprises:

a) (i) a heavy chain amino acid sequence of SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, or SEQ ID NO: 45; (ii) a light chain amino acid sequence of SEQ ID NO: 46, SEQ ID NO: 47, or SEQ ID NO: 48; or (iii) a heavy chain amino acid sequence as in (i) and a light chain amino acid sequence as in (ii); or b) (i) a heavy chain amino acid sequence of SEQ ID NO: 73, SEQ ID NO: 74, SEQ ID NO: 75, or SEQ ID NO: 91; (ii) a light chain amino acid sequence of SEQ ID NO: 76, SEQ ID NO: 77, or SEQ ID NO: 78; or (iii) a heavy chain amino acid sequence as in (i) and a light chain amino acid sequence as in (ii).

Embodiment 21. An isolated antibody comprising a variable heavy chain amino acid sequence of SEQ ID NO: 3 and/or a variable light chain amino acid sequence of SEQ ID NO: 4.

Embodiment 22. An isolated antibody comprising a variable heavy chain amino acid sequence of SEQ ID NO: 5, SEQ ID NO: 6, or SEQ ID NO: 7.

Embodiment 23. An isolated antibody comprising a variable light chain amino acid sequence of SEQ ID NO: 8, SEQ ID NO: 9, or SEQ ID NO: 10.

Embodiment 24. The isolated antibody of embodiment 21, wherein the antibody comprises a variable light chain amino acid sequence of SEQ ID NO: 8, SEQ ID NO: 9, or SEQ ID NO: 10.

Embodiment 25. An isolated antibody comprising a variable heavy chain amino acid sequence of SEQ ID NO: 49, SEQ ID NO: 50, SEQ ID NO: 51, or SEQ ID NO: 90.

Embodiment 26. An isolated antibody comprising a variable light chain amino acid sequence of SEQ ID NO: 52, SEQ ID NO: 53, or SEQ ID NO: 54.

Embodiment 27. The isolated antibody of any one of embodiments 1 to 25, wherein the antibody comprises a variable light chain amino acid sequence of SEQ ID NO: 52, SEQ ID NO: 53, or SEQ ID NO: 54.

Embodiment 28. The antibody of any one of the preceding embodiments, wherein the antibody is an antibody fragment selected from Fv, scFv, Fab, Fab', F(ab')$_2$, and Fab'-SH.

Embodiment 29. The antibody of any one of the preceding embodiments, wherein the antibody is bi-specific, wherein the antibody binds to IL31 and one or more antigens selected from IL17, TNFα, CD20, CD19, CD25, IL4, IL13, IL23, IgE, CD11α, IL6R, α4-Intergrin, IL12, IL1β, or BlyS.

Embodiment 30. An isolated nucleic acid encoding the antibody of any one of embodiments 1 to 29.

Embodiment 31. A host cell comprising the nucleic acid of embodiment 30.

Embodiment 32. A method of producing an antibody comprising culturing the host cell of embodiment 31 and isolating the antibody.

Embodiment 33. A pharmaceutical composition comprising the antibody of any one of embodiments 1 to 29 and a pharmaceutically acceptable carrier.

Embodiment 34. A method of treating a companion animal species having an IL31-induced condition, the method comprising administering to the companion animal species a therapeutically effective amount of the antibody of any one of embodiments 1 to 29 or the pharmaceutical composition of embodiment 33.

Embodiment 35. The method of embodiment 33, wherein the companion animal species is a canine or a feline.

Embodiment 36. The method of embodiment 34 or embodiment 35, wherein the IL31-induced condition is a pruritic or allergic condition.

Embodiment 37. The method of any one of embodiment 34 to 36, wherein the IL31-induced condition is selected from atopic dermatitis, allergic dermatitis, pruritus, asthma, psoriasis, scleroderma and eczema.

Embodiment 38. The method of any one of embodiments 34 to 37, wherein the antibody or the pharmaceutical composition is administered parenterally.

Embodiment 39. The method of any one of embodiments 34 to 38, wherein the antibody or the pharmaceutical composition is administered by an intramuscular route, an intraperitoneal route, an intracerebrospinal route, a subcutaneous route, an intra-arterial route, an intrasynovial route, an intrathecal route, or an inhalation route.

Embodiment 40. The method of any one of embodiments 34 to 39, wherein the method comprises administering in combination with the antibody or the pharmaceutical composition a Jak inhibitor, a PI3K inhibitor, an AKT inhibitor, or a MAPK inhibitor.

Embodiment 41. The method of any one of embodiments 34 to 40, wherein the method comprises administering in combination with the antibody or the pharmaceutical composition one or more antibodies selected from an anti-IL17 antibody, an anti-TNFα antibody, an anti-CD20 antibody, an anti-CD19 antibody, an anti-CD25 antibody, an anti-IL4 antibody, an anti-IL13 antibody, an anti-IL23 antibody, an anti-IgE antibody, an anti-CD11a antibody, anti-IL6R antibody, anti-α4-Intergrin antibody, an anti-IL12 antibody, an anti-IL1βantibody, and an anti-BlyS antibody.

Embodiment 42. A method of reducing IL31 signaling function in a cell, the method comprising exposing to the cell the antibody of any one of embodiments 1 to 29 or the pharmaceutical composition of embodiment 33 under conditions permissive for binding of the antibody to extracellular IL31, thereby reducing binding to IL31 receptor and/or reducing IL31 signaling function by the cell.

Embodiment 43. The method of embodiment 42, wherein the cell is exposed to the antibody or the pharmaceutical composition ex vivo.

Embodiment 44. The method of embodiment 42, wherein the cell is exposed to the antibody or the pharmaceutical composition in vivo.

Embodiment 45. The method of any one of embodiments 42 to 44, wherein the cell is a canine cell or a feline cell.

Embodiment 46. A method for detecting IL31 in a sample from a companion animal species comprising contacting the sample with the antibody of any one of embodiments 1 to 29 or the pharmaceutical composition of embodiment 33 under conditions permissive for binding of the antibody to IL31, and detecting whether a complex is formed between the antibody and IL31 in the sample.

Embodiment 47. The method of embodiment 46, wherein the sample is a biological sample obtained from a canine or a feline.

Embodiment 48. A method of identifying an IL31 antagonist comprising contacting an engineered cell line with an IL31 antagonist candidate, wherein the engineered cell line is a mammalian cell line that is not derived from a canine or feline, and wherein the engineered cell line expresses canine IL31Ra and/or feline IL31Ra.

Embodiment 49. The method of embodiment 48, wherein the engineered cell line is a HeLa cell line.

Embodiment 50. The method of embodiment 48 or 49, wherein the engineered cell line expresses canine IL31Ra or feline IL31Ra.

Embodiment 51. The method of any one of embodiments 48 to 50, wherein the engineered cell line expresses a polypeptide having the amino acid sequence of SEQ ID NO: 92 or SEQ ID NO: 93.

Embodiment 52. The method of any one of embodiments 48 to 51, wherein the engineered cell line does not express canine or feline Oncostatin M receptor (OSMR).

Embodiment 53. The method of any one of embodiments 48 to 52, wherein the IL31 antagonist candidate is an IL31 antibody, a soluble IL31 receptor, an IL31Ra antibody, or a small molecule, an aptamer, or a peptide.

Embodiment 54. The method of any one of embodiments 48 to 53, wherein the method comprises measuring IL31 signaling functioning.

Embodiment 55. The method of embodiment 54, wherein the IL31 signaling function is measured by level of STAT-1, STAT-3, and/or STAT-5 phosphorylation.

Embodiment 56. The method of embodiments 48 to 55, wherein the IL31 antagonist candidate is identified by detecting a reduction in STAT-1, STAT-3, and/or STAT-5 phosphorylation.

BRIEF DESCRIPTION OF THE DRAWINGS

FIG. 1 is a binding analysis of six chimeric antibodies to feline IL-31 according to Example 2.

DESCRIPTION OF CERTAIN SEQUENCES

Table 1 provides a listing of certain sequences referenced herein.

TABLE 1

| | Description of Certain Sequences | |
| --- | --- | --- |
| SEQ ID NO: | SEQUENCE | DESCRIPTION |
| 1 | DIVLTQSPASLAVSLGQRATISCRASESVDTYGNSFM HWYQQKSGQSPKLLIYRASNLESGIPARFGGSGSRTD FTLTIDPVEADDVATYYCQQSYEDPWTFGGGTKLEIK | Variable light chain amino acid sequence of mouse antibody clone M14 |
| 2 | EVQLQESGPSLVKPSQTLSLTCSVTGDSLTSGYWNWI RKFPGNKLEYMGYISYSGETDYNPSLKSRISITRDTS KNQYYLQLNSVTTEDTATYYCARYGNYGYAMDYWGQG TSVTVSS | Variable heavy chain amino acid sequence of mouse antibody clone M14 |
| 3 | EVQLVESGPSLVKPGGSLRLTCSVTGDSITSGYWNWI RKFPGNKLEYMGYISYSGITDYNPSLKSRITISRDTS KNQYYLQLNSVTTEDTATYYCARYGNYGYAMDYWGQG TSVTVSS | Exemplary caninized variable heavy chain amino acid sequence of mouse antibody clone M14 |
| 4 | DIVMTQSPASLSVSLGQRATISCRASESVDTYGNSFM HWYQQKPGQSPKLLIYRASNLESGIPARFGGSGSGTD FTLTIDPVQADDVATYYCQQSYEDPWTFGGGTKLEIK | Exemplary caninized variable light chain amino acid sequence of mouse antibody clone M14 |
| 5 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYGNYGYAMDYWGQG TSVTVSS | Exemplary caninized, matured variable heavy chain sequence "cmVH1" N35K |

TABLE 1-continued

Description of Certain Sequences

| SEQ ID NO: | SEQUENCE | DESCRIPTION |
|---|---|---|
| 6 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYPNYGYAMDYWGQG TSVTVSS | Exemplary caninized, matured variable heavy chain sequence "cmVH2" N35K G99P |
| 7 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYANYGYAMDYWGQG TSVTVSS | Exemplary caninized, matured variable heavy chain sequence "cmVH3" N35K G99A |
| 8 | DIVMTQSPASLSVSLGQRATISCRASESVDTYGRSFM HWYQQKPGQSPKLLIYRASNLESGIPARFGGSGSGTD FTLTIDPVQADDVATYYCQQSYEDPWTFGGGTKLEIK | Exemplary caninized, matured variable light chain sequence "cmVL1" N34R |
| 9 | DIVMTQSPASLSVSLGQRATISCRASESVDTYGRSFM HWYQQKPGQSPKLLIYRASNLESGIPARFGGSGSGTD FTLTIDPVQADDVATYYCYQSYEDPWTFGGGTKLEIK | Exemplary caninized, matured variable light chain sequence "cmVL2" N34R Q93Y |
| 10 | DIVMTQSPASLSVSLGQRATISCRASESVDTYGRSFM HWYQQKPGQSPKLLIYRASNLESGIPARFGGSGSGTD FTLTIDPVQADDVATYYCHQSYEDPWTFGGGTKLEIK | Exemplary caninized, matured variable light chain sequence "cmVL3" N34R Q93H |
| 11 | GDSITSGYW | CDR-H1 of cmVH1, cmVH2, and cmVH3 |
| 12 | YISYSGITDY | CDR-H2 of cmVH1, cmVH2, and cmVH3 |
| 13 | ARYGNYGYAMDY | CDR-H3 of cmVH1 |
| 14 | ARYPNYGYAMDY | CDR-H3 of cmVH2 |
| 15 | ARYANYGYAMDY | CDR-H3 of cmVH3 |
| 16 | EVQLQESGPSLVKPSQTLSLTCSVT | HC-FR1 of cmVH1, cmVH2, and cmVH3 |
| 17 | KWIRKFPGNKLEYMG | HC-FR2 of cmVH1, cmVH2, and cmVH3 |
| 18 | NPSLKSRISITRDTSKNQYYLQLNSVTTEDTATYYC | HC-FR3 of cmVH1, cmVH2, and cmVH3 |
| 19 | WGQGTSVTVSS | HC-FR4 of cmVH1, cmVH2, and cmVH3 |
| 20 | RASESVDTYGRSFMH | CDR-L1 of cmVL1, cmVL2, and cmVL3 |
| 21 | RASNLES | CDR-L2of cmVL1, cmVL2, and cmVL3 |
| 22 | QQSYEDPWT | CDR-L3of cmVL1 |
| 23 | YQSYEDPWT | CDR-L3 of cmVL2 |
| 24 | HQSYEDPWT | CDR-L3 of cmVL3 |
| 25 | DIVLTQSPASLAVSLGQRATISC | LC-FRI of cmVL1, cmVL2, and cmVL3 |
| 26 | WYQQKSGQSPKLLIY | LC-FR2 of cmVL1, cmVL2, and cmVL3 |
| 27 | GIPARFGGSGSRTDFTLTIDPVEADDVATYYC | LC-FR3 of cmVL1, cmVL2, and cmVL3 |

TABLE 1-continued

Description of Certain Sequences

| SEQ ID NO: | SEQUENCE | DESCRIPTION |
|---|---|---|
| 28 | FGGGTKLEIK | LC-FR4 of cmVL1, cmVL2, and cmVL3 |
| 29 | EVQLVESGPSLVKPGGSLRLTCSVTGDSITSGYWNWI RKFPGNKLEYMGYISYSGITDYNPSLKSRITISRDTS KNQYYLQLNSVTTEDTATYYCARYGNYGYAMDYWGQG TSVTVSSASTTAPSVFPLAPSCGSTSGSTVALACLVS GYFPEPVTVSWNSGSLTSGVHTFPSVLQSSGLHSLSS MVTVPSSRWPSETFTCNVVHPASNTKVDKPVFNECRC TDTPCPVPEPLGGPSVLIFPPKPKDILRITRTPEVTC VVLDLGREDPEVQISWFVDGKEVHTAKTQSREQQFNG TYRVVSVLPIEHQDWLTGKEFKCRVNHIDLPSPIERT ISKARGRAHKPSVYVLPPSPKELSSSDTVSITCLIKD FYPPDIDVEWQSNGQQEPERKHRMTPPQLDEDGSYFL YSKLSVDKSRWQQGDPFTCAVMHETLQNHYTDLSLSH SPGK | Exemplary caninized variable heavy chain sequence from mouse antibody clone M14 and canine IgG-A |
| 30 | EVQLVESGPSLVKPGGSLRLTCSVTGDSITSGYWNWI RKFPGNKLEYMGYISYSGITDYNPSLKSRITISRDTS KNQYYLQLNSVTTEDTATYYCARYGNYGYAMDYWGQG TSVTVSSASTTAPSVFPLAPSCGSTSGSTVALACLVS GYFPEPVTVSWNSGSLTSGVHTFPSVLQSSGLYSLSS MVTVPSSRWPSETFTCNVAHPASKTKVDKPVPKRENG RVPRPPDCPKCPAPEMLGGPSVFIFPPKPKDTLLIAR TPEVTCVVVDLDPEDPEVQISWFVDGKQMQTAKTQPR EEQFNGTYRVVSVLPIGHQDWLKGKQFTCKVNNKALP SPIERTISKARGQAHQPSVYVLPPSREELSKNTVSLT CLIKDFFPPDIDVEWQSNGQQEPESKYRTTPPQLDED GSYFLYSKLSVDKSRWQRGDTFICAVMHEALHNHYTQ ESLSHSPGK | Exemplary caninized variable heavy chain sequence from mouse antibody clone M14 and canine IgG-B |
| 31 | EVQLVESGPSLVKPGGSLRLTCSVTGDSITSGYWNWI RKFPGNKLEYMGYISYSGITDYNPSLKSRITISRDTS KNQYYLQLNSVTTEDTATYYCARYGNYGYAMDYWGQG TSVTVSSASTTAPSVFPLAPSCGSQSGSTVALACLVS GYIPEPVTVSWNSVSLTSGVHTFPSVLQSSGLYSLSS MVTVPSSRWPSETFTCNVAHPATNTKVDKPVAKECEC KCNCNNCPCPGCGLLGGPSVFIFPPKPKDILVTARTP TVTCVVVDLDPENPEVQISWFVDSKQVQTANTQPREE QSNGTYRVVSVLPIGHQDWLSGKQFKCKVNNKALPSP IEEIISKTPGQAHQPNVYVLPPSRDEMSKNTVTLTCL VKDFFPPEIDVEWQSNGQQEPESKYRMTPPQLDEDGS YFLYSKLSVDKSRWQRGDTFICAVMHEALHNHYTQIS LSHSPGK | Exemplary caninized variable heavy chain sequence from mouse antibody clone M14 and canine IgG-C |
| 32 | EVQLVESGPSLVKPGGSLRLTCSVTGDSITSGYWNWI RKFPGNKLEYMGYISYSGITDYNPSLKSRITISRDTS KNQYYLQLNSVTTEDTATYYCARYGNYGYAMDYWGQG TSVTVSSASTTAPSVFPLAPSCGSTSGSTVALACLVS GYFPEPVTVSWNSGSLTSGVHTFPSVLQSSGLYSLSS TVTVPSSRWPSETFTCNVVHPASNTKVDKPVPKESTC KCISPCPVPESLGGPSVFIFPPKPKDILRITRTPEIT CVVLDLGREDPEVQISWFVDGKEVHTAKTQPREQQFN STYRVVSVLPIEHQDWLTGKEFKCRVNHIGLPSPIER TISKARGQAHQPSVYVLPPSPKELSSSDTVTLTCLIK DFFPPEIDVEWQSNGQPEPESKYHTTAPQLDEDGSYF LYSKLSVDKSRWQQGDTFTCAVMHEALQNHYTDLSLS HSPGK | Exemplary caninized variable heavy chain sequence from mouse antibody clone M14 and canine IgG-D |
| 33 | DIVMTQSPASLSVSLGQRATISCRASESVDTYGNSFM HWYQQKPGQSPKLLIYRASNLESGIPARFGGSGSGTD FTLTIDPVQADDVATYYCQQSYEDPWTFGGGTKLEIK RNDAQPAVYLFQPSPDQLHTGSASVVCLLNSFYPKDI NVKWKVDGVIQDTGIQESVTEQDKDSTYSLSSTLTMS STEYLSHELYSCEITHKSLPSTLIKSFQRSECQRVD | Exemplary caninized variable light chain sequence from mouse antibody clone M14 and canine light chain constant region |
| 34 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYGNYGYAMDYWGQG TSVTVSSASTTAPSVFPLAPSCGSTSGSTVALACLVS GYFPEPVTVSWNSGSLTSGVHTFPSVLQSSGLHSLSS MVTVPSSRWPSETFTCNVVHPASNTKVDKPVFNECRC TDTPCPVPEPLGGPSVLIFPPKPKDILRITRTPEVTC VVLDLGREDPEVQISWFVDGKEVHTAKTQSREQQFNG TYRVVSVLPIEHQDWLTGKEFKCRVNHIDLPSPIERT | Exemplary caninized, matured variable heavy chain sequence cmVH1 and canine IgG-A |

TABLE 1-continued

Description of Certain Sequences

| SEQ ID NO: | SEQUENCE | DESCRIPTION |
|---|---|---|
| | ISKARGRAHKPSVYVLPPSPKELSSSDTVSITCLIKD FYPPDIDVEWQSNGQQEPERKHRMTPPQLDEDGSYFL YSKLSVDKSRWQQGDPFTCAVMHETLQNHYTDLSLSH SPGK | |
| 35 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYGNYGYAMDYWGQG TSVTVSSASTTAPSVFPLAPSCGSTSGSTVALACLVS GYFPEPVTVSWNSGSLTSGVHTFPSVLQSSGLYSLSS MVTVPSSRWPSETFTCNVAHPASKTKVDKPVPKRENG RVPRPPDCPKCPAPEMLGGPSVFIFPPKPKDTLLIAR TPEVTCVVVDLDPEDPEVQISWFVDGKQMQTAKTQPR EEQFNGTYRVVSVLPIGHQDWLKGKQFTCKVNNKALP SPIERTISKARGQAHQPSVYVLPPSREELSKNTVSLT CLIKDFFPPDIDVEWQSNGQQEPESKYRTTPPQLDED GSYFLYSKLSVDKSRWQRGDTFICAVMHEALHNHYTQ ESLSHSPGK | Exemplary caninized, matured variable heavy chain sequence cmVH1 and canine IgG-B |
| 36 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYGNYGYAMDYWGQG TSVTVSSASTTAPSVFPLAPSCGSQSGSTVALACLVS GYIPEPVTVSWNSVSLTSGVHTFPSVLQSSGLYSLSS MVTVPSSRWPSETFTCNVAHPATNTKVDKPVAKECEC KCNCNNCPCPGCGLLGGPSVFIFPPKPKDILVTARTP TVTCVVVDLDPENPEVQISWFVDSKQVQTANTQPREE QSNGTYRVVSVLPIGHQDWLSGKQFKCKVNNKALPSP IEEIISKTPGQAHQPNVYVLPPSRDEMSKNTVTLTCL VKDFFPPEIDVEWQSNGQQEPESKYRMTPPQLDEDGS YFLYSKLSVDKSRWQRGDTFICAVMHEALHNHYTQIS LSHSPGK | Exemplary caninized, matured variable heavy chain sequence cmVH1 and canine IgG-C |
| 37 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYGNYGYAMDYWGQG TSVTVSSASTTAPSVFPLAPSCGSTSGSTVALACLVS GYFPEPVTVSWNSGSLTSGVHTFPSVLQSSGLYSLSS TVTVPSSRWPSETFTCNVVHPASNTKVDKPVPKESTC KCISPCPVPESLGGPSVFIFPPKPKDILRITRTPEIT CVVLDLGREDPEVQISWFVDGKEVHTAKTQPREQQFN STYRVVSVLPIEHQDWLTGKEFKCRVNHIGLPSPIER TISKARGQAHQPSVYVLPPSPKELSSSDTVTLTCLIK DFFPPEIDVEWQSNGQPEPESKYHTTAPQLDEDGSYF LYSKLSVDKSRWQQGDTFTCAVMHEALQNHYTDLSLS HSPGK | Exemplary caninized, matured variable heavy chain sequence cmVH1 and canine IgG-D |
| 38 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYPNYGYAMDYWGQG TSVTVSSASTTAPSVFPLAPSCGSTSGSTVALACLVS GYFPEPVTVSWNSGSLTSGVHTFPSVLQSSGLHSLSS MVTVPSSRWPSETFTCNVVHPASNTKVDKPVFNECRC TDTPCPVPEPLGGPSVLIFPPKPKDILRITRTPEVTC VVLDLGREDPEVQISWFVDGKEVHTAKTQSREQQFNG TYRVVSVLPIEHQDWLTGKEFKCRVNHIDLPSPIERT ISKARGRAHKPSVYVLPPSPKELSSSDTVSITCLIKD FYPPDIDVEWQSNGQQEPERKHRMTPPQLDEDGSYFL YSKLSVDKSRWQQGDPFTCAVMHETLQNHYTDLSLSH SPGK | Exemplary caninized, matured variable heavy chain sequence cmVH2 and canine IgG-A |
| 39 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYPNYGYAMDYWGQG TSVTVSSASTTAPSVFPLAPSCGSTSGSTVALACLVS GYFPEPVTVSWNSGSLTSGVHTFPSVLQSSGLYSLSS MVTVPSSRWPSETFTCNVAHPASKTKVDKPVPKRENG RVPRPPDCPKCPAPEMLGGPSVFIFPPKPKDTLLIAR TPEVTCVVVDLDPEDPEVQISWFVDGKQMQTAKTQPR EEQFNGTYRVVSVLPIGHQDWLKGKQFTCKVNNKALP SPIERTISKARGQAHQPSVYVLPPSREELSKNTVSLT CLIKDFFPPDIDVEWQSNGQQEPESKYRTTPPQLDED GSYFLYSKLSVDKSRWQRGDTFICAVMHEALHNHYTQ ESLSHSPGK | Exemplary caninized, matured variable heavy chain sequence cmVH2 and canine IgG-B |

TABLE 1-continued

Description of Certain Sequences

| SEQ ID NO: | SEQUENCE | DESCRIPTION |
|---|---|---|
| 40 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYPNYGYAMDYWGQG TSVTVSSASTTAPSVFPLAPSCGSQSGSTVALACLVS GYIPEPVTVSWNSVSLTSGVHTFPSVLQSSGLYSLSS MVTVPSSRWPSETFTCNVAHPATNTKVDKPVAKECEC KCNCNNCPCPGCGLLGGPSVFIFPPKPKDILVTARTP TVTCVVVDLDPENPEVQISWFVDSKQVQTANTQPREE QSNGTYRVVSVLPIGHQDWLSGKQFKCKVNNKALPSP IEEIISKTPGQAHQPNVYVLPPSRDEMSKNTVTLTCL VKDFFPPEIDVEWQSNGQQEPESKYRMTPPQLDEDGS YFLYSKLSVDKSRWQRGDTFICAVMHEALHNHYTQIS LSHSPGK | Exemplary caninized, matured variable heavy chain sequence cmVH2 and canine IgG-C |
| 41 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYPNYGYAMDYWGQG TSVTVSSASTTAPSVFPLAPSCGSTSGSTVALACLVS GYFPEPVTVSWNSGSLTSGVHTFPSVLQSSGLYSLSS TVTVPSSRWPSETFTCNVVHPASNTKVDKPVPKESTC KCISPCPVPESLGGPSVFIFPPKPKDILRITRTPEIT CVVLDLGREDPEVQISWFVDGKEVHTAKTQPREQQFN STYRVVSVLPIEHQDWLTGKEFKCRVNHIGLPSPIER TISKARGQAHQPSVYVLPPSPKELSSSDTVTLTCLIK DFFPPEIDVEWQSNGQPEPESKYHTTAPQLDEDGSYF LYSKLSVDKSRWQQGDTFTCAVMHEALQNHYTDLSLS HSPGK | Exemplary caninized, matured variable heavy chain sequence cmVH2 and canine IgG-D |
| 42 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYANYGYAMDYWGQG TSVTVSSASTTAPSVFPLAPSCGSTSGSTVALACLVS GYFPEPVTVSWNSGSLTSGVHTFPSVLQSSGLHSLSS MVTVPSSRWPSETFTCNVVHPASNTKVDKPVFNECRC TDTPCPVPEPLGGPSVLIFPPKPKDILRITRTPEVTC VVLDLGREDPEVQISWFVDGKEVHTAKTQSREQQFNG TYRVVSVLPIEHQDWLTGKEFKCRVNHIDLPSPIERT ISKARGRAHKPSVYVLPPSPKELSSSDTVSITCLIKD FYPPDIDVEWQSNGQQEPERKHRMTPPQLDEDGSYFL YSKLSVDKSRWQQGDPFTCAVMHETLQNHYTDLSLSH SPGK | Exemplary caninized, matured variable heavy chain sequence cmVH3 and canine IgG-A |
| 43 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYANYGYAMDYWGQG TSVTVSSASTTAPSVFPLAPSCGSTSGSTVALACLVS GYFPEPVTVSWNSGSLTSGVHTFPSVLQSSGLYSLSS MVTVPSSRWPSETFTCNVAHPASKTKVDKPVPKRENG RVPRPPDCPKCPAPEMLGGPSVFIFPPKPKDTLLIAR TPEVTCVVVDLDPEDPEVQISWFVDGKQMQTAKTQPR EEQFNGTYRVVSVLPIGHQDWLKGKQFTCKVNNKALP SPIERTISKARGQAHQPSVYVLPPSREELSKNTVSLT CLIKDFFPPDIDVEWQSNGQQEPESKYRTTPPQLDED GSYFLYSKLSVDKSRWQRGDTFICAVMHEALHNHYTQ ESLSHSPGK | Exemplary caninized, matured variable heavy chain sequence cmVH3 and canine IgG-B |
| 44 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYANYGYAMDYWGQG TSVTVSSASTTAPSVFPLAPSCGSQSGSTVALACLVS GYIPEPVTVSWNSVSLTSGVHTFPSVLQSSGLYSLSS MVTVPSSRWPSETFTCNVAHPATNTKVDKPVAKECEC KCNCNNCPCPGCGLLGGPSVFIFPPKPKDILVTARTP TVTCVVVDLDPENPEVQISWFVDSKQVQTANTQPREE QSNGTYRVVSVLPIGHQDWLSGKQFKCKVNNKALPSP IEEIISKTPGQAHQPNVYVLPPSRDEMSKNTVTLTCL VKDFFPPEIDVEWQSNGQQEPESKYRMTPPQLDEDGS YFLYSKLSVDKSRWQRGDTFICAVMHEALHNHYTQIS LSHSPGK | Exemplary caninized, matured variable heavy chain sequence cmVH3 and canine IgG-C |
| 45 | EVQLVESGPSLVKPGGSLRLTCSVTGDSITSGYWKWI RKFPGNKLEYMGYISYSGITDYNPSLKSRITISRDTS KNQYYLQLNSVTTEDTATYYCARYANYGYAMDYWGQG TSVTVSSASTTAPSVFPLAPSCGSTSGSTVALACLVS GYFPEPVTVSWNSGSLTSGVHTFPSVLQSSGLYSLSS | Exemplary caninized, matured variable heavy chain sequence cmVH3 and canine IgG-D |

TABLE 1-continued

Description of Certain Sequences

| SEQ ID NO: | SEQUENCE | DESCRIPTION |
|---|---|---|
| | TVTVPSSRWPSETFTCNVVHPASNTKVDKPVPKESTC KCISPCPVPESLGGPSVFIFPPKPKDILRITRTPEIT CVVLDLGREDPEVQISWFVDGKEVHTAKTQPREQQFN STYRVVSVLPIEHQDWLTGKEFKCRVNHIGLPSPIER TISKARGQAHQPSVYVLPPSPKELSSSDTVTLTCLIK DFFPPEIDVEWQSNGQPEPESKYHTTAPQLDEDGSYF LYSKLSVDKSRWQQGDTFTCAVMHEALQNHYTDLSLS HSPGK | |
| 46 | DIVMTQSPASLSVSLGQRATISCRASESVDTYGRSFM HWYQQKPGQSPKLLIYRASNLESGIPARFGGSGSGTD FTLTIDPVQADDVATYYCQQSYEDPWTFGGGTKLEIK RNDAQPAVYLFQPSPDQLHTGSASVVCLLNSFYPKDI NVKWKVDGVIQDTGIQESVTEQDKDSTYSLSSTLTMS STEYLSHELYSCEITHKSLPSTLIKSFQRSECQRVD | Exemplary caninized, matured variable light chain sequence cmVL1 and canine light chain constant region |
| 47 | DIVMTQSPASLSVSLGQRATISCRASESVDTYGRSFM HWYQQKPGQSPKLLIYRASNLESGIPARFGGSGSGTD FTLTIDPVQADDVATYYCYQSYEDPWTFGGGTKLEIK RNDAQPAVYLFQPSPDQLHTGSASVVCLLNSFYPKDI NVKWKVDGVIQDTGIQESVTEQDKDSTYSLSSTLTMS STEYLSHELYSCEITHKSLPSTLIKSFQRSECQRVD | Exemplary caninized, matured variable light chain sequence cmVL1 and canine light chain constant region |
| 48 | DIVMTQSPASLSVSLGQRATISCRASESVDTYGRSFM HWYQQKPGQSPKLLIYRASNLESGIPARFGGSGSGTD FTLTIDPVQADDVATYYCHQSYEDPWTFGGGTKLEIK RNDAQPAVYLFQPSPDQLHTGSASVVCLLNSFYPKDI NVKWKVDGVIQDTGIQESVTEQDKDSTYSLSSTLTMS STEYLSHELYSCEITHKSLPSTLIKSFQRSECQRVD | Exemplary caninized, matured variable light chain sequence cmVL1 and canine light chain constant region |
| 49 | QLTLRESGPGLVKPSQSLSLTCSVTGDSITSGYWKWI RQRPGRGLEWLGYISYSGITDYNPSLKSRISITADTA QNQFSLQLSSMTTEDTAVYYCARYANYGYAMDYWGPG ALVTVSS | Exemplary felinized, matured variable heavy chain sequence "fmVH3a" N35K G99A |
| 50 | DVQLVESGGDLVKPGGSLRLTCSVTGDSITSGYWKWV RQAPGKGLQWVAYISYSGITDYNPSLKSRFTISRDNA KNTLYLQMNSLKTEDTATYYCARYANYGYAMDYWGQG ALVTVSS | Exemplary felinized, matured variable heavy chain sequence "fmVH3b" N35K G99A |
| 51 | DVQLVESGGDLVKPGGSLRLTCSVTGDSITSGYWKWI RKFPGNKLEYMGYISYSGITDYNPSLKSRFTISRDNA KNTLYLQMNSLKTEDTATYYCARYANYGYAMDYWGQG ALVTVSS | Exemplary felinized, matured variable heavy chain sequence "fmVH3c" N35K G99A |
| 90 | QLTLRESGPGLVKPSQSLSLTCSVTGDSITSGYWKWI RQRPGNKLEYMGYISYSGITDYNPAFQGRISITADTA QNQFSLQLSSMTTEDTAVYYCARYPNYGYAMDYWGPG TLVTVSS | Exemplary felinized, matured variable heavy chain sequence "fmVH2" N35K G99P |
| 52 | DIVMTQTPLSLSVTPGEPASISCRASESVDTYGRSFM HWYLQKPGQSPRRLIYRASNLESGVPDRFSGSGSGTD FTLRISRVEADDVGVYYCHQSYEDPWTFGPGTKLEIK | Exemplary felinized, matured variable light chain sequence "fmVL3a" N34R Q93H |
| 53 | DVVMTQTPLSLPVTPGEPASISCRASESVDTYGRSFM HWYLQKPGQSPRLLIYRASNLESGVPDRFSGSGSGTD FTLRISRVEADDVATYYCHQSYEDPWTFGQGTKLEVK | Exemplary felinized, matured variable light chain sequence "fmVL3b" N34R Q93H |
| 54 | DIVMTQTPLSLSVTPGEPASISCRASESVDTYGRSFM HWYQQKPGQSPKLLIYRASNLESGVPDRFSGSGSGTD FTLRISRVEADDVGVYYCHQSYEDPWTFGPGTKLEIK | Exemplary felinized, matured variable light chain sequence "fmVL3c" N34R Q93H |
| 55 | QLTLRESGPGLVKPSQSLSLTCSVT | Exemplary felinized, matured HC-FR1 |

TABLE 1-continued

Description of Certain Sequences

| SEQ ID NO: | SEQUENCE | DESCRIPTION |
|---|---|---|
| 56 | DVQLVESGGDLVKPGGSLRLTCSVT | Exemplary felinized, matured HC-FRI |
| 57 | KWIRQRPGRGLEWLG | Exemplary felinized, matured HC-FR2 |
| 58 | KWVRQAPGKGLQWVA | Exemplary felinized, matured HC-FR2 |
| 59 | KWIRKFPGNKLEYMG | Exemplary felinized, matured HC-FR2 |
| 60 | NPSLKSRISITADTAQNQFSLQLSSMTTEDTAVYYC | Exemplary felinized, matured HC-FR3 |
| 61 | NPSLKSRFTISRDNAKNTLYLQMNSLKTEDTATYYC | Exemplary felinized, matured HC-FR3 |
| 62 | WGPGALVTVSS | Exemplary felinized, matured HC-FR4 |
| 63 | WGQGALVTVSS | Exemplary felinized, matured HC-FR4 |
| 64 | DIVMTQTPLSLSVTPGEPASISC | Exemplary felinized, matured LC-FRI |
| 65 | DVVMTQTPLSLPVTPGEPASISC | Exemplary felinized, matured LC-FRI |
| 66 | WYLQKPGQSPRRLIY | Exemplary felinized, matured LC-FR2 |
| 67 | WYLQKPGQSPRLLIY | Exemplary felinized, matured LC-FR2 |
| 68 | WYQQKPGQSPKLLIY | Exemplary felinized, matured LC-FR2 |
| 69 | GVPDRFSGSGSGTDFTLRISRVEADDVGVYYC | Exemplary felinized, matured LC-FR3 |
| 70 | GVPDRFSGSGSGTDFTLRISRVEADDVATYYC | Exemplary felinized, matured LC-FR3 |
| 71 | FGPGTKLEIK | Exemplary felinized, matured LC-FR4 |
| 72 | FGQGTKLEVK | Exemplary felinized, matured LC-FR4 |
| 73 | QLTLRESGPGLVKPSQSLSLTCSVTGDSITSGYWKWI RQRPGRGLEWLGYISYSGITDYNPSLKSRISITADTA QNQFSLQLSSMTTEDTAVYYCARYANYGYAMDYWGPG ALVTVSSASTTAPSVFPLAPSCGTTSGATVALACLVL GYFPEPVTVSWNSGALTSGVHTFPAVLQASGLYSLSS MVTVPSSRWLSDTFTCNVAHPPSNTKVDKTVRKTDHP PGPKPCDCPKCPPPEMLGGPSIFIFPPKPKDTLSISR TPEVTCLVVDLGPDDSDVQITWFVDNTQVYTAKTSPR EEQFNSTYRVVSVLPILHQDWLKGKEFKCKVNSKSLP SPIERTISKAKGQPHEPQVYVLPPAQEELSRNKVSVT CLIKSFHPPDIAVEWEITGQPEPENNYRTTPPQLDSD GTYFVYSKLSVDRSHWQRGNTYTCSVSHEALHSHHTQ KSLTQSPGK | Exemplary felinized, matured variable heavy chain sequence fmVH3a and feline heavy chain constant region |
| 74 | DVQLVESGGDLVKPGGSLRLTCSVTGDSITSGYWKWV RQAPGKGLQWVAYISYSGITDYNPSLKSRFTISRDNA KNTLYLQMNSLKTEDTATYYCARYANYGYAMDYWGQG ALVTVSSASTTAPSVFPLAPSCGTTSGATVALACLVL GYFPEPVTVSWNSGALTSGVHTFPAVLQASGLYSLSS MVTVPSSRWLSDTFTCNVAHPPSNTKVDKTVRKTDHP PGPKPCDCPKCPPPEMLGGPSIFIFPPKPKDTLSISR TPEVTCLVVDLGPDDSDVQITWFVDNTQVYTAKTSPR EEQFNSTYRVVSVLPILHQDWLKGKEFKCKVNSKSLP SPIERTISKAKGQPHEPQVYVLPPAQEELSRNKVSVT | Exemplary felinized, matured variable heavy chain sequence fmVH3b and feline heavy chain constant region |

TABLE 1-continued

Description of Certain Sequences

| SEQ ID NO: | SEQUENCE | DESCRIPTION |
|---|---|---|
| | CLIKSFHPPDIAVEWEITGQPEPENNYRTTPPQLDSD GTYFVYSKLSVDRSHWQRGNTYTCSVSHEALHSHHTQ KSLTQSPGK | |
| 75 | DVQLVESGGDLVKPGGSLRLTCSVTGDSITSGYWKWI RKFPGNKLEYMGYISYSGITDYNPSLKSRFTISRDNA KNTLYLQMNSLKTEDTATYYCARYANYGYAMDYWGQG ALVTVSSASTTAPSVFPLAPSCGTTSGATVALACLVL GYFPEPVTVSWNSGALTSGVHTFPAVLQASGLYSLSS MVTVPSSRWLSDTFTCNVAHPPSNTKVDKTVRKTDHP PGPKPCDCPKCPPPEMLGGPSIFIFPPKPKDTLSISR TPEVTCLVVDLGPDDSDVQITWFVDNTQVYTAKTSPR EEQFNSTYRVVSVLPILHQDWLKGKEFKCKVNSKSLP SPIERTISKAKGQPHEPQVYVLPPAQEELSRNKVSVT CLIKSFHPPDIAVEWEITGQPEPENNYRTTPPQLDSD GTYFVYSKLSVDRSHWQRGNTYTCSVSHEALHSHHTQ KSLTQSPGK | Exemplary felinized, matured variable heavy chain sequence fmVH3c and feline heavy chain constant region |
| 91 | QLTLRESGPGLVKPSQSLSLTCSVTGDSITSGYWKWI RQRPGNKLEYMGYISYSGITDYNPAFQGRISITADTA QNQFSLQLSSMTTEDTAVYYCARYPNYGYAMDYWGPG TLVTVSSASTTAPSVFPLAPSCGTTSGATVALACLVL GYFPEPVTVSWNSGALTSGVHTFPAVLQASGLYSLSS MVTVPSSRWLSDTFTCNVAHPPSNTKVDKTVRKTDHP PGPKPCDCPKCPPPEMLGGPSIFIFPPKPKDTLYITR EPEVTCLVVDLGPDDSDVQITWFVDNTQVYTAKTSPR EEQFNSTYRVVSVLPILHQDWLKGKEFKCKVNSKSLP SPIERTISKAKGQPHEPQVYVLPPAQEELSRNKVSVT CLIKSFHPPDIAVEWEITGQPEPENNYRTTPPQLDSD GTYFVYSKLSVDRSHWQRGNTYTCSVSHEALHSHHTQ KSLTQSPGK | Exemplary felinized, matured variable heavy chain sequence fmVH2 and feline heavy chain constant region |
| 76 | DIVMTQTPLSLSVTPGEPASISCRASESVDTYGRSFM HWYLQKPGQSPRRLIYRASNLESGVPDRFSGSGSGTD FTLRISRVEADDVGVYYCHQSYEDPWTFGPGTKLEIK RSDAQPSVFLFQPSLDELHTGSASIVCILNDFYPKEV NVKWKVDGVVQNKGIQESTTEQNSKDSTYSLSSTLTM SSTEYQSHEKFSCEVTHKSLASTLVKSFNRSECQRE | Exemplary felinized, matured variable light chain sequence fmVL3a and feline light chain constant region |
| 77 | DVVMTQTPLSLPVTPGEPASISCRASESVDTYGRSFM HWYLQKPGQSPRLLIYRASNLESGVPDRFSGSGSGTD FTLRISRVEADDVATYYCHQSYEDPWTFGQGTKLEVK RSDAQPSVFLFQPSLDELHTGSASIVCILNDFYPKEV NVKWKVDGVVQNKGIQESTTEQNSKDSTYSLSSTLTM SSTEYQSHEKFSCEVTHKSLASTLVKSFNRSECQRE | Exemplary felinized, matured variable light chain sequence fmVL3b and feline light chain constant region |
| 78 | DIVMTQTPLSLSVTPGEPASISCRASESVDTYGRSFM HWYQQKPGQSPKLLIYRASNLESGVPDRFSGSGSGTD FTLRISRVEADDVGVYYCHQSYEDPWTFGPGTKLEIK RSDAQPSVFLFQPSLDELHTGSASIVCILNDFYPKEV NVKWKVDGVVQNKGIQESTTEQNSKDSTYSLSSTLTM SSTEYQSHEKFSCEVTHKSLASTLVKSFNRSECQRE | Exemplary felinized, matured variable light chain sequence fmVL3c and feline light chain constant region |
| 79 | MLSHTGPSRFALFLLCSMETLLSSHMAPTHQLPPSDV RKIILELQPLSRGLLEDYQKKETGVPESNRTLLLCLT SDSQPPRLNSSAILPYFRAIRPLSDKNIIDKIIEQLD KLKFQHEPETEISVPADTFECKSFILTILQQFSACLE SVFKSLNSGPQ | Canine IL31 amino acid sequence |
| 80 | SSHMAPTHQLPPSDVRKIILELQPLSRGLLEDYQKKE TGVPESNRTLLLCLTSDSQPPRLNSSAILPYFRAIRP LSDKNIIDKIIEQLDKLKFQHEPETEISVPADTFECK SFILTILQQFSACLESVFKSLNSGPQ | Mature canine IL31 amino acid sequence |
| 81 | MLSHAGPARFALFLLCCMETLLPSHMAPAHRLQPSDV RKIILELRPMSKGLLQDYLKKEIGLPESNHSSLPCLS SDSQLPHINGSAILPYFRAIRPLSDKNTIDKIIEQLD KLKFQREPEAKVSMPADNFERKNFILAVLQQFSACLE HVLQSLNSGPQ | Feline IL31 amino acid sequence NCBI ref: XP_011286140.1 [felis catus] |
| 82 | MIFHTGTTKPTLVLLCCIGTWLATCSLSFGAPISKED LRTTIDLLKQESQDLYNNYSIKQASGMSADESIQLPC FSLDREALTNISVIIAHLEKVKVLSENTVDTSWVIRW LTNISCFNPLNLNISVPGNTDESYDCKVFVLTVLKQE SNCMAELQAKDNTTC | Murine IL31 precursor amino acid sequence NCBI ref: NP_083870 [mus musculus] |

TABLE 1-continued

Description of Certain Sequences

| SEQ ID NO: | SEQUENCE | DESCRIPTION |
|---|---|---|
| 83 | ASTTAPSVFPLAPSCGSTSGSTVALACLVSGYFPEPV<br>TVSWNSGSLTSGVHTFPSVLQSSGLHSLSSMVTVPSS<br>RWPSETFTCNVVHPASNTKVDKPVFNECRCTDTPCPV<br>PEPLGGPSVLIFPPKPKDILRITRTPEVTCVVLDLGR<br>EDPEVQISWFVDGKEVHTAKTQSREQQFNGTYRVVSV<br>LPIEHQDWLTGKEFKCRVNHIDLPSPIERTISKARGR<br>AHKPSVYVLPPSPKELSSSDTVSITCLIKDFYPPDID<br>VEWQSNGQQEPERKHRMTPPQLDEDGSYFLYSKLSVD<br>KSRWQQGDPFTCAVMHETLQNHYTDLSLSHSPGK | Exemplary canine constant<br>heavy chain IgG-A |
| 84 | ASTTAPSVFPLAPSCGSTSGSTVALACLVSGYFPEPV<br>TVSWNSGSLTSGVHTFPSVLQSSGLYSLSSMVTVPSS<br>RWPSETFTCNVAHPASKTKVDKPVPKRENGRVPRPPD<br>CPKCPAPEMLGGPSVFIFPPKPKDTLLIARTPEVTCV<br>VVDLDPEDPEVQISWFVDGKQMQTAKTQPREEQFNGT<br>YRVVSVLPIGHQDWLKGKQFTCKVNNKALPSPIERTI<br>SKARGQAHQPSVYVLPPSREELSKNTVSLTCLIKDFF<br>PPDIDVEWQSNGQQEPESKYRTTPPQLDEDGSYFLYS<br>KLSVDKSRWQRGDTFICAVMHEALHNHYTQESLSHSP<br>GK | Exemplary canine constant<br>heavy chain IgG-B |
| 85 | ASTTAPSVFPLAPSCGSQSGSTVALACLVSGYIPEPV<br>TVSWNSVSLTSGVHTFPSVLQSSGLYSLSSMVTVPSS<br>RWPSETFTCNVAHPATNTKVDKPVAKECECKCNCNNC<br>PCPGCGLLGGPSVFIFPPKPKDILVTARTPTVTCVVV<br>DLDPENPEVQISWFVDSKQVQTANTQPREEQSNGTYR<br>VVSVLPIGHQDWLSGKQFKCKVNNKALPSPIEEIISK<br>TPGQAHQPNVYVLPPSRDEMSKNTVTLTCLVKDFFPP<br>EIDVEWQSNGQQEPESKYRMTPPQLDEDGSYFLYSKL<br>SVDKSRWQRGDTFICAVMHEALHNHYTQISLSHSPGK | Exemplary canine constant<br>heavy chain IgG-C |
| 86 | ASTTAPSVFPLAPSCGSTSGSTVALACLVSGYFPEPV<br>TVSWNSGSLTSGVHTFPSVLQSSGLYSLSSTVTVPSS<br>RWPSETFTCNVVHPASNTKVDKPVPKESTCKCISPCP<br>VPESLGGPSVFIFPPKPKDILRITRTPEITCVVLDLG<br>REDPEVQISWFVDGKEVHTAKTQPREQQFNSTYRVVS<br>VLPIEHQDWLTGKEFKCRVNHIGLPSPIERTISKARG<br>QAHQPSVYVLPPSPKELSSSDTVTLTCLIKDFFPPEI<br>DVEWQSNGQPEPESKYHTTAPQLDEDGSYFLYSKLSV<br>DKSRWQQGDTFTCAVMHEALQNHYTDLSLSHSPGK | Exemplary canine constant<br>heavy chain IgG-D |
| 87 | RNDAQPAVYLFQPSPDQLHTGSASVVCLLNSFYPKDI<br>NVKWKVDGVIQDTGIQESVTEQDKDSTYSLSSTLTMS<br>STEYLSHELYSCEITHKSLPSTLIKSFQRSECQRVD | Exemplary canine constant<br>light chain |
| 88 | ASTTAPSVFPLAPSCGTTSGATVALACLVLGYFPEPV<br>TVSWNSGALTSGVHTFPAVLQASGLYSLSSMVTVPSS<br>RWLSDTFTCNVAHPPSNTKVDKTVRKTDHPPGPKPCD<br>CPKCPPPEMLGGPSIFIFPPKPKDTLSISRTPEVTCL<br>VVDLGPDDSDVQITWFVDNTQVYTAKTSPREEQFNST<br>YRVVSVLPILHQDWLKGKEFKCKVNSKSLPSPIERTI<br>SKAKGQPHEPQVYVLPPAQEELSRNKVSVTCLIKSFH<br>PPDIAVEWEITGQPEPENNYRTTPPQLDSDGTYFVYS<br>KLSVDRSHWQRGNTYTCSVSHEALHSHHTQKSLTQSP<br>GK | Exemplary feline constant<br>heavy chain IgG |
| 89 | RSDAQPSVFLFQPSLDELHTGSASIVCILNDFYPKEV<br>NVKWKVDGVVQNKGIQESTTEQNSKDSTYSLSSTLTM<br>SSTEYQSHEKFSCEVTHKSLASTLVKSFNRSECQRE | Exemplary feline constant<br>light chain |
| 92 | <u>MMWAKVLWMLLLLCKLSLAVLPAKPENISCIFYYEEN</u><br>FTCTWSPEKEASYTWYKVKRTYSYGYKSDICSTDNST<br>RGNHASCSFLPPTITNPDNYTIQVEAQNADGIMKSDI<br>TYWNLDAIMKIEPPEIFSVKSVLGIKRMLQIKWIRPV<br>LAPHSSTLKYTLRFRTINSAYWMEVNFTKEDIDRDET<br>YNLTELQAFTEYVMTLRCAPAESMFWSGWSQEKVGTT<br>EEEAPYGLDLWRVLKPAMVDGRRPVQLMWKKATGAPV<br>LEKALGYNIWYFPENNTNLTETVNTTNQTHELYLGGK<br>TYWVYVVSYNSLGESPVATLRIPALNEKTFQCIEAMQ<br>ACLTQDQLVVEWQSSAPEVDTWMVEWFPDVDSEPSSF<br>SWESVSQARNWTIQKDELKPLWCYNISVYPVLRDRVG<br>QPYSTQAYVQEGIPSAGPVTQADSIGVKTVTITWKEI<br>PKSKRNGFIKNYTIFYQAEDGKEFSKTVNSNILQYRL<br>ESLTRRTSYSLQVMASTNAGGTNGTKINFKTLSISVL | Canine IL31Ra amino acid<br>sequence with linker, flag<br>and signal sequence |

TABLE 1-continued

Description of Certain Sequences

| SEQ ID NO: | SEQUENCE | DESCRIPTION |
|---|---|---|
| | EIFFITSLVGGGFLILIMLTVAYGLKKPNKLKHLCWP | |
| | DVPNPAESSIATWRGDDFKDKLNLKESDDPVNMEEDQ | |
| | VLKPYSAPTDFIDKLVVNFENFLEEVSTEELGKSQEN | |
| | ILKEEKNKHVTSPYCLHHPPISTEIPQRKPQQLCSRI | |
| | PEGTCSETKEQLFSSVQSLGPDHLCEEGEPNPYLKNS | |
| | VTTREFVGSGSDYKDDDDK | |
| 93 | MKEFALQFSHIGRPPNGVTWARVLYCNSFQRLQCTGC | Feline IL31Ra amino acid |
| | TPNWMWGGQLSPVRPARTSSGYHREFSPQPACIDLGM | sequence with linker, flag |
| | MWAHALWTLLLLCKFSLAVLPAKPENISCVFYYEENF | and signal sequence |
| | TCTWSPEKEASYTWYKVKRTYSYGYKSDICPSDNSTR | Feline IL31Ra NCBI |
| | GNHTFCSFLPPTITNPDNYTIQVEAQNADGIIKSDIT | reference: |
| | HWSLDAITKIEPPEIFSVKPVLGVKRMVQIKWIRPVL | XP_019689862.2 |
| | APVSSTLKYTLRFKTVNSAYWMEVNFTKEDIDRDETY | |
| | NLTGLQAFTEYVLALRCATKESMFWSGWSQEKMGTTE | |
| | EEAPHGLDLWRVLRPATVDGRRLVQLMWKKASGAPVL | |
| | EKALGYNIWYFPENSTNLTKTLNTTNEKLELYLGGKT | |
| | YWVCVVSYNSLGESPVATLRIPAIDEKSFQCIEAMQA | |
| | CLTQDQLVVEWRSSAPEVDTWMVEWFPDLDSEPSTFS | |
| | WESVSQATNWTIKQDELKPFWCYNISVYPVLQDRVGK | |
| | PFSIQAYVREGIPSAGPVTQVDNIGVKTVTITWKEIP | |
| | KSQRNGFITNYTIFYQAEDGKEFSKTVNSNILQYDLE | |
| | SLTRKTSYSLQVMASTSAGGINGTTMNFKTLSISILE | |
| | IFLIISLVGGGLLILIILSVAYGLKKPNRLKHLCWPD | |
| | VPNPAESSIATWRGDDFKDKINLKESDDPVNMEEDRV | |
| | LKPYSSPRDLIDKLVVNFETFLEDVSTEELGKGQENI | |
| | LREEKNEYVTSPYRPYCPPISTEIPQRKSQQLCSRIP | |
| | EGICLETTEQLLSSVPNLGRDRICEEGEPNPYLKNSV | |
| | TTREFLTSEKLPEQTKREVGSGSDYKDDDDK | |

DESCRIPTION OF CERTAIN EMBODIMENTS

Antibodies with enhanced binding to canine IL31 and feline IL31 are provided. Antibody heavy chains and light chains that are capable of forming antibodies that bind canine and feline IL31 are also provided. In addition, antibodies, heavy chains, and light chains comprising one or more particular complementary determining regions (CDRs) are provided. Polynucleotides encoding antibodies to canine and feline IL31 are provided. Methods of producing or purifying antibodies to canine and feline IL31 are also provided. Methods of treatment using antibodies to canine and feline IL31 are provided. Such methods include, but are not limited to, methods of treating IL31-induced conditions in companion animal species. Methods of detecting IL31 in a sample from a companion animal species are provided.

For the convenience of the reader, the following definitions of terms used herein are provided.

As used herein, numerical terms such as Kd are calculated based upon scientific measurements and, thus, are subject to appropriate measurement error. In some instances, a numerical term may include numerical values that are rounded to the nearest significant figure.

As used herein, "a" or "an" means "at least one" or "one or more" unless otherwise specified. As used herein, the term "or" means "and/or" unless specified otherwise. In the context of a multiple dependent claim, the use of "or" when referring back to other claims refers to those claims in the alternative only.

Exemplary Anti-IL31 Antibodies

Antibodies having enhanced affinity to canine IL31 and feline IL31 are provided. Anti-IL31 antibodies provided herein include, but are not limited to, monoclonal antibodies, chimeric antibodies, caninized antibodies, and felinized antibodies.

Also provided herein are amino acid sequences of affinity matured antibodies with enhanced binding to canine and feline IL-31. For example, the variable heavy chain CDRs (SEQ ID NOs: 11-15), variable light chain CDRs (SEQ ID NOs: 20-24), variable region heavy chain framework sequences (SEQ ID NOs: 16-19, 25-28, 55-72), and variable region light chain framework sequences (SEQ ID NOs: 11-14) for exemplary matured antibodies (caninized and felinized) are provided. Exemplary amino acid sequences of the variable light chain, light chain, variable heavy chain, and heavy chain of exemplary matured antibodies (caninized and felinized) are provided (e.g., SEQ ID NOs:5-10, 29-54, 73-78).

The term "antibody" herein is used in the broadest sense and encompasses various antibody structures, including but not limited to monoclonal antibodies, polyclonal antibodies, multispecific antibodies (for example, bispecific (such as Bi-specific T-cell engagers) and trispecific antibodies), and antibody fragments (such as Fab, F(ab')₂, ScFv, minibody, diabody, triabody, and tetrabody) so long as they exhibit the desired antigen-binding activity. Canine, feline, and equine species have different varieties (classes) of antibodies that are shared by many mammalians.

The term antibody includes, but is not limited to, fragments that are capable of binding to an antigen, such as Fv, single-chain Fv (scFv), Fab, Fab', di-scFv, sdAb (single domain antibody) and (Fab')₂ (including a chemically linked F(ab')₂). Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')₂ fragment that has two antigen combining sites and is still capable of cross-linking antigen. The term antibody also includes, but is not limited to, chimeric antibodies, humanized antibodies, and antibodies of various species such as mouse, human, cyno-
molgus monkey, canine, feline, equine, etc. Furthermore, for
all antibody constructs provided herein, variants having the
sequences from other organisms are also contemplated.
Thus, if a murine version of an antibody is disclosed, one of
skill in the art will appreciate how to transform the murine
sequence based antibody into a cat, dog, horse, etc.
sequence. Antibody fragments also include either orientation
of single chain scFvs, tandem di-scFv, diabodies, tandem
tri-sdcFv, minibodies, etc. Antibody fragments also include
nanobodies (sdAb, an antibody having a single, monomeric
domain, such as a pair of variable domains of heavy chains,
without a light chain). An antibody fragment can be referred
to as being a specific species in some embodiments (for
example, mouse scFv or a canine scFv). This denotes the
sequences of at least part of the non-CDR regions, rather
than the source of the construct. In some embodiments, the
antibodies comprise a label or are conjugated to a second
moiety.

The terms "label" and "detectable label" mean a moiety
attached to an antibody or its analyte to render a reaction (for
example, binding) between the members of the specific
binding pair, detectable. The labeled member of the specific
binding pair is referred to as "detectably labeled." Thus, the
term "labeled binding protein" refers to a protein with a label
incorporated that provides for the identification of the bind-
ing protein. In some embodiments, the label is a detectable
marker that can produce a signal that is detectable by visual
or instrumental means, for example, incorporation of a
radiolabeled amino acid or attachment to a polypeptide of
biotinyl moieties that can be detected by marked avidin (for
example, streptavidin containing a fluorescent marker or
enzymatic activity that can be detected by optical or colo-
rimetric methods). Examples of labels for polypeptides
include, but are not limited to, the following: radioisotopes
or radionuclides (for example, $^3$H, $^{14}$C, $^{35}$S, $^{90}$Y, $^{99}$Tc, $^{111}$In,
$^{125}$I $^{131}$I, $^{177}$Lu, $^{166}$Ho, or $^{153}$Sm); chromogens, fluorescent
labels (for example, FITC, rhodamine, lanthanide phos-
phors), enzymatic labels (for example, horseradish peroxi-
dase, luciferase, alkaline phosphatase); chemiluminescent
markers; biotinyl groups; predetermined polypeptide
epitopes recognized by a secondary reporter (for example,
leucine zipper pair sequences, binding sites for secondary
antibodies, metal binding domains, epitope tags); and mag-
netic agents, such as gadolinium chelates. Representative
examples of labels commonly employed for immunoassays
include moieties that produce light, for example, acridinium
compounds, and moieties that produce fluorescence, for
example, fluorescein. In this regard, the moiety itself may
not be detectably labeled but may become detectable upon
reaction with yet another moiety.

The term "monoclonal antibody" refers to an antibody of
a substantially homogeneous population of antibodies, that
is, the individual antibodies comprising the population are
identical except for possible naturally-occurring mutations
that may be present in minor amounts. Monoclonal antibod-
ies are highly specific, being directed against a single
antigenic site. Furthermore, in contrast to polyclonal anti-
body preparations, which typically include different anti-
bodies directed against different determinants (epitopes),
each monoclonal antibody is directed against a single deter-
minant on the antigen. Thus, a sample of monoclonal
antibodies can bind to the same epitope on the antigen. The
modifier "monoclonal" indicates the character of the anti-
body as being obtained from a substantially homogeneous
population of antibodies, and is not to be construed as
requiring production of the antibody by any particular method. For example, the monoclonal antibodies may be
made by the hybridoma method first described by Kohler
and Milstein, 1975, Nature 256:495, or may be made by
recombinant DNA methods such as described in U.S. Pat.
No. 4,816,567. The monoclonal antibodies may also be
isolated from phage libraries generated using the techniques
described in McCafferty et al., 1990, Nature 348:552-554,
for example.

"Amino acid sequence," means a sequence of amino acids
residues in a peptide or protein. The terms "polypeptide" and
"protein" are used interchangeably to refer to a polymer of
amino acid residues, and are not limited to a minimum
length. Such polymers of amino acid residues may contain
natural or non-natural amino acid residues, and include, but
are not limited to, peptides, oligopeptides, dimers, trimers,
and multimers of amino acid residues. Both full-length
proteins and fragments thereof are encompassed by the
definition. The terms also include post-expression modifi-
cations of the polypeptide, for example, glycosylation, sialy-
lation, acetylation, phosphorylation, and the like. Further-
more, for purposes of the present disclosure, a "polypeptide"
refers to a protein which includes modifications, such as
deletions, additions, and substitutions (generally conserva-
tive in nature), to the native sequence, as long as the protein
maintains the desired activity. These modifications may be
deliberate, as through site-directed mutagenesis, or may be
accidental, such as through mutations of hosts which pro-
duce the proteins or errors due to PCR amplification.

"IL31" as used herein refers to any native IL31 that results
from expression and processing of IL31 in a cell. The term
includes IL31 from any vertebrate source, including mam-
mals such as primates (e.g., humans and cynomolgus mon-
keys) and rodents (e.g., mice and rats), and companion
animals (e.g., dogs, cats, and equine), unless otherwise
indicated. The term also includes naturally occurring vari-
ants of IL31, e.g., splice variants or allelic variants.

In some embodiments, a canine IL31 comprises the amino
acid sequence of SEQ ID NO: 79 or SEQ ID NO: 80. In
some embodiments, a feline IL31 comprises the amino acid
sequence of SEQ ID NO: 81. In some embodiments, a
murine IL31 comprises the amino acid sequence of SEQ ID
NO: 82.

The term "IL31 binding domain" of an antibody means
the binding domain formed by a light chain and heavy chain
of an anti-IL31 antibody, which binds IL31.

In some embodiments, the IL31 binding domain binds
canine IL31 or feline IL31 with greater affinity than it binds
human IL31. In some embodiments, the IL31 binding
domain binds IL31 of other companion animals, such as
equine IL31. In some embodiments, the IL31 binding
domain does not bind human IL31.

As used herein, the term "epitope" refers to a site on a
target molecule (for example, an antigen, such as a protein,
nucleic acid, carbohydrate or lipid) to which an antigen-
binding molecule (for example, an antibody, antibody frag-
ment, or scaffold protein containing antibody binding
regions) binds. Epitopes often include a chemically active
surface grouping of molecules such as amino acids, poly-
peptides or sugar side chains and have specific three dimen-
sional structural characteristics as well as specific charge
characteristics. Epitopes can be formed both from contigu-
ous or juxtaposed noncontiguous residues (for example,
amino acids, nucleotides, sugars, lipid moiety) of the target
molecule. Epitopes formed from contiguous residues (for
example, amino acids, nucleotides, sugars, lipid moiety)
typically are retained on exposure to denaturing solvents
whereas epitopes formed by tertiary folding typically are lost on treatment with denaturing solvents. An epitope may include but is not limited to at least 3, at least 5 or 8-10 residues (for example, amino acids or nucleotides). In some examples an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between an antibody residue and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antibody. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

The term "CDR" means a complementarity determining region as defined by at least one manner of identification to one of skill in the art. In some embodiments, CDRs can be defined in accordance with any of the Chothia numbering schemes, the Kabat numbering scheme, a combination of Kabat and Chothia, the AbM definition, the contact definition, or a combination of the Kabat, Chothia, AbM, or contact definitions. The various CDRs within an antibody can be designated by their appropriate number and chain type, including, without limitation as CDR-H1, CDR-H2, CDR-H3, CDR-L1, CDR-L2, and CDR-L3. The term "CDR" is used herein to also encompass a "hypervariable region" or HVR, including hypervariable loops.

In some embodiments, an anti-IL31 antibody comprises:
a) a heavy chain comprising a CDR-H3 sequence having the amino acid sequence of SEQ ID NO: 14 or SEQ ID NO: 15; and/or
b) a light chain comprising a CDR-L1 sequence having the amino acid sequence of SEQ ID NO: 20; and/or
c) a light chain comprising a CDR-L3 sequence having the amino acid sequence of SEQ ID NO: 23 or SEQ ID NO: 24.

In some embodiments, an anti-IL31 antibody comprises:
a) a heavy chain comprising a CDR-H1 sequence having the amino acid sequence of SEQ ID NO: 11, a CDR-H2 sequence having the amino acid sequence of SEQ ID NO: 12, and a CDR-H3 sequence having the amino acid sequence of SEQ ID NO: 13, SEQ ID NO: 14, or SEQ ID NO: 15; and/or
b) a light chain comprising a CDR-L1 sequence having the amino acid sequence of SEQ ID NO: 20, a CDR-L2 sequence having the amino acid sequence of SEQ ID NO: 21, and a CDR-L3 sequence having the amino acid sequence of SEQ ID NO: 22, SEQ ID NO: 23, or SEQ ID NO: 24.

The term "variable region" as used herein refers to a region comprising at least three CDRs. In some embodiments, the variable region includes the three CDRs and at least one framework region ("FR"). The terms "heavy chain variable region" or "variable heavy chain" are used interchangeably to refer to a region comprising at least three heavy chain CDRs. The terms "light chain variable region" or "variable light chain" are used interchangeably to refer to a region comprising at least three light chain CDRs. In some embodiments, the variable heavy chain or variable light chain comprises at least one framework region. In some embodiments, an antibody comprises at least one heavy chain framework region selected from HC-FR1, HC-FR2, HC-FR3, and HC-FR4. In some embodiments, an antibody comprises at least one light chain framework region selected from LC-FR1, LC-FR2, LC-FR3, and LC-FR4. The framework regions may be juxtaposed between light chain CDRs or between heavy chain CDRs. For example, an antibody may comprise a variable heavy chain having the following structure: (HC-FR1)-(CDR-H1)-(HC-FR2)-(CDR-H2)-(HC-FR3)-(CDR-H3)-(HC-FR4). An antibody may comprise a variable heavy chain having the following structure: (CDR-H1)-(HC-FR2)-(CDR-H2)-(HC-FR3)-(CDR-H3). An antibody may also comprise a variable light chain having the following structure: (LC-FR1)-(CDR-L1)-(LC-FR2)-(CDR-L2)-(LC-FR3)-(CDR-L3)-(LC-FR4). An antibody may also comprise a variable light chain having the following structure: (CDR-L1)-(LC-FR2)-(CDR-L2)-(LC-FR3)-(CDR-L3).

In some embodiments, an anti-IL31 antibody comprises one or more of (a) a variable region heavy chain framework 1 (HC-FR1) sequence of SEQ ID NO: 16; (b) a HC-FR2 sequence of SEQ ID NO: 17; (c) a HC-FR3 sequence of SEQ ID NO: 18; (d) a HC-FR4 sequence of SEQ ID NO: 19; (e) a variable region light chain framework 1 (LC-FR1) sequence of SEQ ID NO: 25; (0 an LC-FR2 sequence of SEQ ID NO: 26; (g) an LC-FR3 sequence of SEQ ID NO: 27; or (h) an LC-FR4 sequence of SEQ ID NO: 28.

In some embodiments, an anti-IL31 antibody comprises one or more of (a) a variable region heavy chain framework 1 (HC-FR1) sequence of SEQ ID NO: 55 or SEQ ID NO: 56; (b) a HC-FR2 sequence of SEQ ID NO: 57, SEQ ID NO: 58, SEQ ID NO: 59; (c) a HC-FR3 sequence of SEQ ID NO: 60 or SEQ ID NO: 61; (d) a HC-FR4 sequence of SEQ ID NO: 62 or SEQ ID NO: 63; (e) a variable region light chain framework 1 (LC-FR1) sequence of SEQ ID NO: 64 or SEQ ID NO: 65; (0 an LC-FR2 sequence of SEQ ID NO: 66, SEQ ID NO: 67, or SEQ ID NO: 68; (g) an LC-FR3 sequence of SEQ ID NO: 69 or SEQ ID NO: 70; or (h) an LC-FR4 sequence of SEQ ID NO: 71 or SEQ ID NO: 72.

The term "constant region" as used herein refers to a region comprising at least three constant domains. The terms "heavy chain constant region" or "constant heavy chain" are used interchangeably to refer to a region comprising at least three heavy chain constant domains, CH1, CH2, and CH3. Nonlimiting exemplary heavy chain constant regions include $\gamma$, $\delta$, $\alpha$, $\varepsilon$, and $\mu$. Each heavy chain constant region corresponds to an antibody isotype. For example, an antibody comprising a $\gamma$ constant region is an IgG antibody, an antibody comprising a $\delta$ constant region is an IgD antibody, an antibody comprising an a constant region is an IgA antibody, an antibody comprising a $\mu$ constant region is an IgM antibody, and an antibody comprising an E constant region is an IgE antibody. Certain isotypes can be further subdivided into subclasses. For example, IgG antibodies include, but are not limited to, IgG1 (comprising a $\gamma_1$ constant region), IgG2 (comprising a $\gamma_2$ constant region), IgG3 (comprising a $\gamma_3$ constant region), and IgG4 (comprising a $\gamma_4$ constant region) antibodies; IgA antibodies include, but are not limited to, IgA1 (comprising an al constant region) and IgA2 (comprising an $\alpha_2$ constant region) antibodies; and IgM antibodies include, but are not limited to IgM1 and IgM2. The terms "light chain constant region" or "constant light chain" are used interchangeably to refer to a region comprising a light chain constant domain, CL. Nonlimiting exemplary light chain constant regions include λ and κ. Non-function-altering deletions and alterations within the domains are encompassed within the scope of the term "constant region" unless designated otherwise. Canine, feline, and equine have antibody classes such as IgG, IgA, IgD, IgE, and IgM. Within the canine IgG antibody class are IgG-A, IgG-B, IgG-C, and IgG-D. Within the feline IgG antibody class are IgG1a, IgG1b, and IgG2.

The term "chimeric antibody" or "chimeric" refers to an antibody in which a portion of the heavy chain or light chain is derived from a particular source or species, while at least a part of the remainder of the heavy chain or light chain is derived from a different source or species. In some embodiments, a chimeric antibody refers to an antibody comprising at least one variable region from a first species (such as mouse, rat, cynomolgus monkey, etc.) and at least one constant region from a second species (such as human, dog, cat, equine, etc.).

In some embodiments, an anti-IL31 antibody comprises a canine heavy chain constant region selected from an IgG-A, IgG-B, IgG-C, and IgG-D constant region. In some embodiments, an anti-IL31 antibody is (a) a canine IgG-A antibody comprising the heavy chain amino acid sequence of SEQ ID NO: 83; (b) a canine IgG-B antibody comprising the heavy chain amino acid sequence of SEQ ID NO: 84; (c) a canine IgG-C antibody comprising the heavy chain amino acid sequence of SEQ ID NO: 85; or (d) a canine IgG-D antibody comprising the heavy chain amino acid sequence of SEQ ID NO: 86.

In some embodiments, an anti-IL31 antibody comprises a feline heavy chain constant region selected from an IgG1, IgG2a, and IgG2b constant region.

A "caninized antibody" means an antibody in which at least one amino acid in a portion of a non-canine variable region has been replaced with the corresponding amino acid from a canine variable region. In some embodiments, a caninized antibody comprises at least one canine constant region (e.g., a γ constant region, an a constant region, a δ constant region, an ε constant region, a μ constant region, or etc.) or fragment thereof. In some embodiments, a caninized antibody is an antibody fragment, such as Fab, scFv, (Fab')$_2$, etc. The term "caninized" also denotes forms of non-canine (for example, murine) antibodies that are chimeric immunoglobulins, immunoglobulin chains, or fragments thereof (such as Fv, Fab, Fab', F(ab')$_2$ or other antigen-binding sequences of antibodies) that contain minimal sequence of non-canine immunoglobulin. Caninized antibodies can include canine immunoglobulins (recipient antibody) in which residues from a CDR of the recipient are substituted by residues from a CDR of a non-canine species (donor antibody) such as mouse, rat, or rabbit having the desired specificity, affinity, and capacity. In some instances, Fv framework region (FR) residues of the canine immunoglobulin are replaced by corresponding non-canine residues. Furthermore, the caninized antibody can comprise residues that are found neither in the recipient antibody nor in the imported CDR or framework sequences, but are included to further refine and optimize antibody performance.

In some embodiments, the caninized variable chain is fused to a canine constant heavy chain or a canine constant light chain.

A "felinized antibody" means an antibody in which at least one amino acid in a portion of a non-feline variable region has been replaced with the corresponding amino acid from a feline variable region. In some embodiments, a felinized antibody comprises at least one feline constant region (e.g., a γ constant region, an α constant region, a δ constant region, an ε constant region, a μ constant region, or etc.) or fragment thereof. In some embodiments, a felinized antibody is an antibody fragment, such as Fab, scFv, (Fab')$_2$, etc. The term "felinized" also denotes forms of non-feline (for example, murine) antibodies that are chimeric immunoglobulins, immunoglobulin chains, or fragments thereof (such as Fv, Fab, Fab', F(ab')$_2$ or other antigen-binding sequences of antibodies) that contain minimal sequence of non-feline immunoglobulin. Felinized antibodies can include feline immunoglobulins (recipient antibody) in which residues from a CDR of the recipient are substituted by residues from a CDR of anon-feline species (donor antibody) such as mouse, rat, or rabbit having the desired specificity, affinity, and capacity. In some instances, Fv framework region (FR) residues of the feline immunoglobulin are replaced by corresponding non-feline residues. Furthermore, the felinized antibody can comprise residues that are found neither in the recipient antibody nor in the imported CDR or framework sequences, but are included to further refine and optimize antibody performance.

In some embodiments, the felinized variable chain is fused to a feline constant heavy chain or a feline constant light chain. The term "IgX Fc" means the Fc region is derived from a particular antibody isotype (e.g., IgG, IgA, IgD, IgE, IgM, etc.), where "X" denotes the antibody isotype. Thus, "IgG Fc" denotes the Fc region of a γ chain, "IgA Fc" denotes the Fc region of an a chain, "IgD Fc" denotes the Fc region of a δ chain, "IgE Fc" denotes the Fc region of an ε chain, "IgM Fc" denotes the Fc region of a μ chain, etc. In some embodiments, the IgG Fc region comprises CH1, hinge, CH2, CH3, and CL1. "IgX-N-Fc" denotes that the Fc region is derived from a particular subclass of antibody isotype (such as canine IgG subclass A, B, C, or D; or feline IgG subclass 1, 2a, or 2b, etc.), where "N" denotes the subclass. In some embodiments, IgX Fc or IgX-N-Fc regions are derived from a companion animal, such as a dog or a cat. In some embodiments, IgG Fc regions are isolated from canine γ heavy chains, such as IgG-A, IgG-B, IgG-C, or IgG-D. In some instances, IgG Fc regions are isolated from feline γ heavy chains, such as IgG1, IgG2a, or IgG2b. Antibodies comprising an Fc region of IgG-A, IgG-B, IgG-C, or IgG-D may provide for higher expression levels in recombination production systems.

The term "affinity" means the strength of the sum total of noncovalent interactions between a single binding site of a molecule (for example, an antibody) and its binding partner (for example, an antigen). The affinity of a molecule X for its partner Y can generally be represented by the dissociation constant ($K_D$). Affinity can be measured by common methods known in the art, such as, for example, immunoblot, ELISA KD, KinEx A, biolayer interferometry (BLI), or surface plasmon resonance devices.

The terms "$K_D$," "$K_d$," "Kd" or "Kd value" as used interchangeably to refer to the equilibrium dissociation constant of an antibody-antigen interaction. In some embodiments, the $K_d$ of the antibody is measured by using biolayer interferometry assays using a biosensor, such as an Octet® System (Pall ForteBio LLC, Fremont, CA) according to the supplier's instructions. Briefly, biotinylated antigen is bound to the sensor tip and the association of antibody is monitored for ninety seconds and the dissociation is monitored for 600 seconds. The buffer for dilutions and binding steps is 20 mM phosphate, 150 mM NaCl, pH 7.2. A buffer only blank curve is subtracted to correct for any drift. The data are fit to a 2:1 binding model using ForteBio data analysis software to determine association rate constant ($k_{on}$), dissociation rate constant ($k_{off}$), and the $K_d$. The equilibrium dissociation constant ($K_d$) is calculated as the ratio of $k_{off}/k_{on}$. The term "kon" refers to the rate constant for association of an antibody to an antigen and the term "koff" refers to the rate constant for dissociation of an antibody from the antibody/antigen complex.

The term "binds" to an antigen or epitope is a term that is well understood in the art, and methods to determine such binding are also well known in the art. A molecule is said to exhibit "binding" if it reacts, associates with, or has affinity for a particular cell or substance and the reaction, association, or affinity is detectable by one or more methods known in the art, such as, for example, immunoblot, ELISA KD, KinEx A, biolayer interferometry (BLI), surface plasmon resonance devices, or etc.

"Surface plasmon resonance" denotes an optical phenomenon that allows for the analysis of real-time biospecific interactions by detection of alterations in protein concentrations within a biosensor matrix, for example using the BIAcore™ system (BIAcore International AB, a GE Healthcare company, Uppsala, Sweden and Piscataway, N.J.). For further descriptions, see Jonsson et al. (1993) *Ann. Biol. Clin.* 51: 19-26.

"Biolayer interferometry" refers to an optical analytical technique that analyzes the interference pattern of light reflected from a layer of immobilized protein on a biosensor tip and an internal reference layer. Changes in the number of molecules bound to the biosensor tip cause shifts in the interference pattern that can be measured in real-time. A nonlimiting exemplary device for biolayer interferometry is an Octet® system (Pall ForteBio LLC). See, e.g., Abdiche et al., 2008, *Anal. Biochem.* 377: 209-277.

In some embodiments, an anti-IL31 antibody binds to canine IL31 or feline IL31 with a dissociation constant (Kd) of less than $5\times10^{-6}$ M, less than $1\times10^{-6}$ M, less than $5\times10^{-7}$ M, less than $1\times10^{-7}$ M, less than $5\times10^{-8}$M, less than $1\times10^{-8}$M, less than $5\times10^{-9}$M, less than $1\times10^{-9}$ M, less than $5\times10^{-10}$ M, less than $1\times10^{-10}$ less than $5\times10^{-11}$ M, less than $1\times10^{-11}$ M, M, less than $5\times10^{-12}$M, or less than $1\times10^{-12}$M, as measured by biolayer interferometry. In some embodiments, an anti-IL31 antibody binds to canine IL31, feline IL31, or equine IL31 with a Kd of between $5\times10^{-6}$ M and $1\times10^{-6}$ M, between $5\times10^{-6}$ M and $5\times10^{-7}$ M, between $5\times10^{-6}$ M and $1\times10^{-7}$ M, between $5\times10^{-6}$ M and $5\times10^{-8}$M, $5\times10^{-6}$ M and $1\times10^{-8}$M, between $5\times10^{-6}$ M and $5\times10^{-9}$ M, between $5\times10^{-6}$ M and $1\times10^{-9}$ M, between $5\times10^{-6}$ M and $5\times10^{-10}$ M, between $5\times10^{-6}$ M and $1\times10^{-10}$ M, between $5\times10^{-6}$ M and $5\times10^{-11}$M, between $5\times10^{-6}$ M and $1\times10^{-11}$M, between $5\times10^{-6}$ M and $5\times10^{-12}$ M, between $5\times10^{-6}$ M and $1\times10^{-12}$ M, between $1\times10^{-6}$ M and $5\times10^{-7}$M, between $1\times10^{-6}$ M and $1\times10^{-7}$M, between $1\times10^{-6}$ M and $5\times10^{-8}$M, $1\times10^{-6}$ M and $1\times10^{-8}$ M, between $1\times10^{-6}$ M and $5\times10^{-9}$ M, between $1\times10^{-6}$ M and $1\times10^{-9}$ M, between $1\times10^{-6}$ M and $5\times10^{-10}$ M, between $1\times10^{-6}$ M and $1\times10^{-10}$ M, between $1\times10^{-6}$ M and $5\times10^{-11}$M, between $1\times10^{-6}$ M and $1\times10^{-11}$M, between $1\times10^{-6}$ M and $5\times10^{-12}$M, between $1\times10^{-6}$ M and $1\times10^{-12}$ M, between $5\times10^{-7}$ M and $1\times10^{-7}$ M, between $5\times10^{-7}$ M and $5\times10^{-8}$ M, $5\times10^{-7}$ M and $1\times10^{-8}$M, between $5\times10^{-7}$ M and $5\times10^{-9}$M, between $5\times10^{-7}$ M and $1\times10^{-9}$ M, between $5\times10^{-7}$ M and $5\times10^{-10}$ M, between $5\times10^{-7}$ M and $1\times10^{-10}$ M, between $5\times10^{-7}$ M and $5\times10^{-11}$ M, between $5\times10^{-7}$ M and $1\times10^{-11}$ M, between $5\times10^{-7}$ M and $5\times10^{-12}$ M, between $5\times10^{-7}$ M and $1\times10^{-12}$ M, between $1\times10^{-7}$ M and $5\times10^{-8}$M, $1\times10^{-7}$ M and $1\times10^{-8}$ M, between $1\times10^{-7}$ M and $5\times10^{-9}$M, between $1\times10^{-7}$ M and $1\times10^{-9}$M, between $1\times10^{-7}$ M and $5\times10^{-9}$ M, between $1\times10^{-7}$ M and $1\times10^{-10}$ M, between $1\times10^{-7}$ M and $5\times10^{-11}$ M, between $1\times10^{-7}$ M and $1\times10^{-11}$ M, between $1\times10^{-7}$ M and $5\times10^{-12}$ M, between $1\times10^{-7}$ M and $1\times10^{-12}$ M, between $5\times10^{-8}$ M and $1\times10^{-8}$ M, between $5\times10^{-8}$ M and $5\times10^{-9}$M, between $5\times10^{-8}$ M and $1\times10^{-9}$ M, between $5\times10^{-8}$ M and $5\times10^{-10}$ M, between $5\times10^{-8}$ M and $1\times10^{-10}$ M, between $5\times10^{-8}$ M and $5\times10^{-11}$M, between $5\times10^{-8}$ M and $1\times10^{-11}$M, between $5\times10^{-8}$ M and $5\times10^{-12}$ M, between $5\times10^{-8}$ M and $1\times10^{-12}$ M, $1\times10^{-8}$ M and $5\times10^{-9}$M, between $1\times10^{-8}$ M and $1\times10^{-9}$M, between $1\times10^{-8}$ M and $5\times10^{-9}$ M, between $1\times10^{-8}$ M and $1\times10^{-10}$ M, between $1\times10^{-8}$ M and $5\times10^{-11}$ M, between $1\times10^{-8}$ M and $1\times10^{-11}$ M, between $1\times10^{-8}$ M and $5\times10^{-12}$ M, between $1\times10^{-8}$ M and $1\times10^{-12}$ M, between $5\times10^{-9}$ M and $1\times10^{-9}$M, between $5\times10^{-9}$ M and $5\times10^{-10}$ M, between $5\times10^{-9}$ M and $1\times10^{-10}$ M, between $5\times10^{-9}$ M and $5\times10^{-11}$M, between $5\times10^{-9}$ M and $1\times10^{-11}$M, between $5\times10^{-9}$ M and $5\times10^{-12}$ M, between $5\times10^{-9}$ M and $1\times10^{-12}$ M, between $1\times10^{-9}$ M and $5\times10^{-10}$ M, between $1\times10^{-9}$ M and $1\times10^{-10}$ M, between $1\times10^{-9}$M and $5\times10^{-11}$M, between $1\times10^{-9}$ M and $1\times10^{-11}$M, between $1\times10^{-9}$ M and $5\times10^{-12}$M, between $1\times10^{-9}$ M and $1\times10^{-12}$M, between $5\times10^{-10}$ M and $1\times10^{-10}$ M, between $5\times10^{-10}$ M and $5\times10^{-11}$ M, between, $1\times10^{-10}$ M and $5\times10^{-11}$M, $1\times10^{-10}$ M and $1\times10^{-11}$M, between $1\times10^{-10}$ M and $5\times10^{-12}$ M, between $1\times10^{-10}$ M and $1\times10^{-12}$ M, between $5\times10^{-11}$ M and $1\times10^{-12}$ M, between $5\times10^{-11}$ M and $5\times10^{-12}$ M, between $5\times10^{-11}$ M and $1\times10^{-12}$ M, between $1\times10^{-11}$ M and $5\times10^{-12}$ M, or between $1\times10^{-11}$ M and $1\times10^{-12}$ M, as measured by biolayer interferometry. In some embodiments, an anti-IL31 antibody binds to canine IL31 or feline IL31, as determined by immunoblot analysis.

In some embodiments, an anti-IL31 antibody does not bind to human IL31 as determined by immunoblot analysis and/or biolayer interferometry.

In some embodiments, an anti-IL31 antibody is provided that competes with M14 for binding to IL31.

A "variant" means a biologically active polypeptide having at least about 50% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, deleted, at the N- or C-terminus of the polypeptide.

In some embodiments, a variant has at least about 50% amino acid sequence identity, at least about 60% amino acid sequence identity, at least about 65% amino acid sequence identity, at least about 70% amino acid sequence identity, at least about 75% amino acid sequence identity, at least about 80% amino acid sequence identity, at least about 85% amino acid sequence identity, at least about 90% amino acid sequence identity, at least about 95% amino acid sequence identity, at least about 97% amino acid sequence identity, at least about 98% amino acid sequence identity, at least about 99% amino acid sequence identity with the native sequence polypeptide.

In some embodiments, the anti-IL31 antibody comprises:
a) (i) a variable heavy chain sequence having at least 85%, at least 90%, at least 95%, at least 97%, at least 98%, or at least 99% sequence identity to the amino acid sequence of SEQ ID NO: 5, SEQ ID NO: 6, or SEQ ID NO: 7; (ii) a variable light chain sequence having at least 85%, at least 90%, at least 95%, at least 97%, at least 98%, or at least 99% sequence identity to the amino acid sequence of SEQ ID NO: 8, SEQ ID NO: 9, or SEQ ID NO: 10; or (iii) a variable heavy chain sequence as in (i) and a variable light chain sequence as in (ii); or b) (i) a variable heavy chain sequence having at least 85%, at least 90%, at least 95%, at least 97%, at least 98%, or at least 99% sequence identity to the amino acid sequence of SEQ ID NO: 49, SEQ ID NO: 50, SEQ ID NO: 51, or SEQ ID NO: 90; (ii) a variable light chain sequence having at least 85%, at least 90%, at least 95%, at least 98%, or at least 99% sequence identity to the amino acid sequence of SEQ ID NO: 52, SEQ ID NO: 53, or SEQ ID NO: 54; or (iii) a variable heavy chain sequence as in (i) and a variable light chain sequence as in (ii).

As used herein, "percent (%) amino acid sequence identity" and "homology" with respect to a peptide, polypeptide, or antibody sequence are defined as the percentage of amino acid residues in a candidate sequence that are identical with the amino acid residues in the specific peptide or polypeptide sequence, after aligning the sequences and introducing gaps, if necessary to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or MEGALINE™ (DNASTAR) software. Those skilled in the art can determine appropriate parameters for measuring alignment, including any algorithms needed to achieve maximal alignment over the full length of sequences being compared.

An amino acid substitution may include but is not limited to the replacement of one amino acid in a polypeptide with another amino acid. Exemplary substitutions are shown in Table 2. Amino acid substitutions may be introduced into an antibody of interest and the products screened for a desired activity, for example, retained/improved antigen binding, decreased immunogenicity, or improved ADCC or CDC.

TABLE 2

| Original Residue | Exemplary Substitutions |
| --- | --- |
| Ala (A) | Val; Leu; Ile |
| Arg (R) | Lys; Gln; Asn |
| Asn (N) | Gln; His; Asp; Lys; Arg |
| Asp (D) | Glu; Asn |
| Cys (C) | Ser; Ala |
| Gln(Q) | Asn; Glu |
| Glu (E) | Asp; Gln |
| Gly (G) | Ala |
| His (H) | Asn; Gln; Lys; Arg |
| He (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe(F) | Trp; Leu; Val; Ile; Ala; Tyr |
| Pro (P) | Ala |
| Ser(S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes with another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters or enhancers) that regulate the expression of the polypeptide of interest, or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NS0 cells, PER.C6® cells (Crucell), 293 cells, and CHO cells, and their derivatives, such as 293-6E, DG44, CHO-S, and CHO-K cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) encoding an amino acid sequence(s) provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated." In some embodiments, the anti-IL31 antibody is purified using chromatography, such as size exclusion chromatography, ion exchange chromatography, protein A column chromatography, hydrophobic interaction chromatography, and CHT chromatography.

The term "companion animal species" refers to an animal suitable to be a companion to humans. In some embodiments, a companion animal species is a small mammal, such as a canine, feline, dog, cat, horse, rabbit, ferret, guinea pig, rodent, etc. In some embodiments, a companion animal species is a farm animal, such as a horse, cow, pig, etc.

The term "IL31 signaling function" refers to any one of or combination of the downstream activities that occurs when IL31 binds its receptor or receptor complex. In some embodiments, the IL31 signaling function comprises activation of Janus kinase (Jak) 1 or Jak 2 signaling molecules. In some embodiments, the IL31 signaling function comprises phosphorylation of STAT-3 or STAT-5 proteins. In some embodiments, the IL31 signaling function comprises activating the ERK1/2 MAP kinase signaling pathway. In some embodiments, the IL31 signaling function comprises activating the PI3K/AKT signaling pathway. In some embodiments, the IL31 signaling function comprises activating the Jak1/2 signaling pathway.

"STAT phosphorylation" means the post-expression modification of a STAT protein by phosphorylation. For example, "STAT-3 phosphorylation" refers to the phosphorylation of STAT-3 and "STAT-5 phosphorylation" refers to the phosphorylation of STAT-5. In some embodiments, the phosphorylation of STAT-3 is measured by immuno-blot analysis.

For example, cells (e.g., canine monocytic DH82 cells, or mammalian cells (e.g., HeLa cells) transfected with canine and/or feline IL31Ra) are plated into a 96-well cell culture plate at a density of $1 \times 10^5$ cells per well in growth media (e.g., MEM, Life Technologies®) containing 15% heat-inactivated fetal bovine serum, 2 mmol/L GlutaMax, 1 mmol/L sodium pyruvate, and 10 nm/mL canine interferon-c (R&D Systems, Minneapolis, MN, USA) for 24 hours at 37° C. in the presence of anti-IL31 antibody as described herein. Immuno-blot analysis of the cell lysate using anti-phospho STAT-3, anti-STAT-3, anti-phospho STAT-1, anti-STAT-1, anti-phospho STAT-5, or anti-STAT-5 antibodies (R&D Systems) may be used to detect the concentration of phosphorylated STAT protein and unphosphorylated STAT protein relative to each other and compared to a beta-actin control. Methods for determining the concentration of proteins, either qualitatively or quantitatively, by immunoblot are understood by persons of skill in the art. In some embodiments, relative concentration is determined by qualitatively by visual inspection of the immunoblot. In some embodiments, the concentration of phosphorylated STAT protein and unphosphorylated STAT protein is quantitatively determined by digitally imaging an immunoblot, determining the intensity of the bands, and using a linear standard curve of known concentrations of STAT protein to back calculate the concentration of phosphorylated or unphosporylated STAT protein in a sample.

To "reduce" or "inhibit" means to decrease, reduce, or arrest an activity, function, or amount as compared to a reference. In some embodiments, by "reduce" or "inhibit" is meant the ability to cause an overall decrease of 20% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control dose (such as a placebo) over the same period of time. A "reference" as used herein, refers to any sample, standard, or level that is used for comparison purposes. A reference may be obtained from a healthy or non-diseased sample. In some examples, a reference is obtained from a non-diseased or non-treated sample of a companion animal. In some examples, a reference is obtained from one or more healthy animals of a particular species, which are not the animal being tested or treated.

The term "substantially reduced," as used herein, denotes a sufficiently high degree of reduction between a numeric value and a reference numeric value such that one of skill in the art would consider the difference between the two values to be of statistical significance within the context of the biological characteristic measured by said values. In some embodiments, the substantially reduced numeric values is reduced by greater than about any one of 10%, 15% 20%, 25%, 30%, 35%, 40%, 45%, 50%, 60%, 70%, 80%, 90%, or 100% compared to the reference value.

In some embodiments, an IL31 antibody may reduce IL31 signaling function in a companion animal species by at least 10%, at least 15%, at least 20%, at least 25%, at least 30%, at least 35%, at least 40%, at least 45%, at least 50%, at least 60%, at least 70%, at least 80%, at least 90%, or 100% compared to IL31 signaling function in the absence of the antibody, as measured by a reduction in STAT-3 phosphorylation. In some embodiments, the reduction in IL31 signaling function or the reduction in STAT-3 phosphorylation is between 10% and 15%, between 10% and 20%, between 10% and 25%, between 10% and 30%, between 10% and 35%, between 10% and 40%, between 10% and 45%, between 10% and 50%, between 10% and 60%, between 10% and 70%, between 10% and 80%, between 10% and 90%, between 10% and 100%, between 15% and 20%, between 15% and 25%, between 15% and 30%, between 15% and 35%, between 15% and 40%, between 15% and 45%, between 15% and 50%, between 15% and 60%, between 15% and 70%, between 15% and 80%, between 15% and 90%, between 15% and 100%, between 20% and 25%, between 20% and 30%, between 20% and 35%, between 20% and 40%, between 20% and 45%, between 20% and 50%, between 20% and 60%, between 20% and 70%, between 20% and 80%, between 20% and 90%, between 20% and 100%, between 25% and 30%, between 25% and 35%, between 25% and 40%, between 25% and 45%, between 25% and 50%, between 25% and 60%, between 25% and 70%, between 25% and 80%, between 25% and 90%, between 25% and 100%, between 30% and 35%, between 30% and 40%, between 30% and 45%, between 30% and 50%, between 30% and 60%, between 30% and 70%, between 30% and 80%, between 30% and 90%, between 30% and 100%, between 35% and 40%, between 35% and 45%, between 35% and 50%, between 35% and 60%, between 35% and 70%, between 35% and 80%, between 35% and 90%, between 35% and 100%, between 40% and 45%, between 40% and 50%, between 40% and 60%, between 40% and 70%, between 40% and 80%, between 40% and 90%, between 40% and 100%, between 45% and 50%, between 45% and 60%, between 45% and 70%, between 45% and 80%, between 45% and 90%, between 45% and 100%, between 50% and 60%, between 50% and 70%, between 50% and 80%, between 50% and 90%, between 50% and 100%, between 60% and 70%, between 60% and 80%, between 60% and 90%, between 60% and 100%, between 70% and 80%, between 70% and 90%, between 70% and 100%, between 80% and 90%, between 80% and 100%, or between 90% and 100%.

Exemplary Pharmaceutical Compositions

The terms "pharmaceutical formulation" and "pharmaceutical composition" refer to a preparation which is in such form as to permit the biological activity of the active ingredient(s) to be effective, and which contains no additional components that are unacceptably toxic to a subject to which the formulation would be administered.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. Examples of pharmaceutically acceptable carriers include alumina; aluminum stearate; lecithin; serum proteins, such as human serum albumin, canine or other animal albumin; buffers such as phosphate, citrate, tromethamine or HEPES buffers; glycine; sorbic acid; potassium sorbate; partial glyceride mixtures of saturated vegetable fatty acids; water; salts or electrolytes, such as protamine sulfate, disodium hydrogen phosphate, potassium hydrogen phosphate, sodium chloride, zinc salts, colloidal silica, or magnesium trisilicate; polyvinyl pyrrolidone, cellulose-based substances; polyethylene glycol; sucrose; mannitol; or amino acids including, but not limited to, arginine.

The pharmaceutical composition can be stored in lyophilized form. Thus, in some embodiments, the preparation process includes a lyophilization step. The lyophilized composition may then be reformulated, typically as an aqueous composition suitable for parenteral administration, prior to administration to the dog, cat, or horse. In other embodiments, particularly where the antibody is highly stable to thermal and oxidative denaturation, the pharmaceutical composition can be stored as a liquid, i.e., as an aqueous composition, which may be administered directly, or with appropriate dilution, to the dog, cat, or horse. A lyophilized composition can be reconstituted with sterile Water for Injection (WFI). Anti-bacterial agents (e.g., bacteriostatic reagents, such benzyl alcohol, may be included. Thus, the invention provides pharmaceutical compositions in solid or liquid form.

The pH of the pharmaceutical compositions may be in the range of from about pH 5 to about pH 8, when administered. The compositions of the invention are sterile if they are to be used for therapeutic purposes. Sterility can be achieved by any of several means known in the art, including by filtration through sterile filtration membranes (e.g., 0.2 micron membranes). Sterility may be maintained with or without anti-bacterial agents.

Exemplary Uses of Antibodies and Pharmaceutical Compositions

The antibodies or pharmaceutical compositions comprising the antibodies of the invention may be useful for treating an IL-31-induced condition. As used herein, an "IL31-induced condition" means a disease associated with, caused by, or characterized by, elevated levels or altered gradients of IL31 concentration. Such IL31-induced conditions include, but are not limited to, a pruritic or an allergic disease. In some embodiments, the IL31-induced condition is atopic dermatitis, allergic dermatitis, pruritus, asthma, psoriasis, scleroderma, or eczema. An IL31-induced condition may be exhibited in a companion animal, including, but not limited to, canine or feline.

As used herein, "treatment" is an approach for obtaining beneficial or desired clinical results. "Treatment" as used herein, covers any administration or application of a therapeutic for disease in a mammal, including a companion animal. For purposes of this disclosure, beneficial or desired clinical results include, but are not limited to, any one or more of: alleviation of one or more symptoms, diminishment of extent of disease, preventing or delaying spread of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

In some embodiments, an anti-IL31 antibody or pharmaceutical compositions comprising it can be utilized in accordance with the methods herein to treat IL31-induced conditions. In some embodiments, an anti-IL31 antibody or pharmaceutical compositions is administered to a companion animal, such as a canine or a feline, to treat an IL31-induced condition.

A "therapeutically effective amount" of a substance/molecule, agonist or antagonist may vary according to factors such as the type of disease to be treated, the disease state, the severity and course of the disease, the type of therapeutic purpose, any previous therapy, the clinical history, the response to prior treatment, the discretion of the attending veterinarian, age, sex, and weight of the animal, and the ability of the substance/molecule, agonist or antagonist to elicit a desired response in the animal. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic or prophylactic result.

In some embodiments, an anti-IL31 antibody or pharmaceutical composition comprising an anti-IL31 antibody is administered parenterally, by subcutaneous administration, intravenous infusion, or intramuscular injection. In some embodiments, an anti-IL31 antibody or pharmaceutical composition comprising an anti-IL31 antibody is administered as a bolus injection or by continuous infusion over a period of time. In some embodiments, an anti-IL31 antibody or pharmaceutical composition comprising an anti-IL31 antibody is administered by an intramuscular, an intraperitoneal, an intracerebrospinal, a subcutaneous, an intra-arterial, an intrasynovial, an intrathecal, or an inhalation route.

Anti-IL31 antibodies described herein may be administered in an amount in the range of 0.01 mg/kg body weight to 100 mg/kg body weight per dose. In some embodiments, anti-IL31 antibodies may be administered in an amount in the range of 0.5 mg/kg body weight to 50 mg/kg body weight per dose. In some embodiments, anti-IL31 antibodies may be administered in an amount in the range of 0.1 mg/kg body weight to 10 mg/kg body weight per dose. In some embodiments, anti-IL31 antibodies may be administered in an amount in the range of 0.1 mg/kg body weight to 100 mg/kg body weight per dose. In some embodiments, anti-IL31 antibodies may be administered in an amount in the range of 1 mg/kg body weight to 10 mg/kg body weight per dose. In some embodiments, anti-IL31 antibodies may be administered in an amount in the range of 0.5 mg/kg body weight to 100 mg/kg body, in the range of 1 mg/kg body weight to 100 mg/kg body weight, in the range of 5 mg/kg body weight to 100 mg/kg body weight, in the range of 10 mg/kg body weight to 100 mg/kg body weight, in the range of 20 mg/kg body weight to 100 mg/kg body weight, in the range of 50 mg/kg body weight to 100 mg/kg body weight, in the range of 1 mg/kg body weight to 10 mg/kg body weight, in the range of 5 mg/kg body weight to 10 mg/kg body weight, in the range of 0.5 mg/kg body weight to 10 mg/kg body weight, in the range of 0.01 mg/kg body weight to 0.5 mg/kg body weight, in the range of 0.01 mg/kg body weight to 0.1 mg/kg body weight, or in the range of 5 mg/kg body weight to 50 mg/kg body weight.

An anti-IL31 antibody or a pharmaceutical composition comprising an anti-IL31 antibody can be administered to a companion animal at one time or over a series of treatments.

For example, an anti-IL31 antibody or a pharmaceutical composition comprising an anti-IL31 antibody may be administered at least once, more than once, at least twice, at least three times, at least four times, or at least five times.

In some embodiments, the dose is administered once per week for at least two or three consecutive weeks, and in some embodiments, this cycle of treatment is repeated two or more times, optionally interspersed with one or more weeks of no treatment. In other embodiments, the therapeutically effective dose is administered once per day for two to five consecutive days, and in some embodiments, this cycle of treatment is repeated two or more times, optionally interspersed with one or more days or weeks of no treatment.

Administration "in combination with" one or more further therapeutic agents includes simultaneous (concurrent) and consecutive or sequential administration in any order. The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes. The term "sequentially" is used herein to refer to administration of two or more therapeutic agents where the administration of one or more agent(s) continues after discontinuing the administration of one or more other agent(s), or wherein administration of one or more agent(s) begins before the administration of one or more other agent(s). For example, administration of the two or more therapeutic agents are administered with a time separation of more than about a specified number of minutes. As used herein, "in conjunction with" refers to administration of one treatment modality in addition to another treatment modality. As such, "in conjunction with" refers to administration of one treatment modality before, during or after administration of the other treatment modality to the animal.

In some embodiments, the method comprises administering in combination with an anti-IL31 antibody or a pharmaceutical composition comprising an anti-IL31 antibody, a Jak inhibitor, a PI3K inhibitor, an AKT inhibitor, or a MAPK inhibitor. In some embodiments, the method comprises administering in combination with an anti-IL31 antibody or a pharmaceutical composition comprising an anti-IL31 antibody, an anti-IL17 antibody, an anti-TNFα antibody, an anti-CD20 antibody, an anti-CD19 antibody, an anti-CD25 antibody, an anti-IL4 antibody, an anti-IL13 antibody, an anti-IL23 antibody, an anti-IgE antibody, an anti-CD11a antibody, anti-IL6R antibody, anti-α4-Intergrin antibody, an anti-IL12 antibody, an anti-IL1β antibody, or an anti-BlyS antibody.

Provided herein are methods of exposing to a cell an anti-IL31 antibody or a pharmaceutical composition comprising an anti-IL31 antibody under conditions permissive for binding of the antibody to IL31. In some embodiments, the cell is exposed to the antibody or pharmaceutical composition ex vivo. In some embodiments, the cell is exposed to the antibody or pharmaceutical composition in vivo. In some embodiments, a cell is exposed to the anti-IL31 antibody or the pharmaceutical composition under conditions permissive for binding of the antibody to intracellular IL31. In some embodiments, a cell is exposed to the anti-IL31 antibody or the pharmaceutical composition under conditions permissive for binding of the antibody to extracellular IL31. In some embodiments, a cell may be exposed in vivo to the anti-IL31 antibody or the pharmaceutical composition by any one or more of the administration methods described herein, including but not limited to, intraperitoneal, intramuscular, intravenous injection into the subject. In some embodiments, a cell may be exposed ex vivo to the anti-IL31 antibody or the pharmaceutical composition by exposing the cell to a culture medium comprising the antibody or the pharmaceutical composition. In some embodiments, the permeability of the cell membrane may be affected by the use of any number of methods understood by those of skill in the art (such as electroporating the cells or exposing the cells to a solution containing calcium chloride) before exposing the cell to a culture medium comprising the antibody or the pharmaceutical composition.

In some embodiments, the binding results in a reduction of IL31 signaling function by the cell. In some embodiments, an IL31 antibody may reduce IL31 signaling function in a cell by at least 10%, at least 15%, at least 20%, at least 25%, at least 30%, at least 35%, at least 40%, at least 45%, at least 50%, at least 60%, at least 70%, at least 80%, at least 90%, or 100% compared to IL31 signaling function in the absence of the antibody, as measured by a reduction in STAT-3 phosphorylation. In some embodiments, the reduction in IL31 signaling function or the reduction in STAT-3 phosphorylation is between 10% and 15%, between 10% and 20%, between 10% and 25%, between 10% and 30%, between 10% and 35%, between 10% and 40%, between 10% and 45%, between 10% and 50%, between 10% and 60%, between 10% and 70%, between 10% and 80%, between 10% and 90%, between 10% and 100%, between 15% and 20%, between 15% and 25%, between 15% and 30%, between 15% and 35%, between 15% and 40%, between 15% and 45%, between 15% and 50%, between 15% and 60%, between 15% and 70%, between 15% and 80%, between 15% and 90%, between 15% and 100%, between 20% and 25%, between 20% and 30%, between 20% and 35%, between 20% and 40%, between 20% and 45%, between 20% and 50%, between 20% and 60%, between 20% and 70%, between 20% and 80%, between 20% and 90%, between 20% and 100%, between 25% and 30%, between 25% and 35%, between 25% and 40%, between 25% and 45%, between 25% and 50%, between 25% and 60%, between 25% and 70%, between 25% and 80%, between 25% and 90%, between 25% and 100%, between 30% and 35%, between 30% and 40%, between 30% and 45%, between 30% and 50%, between 30% and 60%, between 30% and 70%, between 30% and 80%, between 30% and 90%, between 30% and 100%, between 35% and 40%, between 35% and 45%, between 35% and 50%, between 35% and 60%, between 35% and 70%, between 35% and 80%, between 35% and 90%, between 35% and 100%, between 40% and 45%, between 40% and 50%, between 40% and 60%, between 40% and 70%, between 40% and 80%, between 40% and 90%, between 40% and 100%, between 45% and 50%, between 45% and 60%, between 45% and 70%, between 45% and 80%, between 45% and 90%, between 45% and 100%, between 50% and 60%, between 50% and 70%, between 50% and 80%, between 50% and 90%, between 50% and 100%, between 60% and 70%, between 60% and 80%, between 60% and 90%, between 60% and 100%, between 70% and 80%, between 70% and 90%, between 70% and 100%, between 80% and 90%, between 80% and 100%, or between 90% and 100%.

Provided herein are methods of using the anti-IL31 antibodies, polypeptides and polynucleotides for detection, diagnosis and monitoring of an IL31-induced condition. Provided herein are methods of determining whether a companion animal will respond to anti-IL31 antibody therapy. In some embodiments, the method comprises detecting whether the animal has cells that express IL31 using an anti-IL31 antibody. In some embodiments, the method of detection comprises contacting the sample with an antibody, polypeptide, or polynucleotide and determining whether the level of binding differs from that of a reference or comparison sample (such as a control). In some embodiments, the method may be useful to determine whether the antibodies or polypeptides described herein are an appropriate treatment for the subject animal.

In some embodiments, the sample is a biological sample. The term "biological sample" means a quantity of a substance from a living thing or formerly living thing. In some embodiments, the biological sample is a cell or cell/tissue lysate. In some embodiments, the biological sample includes, but is not limited to, blood, (for example, whole blood), plasma, serum, urine, synovial fluid, and epithelial cells.

In some embodiments, the cells or cell/tissue lysate are contacted with an anti-IL31 antibody and the binding between the antibody and the cell is determined. When the test cells show binding activity as compared to a reference cell of the same tissue type, it may indicate that the subject would benefit from treatment with an anti-IL31 antibody. In some embodiments, the test cells are from tissue of a companion animal.

Various methods known in the art for detecting specific antibody-antigen binding can be used. Exemplary immunoassays which can be conducted include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. Appropriate labels include, without limitation, radionuclides (for example $^{125}$I, $^{131}$I, $^{35}$S, $^{3}$H, or $^{32}$P), enzymes (for example, alkaline phosphatase, horseradish peroxidase, luciferase, or p-glactosidase), fluorescent moieties or proteins (for example, fluorescein, rhodamine, phycoerythrin, GFP, or BFP), or luminescent moieties (for example, Qdot™ nanoparticles supplied by the Quantum Dot Corporation, Palo Alto, Calif.). General techniques to be used in performing the various immunoassays noted above are known to those of ordinary skill in the art.

For purposes of diagnosis, the polypeptide including antibodies can be labeled with a detectable moiety including but not limited to radioisotopes, fluorescent labels, and various enzyme-substrate labels know in the art. Methods of conjugating labels to an antibody are known in the art. In some embodiments, the anti-IL31 antibodies need not be labeled, and the presence thereof can be detected using a second labeled antibody which binds to the first anti-IL31 antibody. In some embodiments, the anti-IL31 antibody can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987). The anti-IL31 antibodies and polypeptides can also be used for in vivo diagnostic assays, such as in vivo imaging. Generally, the antibody or the polypeptide is labeled with a radionuclide (such as $^{111}$In, $^{99}$Tc, $^{14}$C, $^{131}$I, $^{125}$I, $^{3}$H, or any other radionuclide label, including those outlined herein) so that the cells or tissue of interest can be localized using immunoscintiography. The antibody may also be used as staining reagent in pathology using techniques well known in the art.

In some embodiments, a first antibody is used for a diagnostic and a second antibody is used as a therapeutic. In some embodiments, the first and second antibodies are different. In some embodiments, the first and second antibodies can both bind to the antigen at the same time, by binding to separate epitopes.

The following examples illustrate particular aspects of the disclosure and are not intended in any way to limit the disclosure.

EXAMPLES

Example 1: In Vitro Affinity Maturation for Enhanced Binding to IL31

The variable heavy chain (VH) and variable light chain (VL) sequences of mouse monoclonal antibody M14 raised against IL-31 were identified (SEQ ID NOs: 1 and 2). See WO 2018/156367, which is incorporated by reference herein in its entirety for any purpose. The M14 VH and VL sequences were caninized (SEQ ID NOs: 3 and 4) by searching and selecting proper canine germline antibody sequences as a template for CDR grafting, followed by protein modeling.

A phage library of variant Fab polypeptides having mutations within and around the CDRs of caninized M14 VH and VL sequences (SEQ ID NOs 3 and 4) was prepared and screened for slower $k_{off}$ rate by a canine IL31 dissociation assay. After three rounds of panning the phage library against canine IL31, phage colonies expressing variant Fab polypeptides potentially having enhanced canine IL31 binding were identified and the polypeptides sequenced.

Single *E. coli* colonies expressing each of the identified variant Fab polypeptides with an SASA tag were cultured and induced to express the polypeptides. Cell culture media containing the variant Fab polypeptides was exposed to immobilized BSA either on a plate or a Biacore chip. The plates or chips with bound variant Fab polypeptides were exposed to soluble canine IL31 to screen for slow $k_{off}$ rate.

Three lead caninized, matured variable heavy chain polypeptides (cmVH1 (SEQ ID NO: 5), cmVH2 (SEQ ID NO: 6), and cmVH3 (SEQ ID NO: 7)) and three caninized, matured light chain polypeptides (cmVL1 (SEQ ID NO: 8), cmVL2 (SEQ ID NO: 9), and cmVL3 (SEQ ID NO: 10)) were selected. Exemplary CDR sequences for the lead caninized, matured variable chains are represented by SEQ ID NOs: 11, 12, 13, 14, 15, 20, 21, 22, 23, and 24, and framework region sequences are represented by SEQ ID NOs: 16, 17, 18, 19, 25, 26, 27, and 28.

Chimeric antibodies composed of different combinations of cmVH1, cmVH2, or cmVH3 fused to human IgG1 heavy chain and cmVL1, cmVL2, and cmVL3 fused to human kappa constant light chain were generated. Caninized VH of M14 (SEQ ID NO: 3) fused to human IgG1 heavy chain and caninized VL of M14 (SEQ ID NO: 4) fused to human kappa constant light chain was also generated. Affinity of canine IL31 to the different chimeric antibodies was measured using a BIAcore 8K, as described in Table 3 below:

TABLE 3

| Materials and Methods | |
| --- | --- |
| Instrument | BIAcore 8K |
| Sensor chip | Series S Sensor Chip Protein A |
| Running buffer | 1× HBS-EP+ (10 mM HEPES, 150 mM NaCl, 3 mM EDTA, 0.05% P20, pH 7.4) |
| Ligand | Canine IL31 |
| Chimeric antibody analytes | 1. Caninized VH-VL M14 |
| | 2. cmVH1 + cmVL1 |
| | 3. cmVH2 + cmVL2 |
| | 4. cmVH2 + cmVL3 |
| | 5. cmVH3 + cmVL2 |
| | 6. cmVH3 + cmVL3 |
| Immobilization level (RU) | ~200 |
| Association contact time (s) | 180 |
| Dissociation contact time (s) | 600 |
| Flow rate (μl/min) | 30 |
| Sample concentrations (nM) | 3.125, 6.25, 12.5, 25, 50, 100 |

The affinity and kinetics of each of the chimeric antibodies tested to canine IL31 is summarized in Table 4, below. Each of the affinity matured antibodies tested (analytes 2-6) exhibited higher affinity (as evidenced by the lower Kd value) and a slower off rate (as evidenced by the lower $k_{off}$ value) compared to the caninized VH-VL M14 antibody control (analyte 1).

TABLE 4

| Analyte | $k_{on}$ (1/Ms) | $k_{off}$ (1/s) | Kd (M) | Rmax | Chi$^2$ (RU$^2$) |
| --- | --- | --- | --- | --- | --- |
| 1. Caninized VH-VL M14 | $2.40 \times 10^5$ | $5.23 \times 10^{-4}$ | $2.18 \times 10^{-9}$ | 49.2 | $6.99 \times 10^{-2}$ |
| 2. cmVH1 + cmVL1 | $2.28 \times 10^5$ | $1.82 \times 10^{-4}$ | $8.00 \times 10^{-10}$ | 32 | $2.93 \times 10^{-2}$ |
| 3. cmVH2 + cmVL2 | $1.74 \times 10^5$ | $1.59 \times 10^{-4}$ | $9.14 \times 10^{-10}$ | 34.7 | $2.36 \times 10^{-2}$ |
| 4. cmVH2 + cmVL3 | $1.86 \times 10^5$ | $1.62 \times 10^{-4}$ | $8.68 \times 10^{-10}$ | 33.8 | $1.45 \times 10^{-2}$ |
| 5. cmVH3 + cmVL2 | $1.87 \times 10^5$ | $1.68 \times 10^{-4}$ | $9.00 \times 10^{-10}$ | 35.9 | $3.59 \times 10^{-2}$ |
| 6. cmVH3 + cmVL3 | $2.16 \times 10^5$ | $1.85 \times 10^{-4}$ | $8.58 \times 10^{-10}$ | 32.1 | $3.05 \times 10^{-2}$ |

Example 2: Mutations with Enhanced Binding to Feline IL31

The six chimeric antibodies tested for affinity to canine IL-31 in Tables 3 and 4 (above) were also tested for affinity to feline IL31. The binding analysis was performed using a biosensor OctetRed as follows. Briefly, feline IL31 was biotinylated. The free unreacted biotin was removed from biotinylated IL31 by extensive dialysis. Biotinylated feline IL31 was captured on streptavidin sensor tips. The association of antibody (20 ug/mL) and feline IL31 was monitored for 300 seconds. Dissociation was monitored for 300 seconds. The buffer for dilutions and all binding steps was: 20 mM phosphate, 150 mM NaCl, pH 7.2. The results of the binding analysis are shown in FIG. 2. The affinity of the tested antibodies was ranked as: (cmVH3+cmVL2) or (cmVH3+cmVL3)>(cmVH2+cmVL3)>(cmVH2+cmVL2)> (cmVH1+cmVL1)>(Caninized VH-VL M14).

Example 3: Caninized, Matured Variable Chains with Canine Constant Domains

The caninized, matured VH (e.g., SEQ ID NOs: 5, 6, and 7) and VL (e.g., SEQ ID NOs: 8, 9, and 10) may be fused to a canine IgG-A, IgG-B, IgG-C, or IgG-D heavy chain constant domain (e.g., SEQ ID NOs: 83, 84, 85, and 86) and a canine kappa light chain constant domain (e.g., SEQ ID NO: 87), respectively. Exemplary caninized, matured heavy and light chain sequences having a canine constant domain include SEQ ID NOs: 34, 35, 36, 37, 38, 39, 40, 41, 42, 43, 44, 45, 46, 47, and 48.

Example 4: Felinization and Expression of Affinity Enhanced Variable Heavy and Light Chains Affinity enhanced variable heavy and light chains (e.g., cmVH1-3 and cmVL1-3) may be felinized using methods understood in the art. For example, cmVH2 (SEQ ID NO: 6) was felinized to exemplary SEQ ID NO: 90; cmVH3 (SEQ ID NO: 7) was felinized to exemplary SEQ ID NOs: 49, 50, and 51; and cmVL3 (SEQ ID NO: 10) was felinized to any one of SEQ ID NOs: 52, 53, and 54. The felinized VH and VL may be expressed with a feline IgG heavy chain constant domain (e.g., SEQ ID NO: 88) and a feline kappa light chain constant domain (e.g., SEQ ID NO: 89), respectively. Exemplary felinized, matured heavy and light chain sequences having a feline constant region include SEQ ID NOs: 73, 74, 75, 91, 76, 77, and 78.

DNA sequences encoding a felinized IL-31 antibody having the heavy chain of SEQ ID NO: 91 (VH2) and the light chain of SEQ ID NO: 78 (VL3c) were expressed in mammalian cells and purified. Using the cell-based assay of Example 5, the felinized VH2-VL3 IL31 antibody quantitatively blocked feline IL31-induced STAT3-phosphorylation in both feline IL31R- and canine IL31R-transfected HeLa cells.

Example 5: Development of Canine IL31 Cell-Based Signaling Assay

HeLa cell line, a human epithelial cell line (American Type Culture Collection (ATCC), Catalog No. CCL-2), was purchased and cultured in ATCC-formulated Eagle's Minimum Essential Medium (ATCC, Catalog No. 30-2033) supplemented with 10% fetal bovine serum (FBS) (ATCC, Catalog No. 30-2020). HeLa cells stably transfected with canine or feline IL31Ra-FLAG expression plasmid (pcDNA3.1 canine IL31Ra FLAG (SEQ ID NO: 92) or pcDNA3.1 feline IL31Ra-FLAG (SEQ ID NO: 93) were generated using lipofectamine method (Thermo Fisher, Catalog No. 11668027) and selected for G418-resistant transfectants (Thermo Fisher Catalog No. 10131035) using G418 at a final concentration of 400 μg/mL. G418-resistant clones were screened for STAT1, STAT3, and STAT5 phosphorylation in response to canine IL31 or feline IL31 inductions by Western blotting. The IL31Ra stably transfected HeLa clones that responded to IL31 inductions were used for subsequent studies.

Canine or feline IL31-mediated STAT protein phosphorylation was carried out by seeding HeLa/IL31Ra cells at 10e5 cells per well in 96-well plates and incubated at 37° C., 5% $CO_2$ overnight (in 10% FBS D-MEM as recommended by ATCC). Serum starvation of cells was achieved by replacing medium in each well with medium without FBS supplementation for 1 hour at 5% $CO_2$, 37° C. Serial-diluted anti-IL31 antibody was pre-incubated with IL31 cytokine for 1 hour before addition to serum-starved cells in each well of a 96-well plate for 5 minutes at room temperature. Then, 20 µL of stop solution (M-PER from Thermo Fisher, Catalog No. 78501) was added to each well to lyse the cells. Cell lysates were separated by SDS-PAGE (4-12% Bis-Tris Gel, Invitrogen, Catalog No. NP0329). The IL31-inducible STAT phosphorylation was assayed by Western blotting using either anti-phospho-STAT3 antibody (RnD, Catalog No. AF 4607), anti-phospho-STAT1 antibody (Cell Signaling, Catalog No. 7649), or anti-phospho-STATS antibody (Cell Signaling Catalog No. 9359).

Surprisingly, expression of a canine or feline co-receptor OSMR was not necessary for IL31 signaling.

---

The invention claimed is:

1. An antibody that binds to canine IL31 or feline IL31, wherein the antibody comprises:

a) a heavy chain comprising a CDR1 comprising the amino acid sequence of SEQ ID NO: 11, a CDR2 comprising the amino acid sequence of SEQ ID NO: 12, and a CDR3 comprising the amino acid sequence of SEQ ID NO: 14 or SEQ ID NO: 15; and b) a light chain comprising a CDR1 comprising the amino acid sequence of SEQ ID NO: 20, a CDR2 comprising the amino acid sequence of SEQ ID NO: 21, and a CDR3 comprising the amino acid sequence of SEQ ID NO: 23 or SEQ ID NO: 24.

2. The antibody of claim 1, wherein the antibody comprises:

a) a heavy chain comprising a CDR1 comprising the amino acid sequence of SEQ ID NO: 11, a CDR2 comprising the amino acid sequence of SEQ ID NO: 12, and a CDR3 comprising the amino acid sequence of SEQ ID NO: 15; and b) a light chain comprising a CDR1 comprising the amino acid sequence of SEQ ID NO: 20, a CDR2 comprising the amino acid sequence of SEQ ID NO: 21, and a CDR3 comprising the amino acid sequence of SEQ ID NO: 24.

3. The antibody of claim 1 comprising a heavy chain variable region comprising the amino acid sequence of SEQ ID NO: 6 or SEQ ID NO: 7.

4. The antibody of claim 1 comprising a light chain variable region comprising the amino acid sequence of SEQ ID NO: 9 or SEQ ID NO: 10.

5. The antibody of claim 1, wherein the antibody comprises:

a) a heavy chain comprising a CDR1 comprising the amino acid sequence of SEQ ID NO: 11, a CDR2 comprising the amino acid sequence of SEQ ID NO: 12, and a CDR3 comprising the amino acid sequence of SEQ ID NO: 15; and b) a light chain comprising a CDR1 comprising the amino acid sequence of SEQ ID NO: 20, a CDR2 comprising the amino acid sequence of SEQ ID NO: 21, and a CDR3 comprising the amino acid sequence of SEQ ID NO: 24;

wherein the antibody comprises a heavy chain variable region comprising an amino acid sequence with at least 95% identity to SEQ ID NO: 7 and a light chain variable region comprising an amino acid sequence with at least 95% identity to SEQ ID NO: 10.

6. The antibody of claim 5, wherein the antibody comprises a heavy chain variable region comprising an amino acid sequence with at least 98% identity to SEQ ID NO: 7 and a light chain variable region comprising an amino acid sequence with at least 98% identity to SEQ ID NO: 10.

7. The antibody of claim 5, wherein the antibody comprises a heavy chain variable region comprising an amino acid sequence with at least 99% identity to SEQ ID NO: 7 and a light chain variable region comprising an amino acid sequence with at least 99% identity to SEQ ID NO: 10.

8. The antibody of claim 5, wherein the antibody comprises a heavy chain variable region comprising the amino acid sequence of SEQ ID NO: 7 and a light chain variable region comprising the amino acid sequence of SEQ ID NO: 10.

9. The antibody of claim 1 comprising a heavy chain variable region comprising the amino acid sequence of SEQ ID NO: 49, SEQ ID NO: 50, SEQ ID NO: 51, or SEQ ID NO: 90.

10. The antibody of claim 1 comprising a light chain variable region comprising the amino acid sequence of SEQ ID NO: 52, SEQ ID NO: 53, or SEQ ID NO: 54.

11. A bispecific antibody comprising the antibody of claim 1 and an antibody that binds to an antigen selected from IL17, TNFα, CD20, CD19, CD25, IL4, IL13, IL23, IgE, CD11α, IL6R, α4-Intergrin, IL12, IL1β, and BlyS.

12. A pharmaceutical composition comprising the antibody of claim 1 and a pharmaceutically acceptable carrier.

13. A method of treating a canine or feline having an IL31-induced condition, the method comprising administering to the canine or feline a therapeutically effective amount of the pharmaceutical composition of claim 12, wherein the IL31-induced condition is selected from atopic dermatitis, allergic dermatitis, pruritus, asthma, psoriasis, scleroderma, and eczema.

14. A method of reducing IL31 signaling function in a cell expressing an IL31 receptor, the method comprising exposing to the cell the pharmaceutical composition of claim 12 in the presence of the IL31.

15. A method of treating a canine or feline having an IL31-induced condition, the method comprising administering to the canine or feline a therapeutically effective amount of the antibody of claim 1, wherein the IL31-induced condition is selected from atopic dermatitis, allergic dermatitis, pruritus, asthma, psoriasis, scleroderma, and eczema.

16. A method of reducing IL31 signaling function in a cell expressing an IL31 receptor, the method comprising exposing to the cell the antibody of claim 1 in the presence of the IL31.

17. A method for detecting IL31 in a sample from a canine or feline comprising contacting the sample with the antibody of claim 1 under conditions permissive for binding of the antibody to IL31, and detecting a complex formed between the antibody and IL31 in the sample.

18. An isolated nucleic acid encoding the antibody of claim 1.

19. A host cell comprising the nucleic acid of claim 18.

20. A method of producing the antibody encoded by the nucleic acid of claim 18, comprising culturing a host cell transformed or transfected with the nucleic acid, and isolating the antibody.

* * * * *

SEQUENCE LISTING

```
<160> NUMBER OF SEQ ID NOS: 93

<210> SEQ ID NO 1
<211> LENGTH: 111
<212> TYPE: PRT
<213> ORGANISM: Artificial Sequence
<220> FEATURE:
<223> OTHER INFORMATION: Synthetic: Variable light chain amino acid
      sequence of mouse antibody clone M14

<400> SEQUENCE: 1

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Thr Tyr
            20                  25                  30

Gly Asn Ser Phe Met His Trp Tyr Gln Gln Lys Ser Gly Gln Ser Pro
        35                  40                  45

Lys Leu Leu Ile Tyr Arg Ala Ser Asn Leu Glu Ser Gly Ile Pro Ala
    50                  55                  60

Arg Phe Gly Gly Ser Gly Ser Arg Thr Asp Phe Thr Leu Thr Ile Asp
65                  70                  75                  80

Pro Val Glu Ala Asp Asp Val Ala Thr Tyr Tyr Cys Gln Gln Ser Tyr
                85                  90                  95

Glu Asp Pro Trp Thr Phe Gly Gly Gly Thr Lys Leu Glu Ile Lys
            100                 105                 110

<210> SEQ ID NO 2
<211> LENGTH: 118
<212> TYPE: PRT
<213> ORGANISM: Artificial Sequence
<220> FEATURE:
<223> OTHER INFORMATION: Synthetic: Variable heavy chain amino acid
      sequence of mouse antibody clone M14

<400> SEQUENCE: 2

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ile Thr Asp Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Ser Val Thr Val Ser Ser
            115
```

```
<210> SEQ ID NO 3
<211> LENGTH: 118
<212> TYPE: PRT
<213> ORGANISM: Artificial Sequence
<220> FEATURE:
<223> OTHER INFORMATION: Synthetic: Exemplary caninized variable heavy
      chain amino acid sequence of mouse antibody clone M14

<400> SEQUENCE: 3

Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Ser Val Thr Val Ser Ser
        115

<210> SEQ ID NO 4
<211> LENGTH: 111
<212> TYPE: PRT
<213> ORGANISM: Artificial Sequence
<220> FEATURE:
<223> OTHER INFORMATION: Synthetic: Exemplary caninized variable light
      chain amino acid sequence of mouse antibody clone M14

<400> SEQUENCE: 4

Asp Ile Val Met Thr Gln Ser Pro Ala Ser Leu Ser Val Ser Leu Gly
1               5                   10                  15

Gln Arg Ala Thr Ile Ser Cys Arg Ala Ser Glu Ser Val Asp Thr Tyr
            20                  25                  30

Gly Asn Ser Phe Met His Trp Tyr Gln Gln Lys Pro Gly Gln Ser Pro
        35                  40                  45

Lys Leu Leu Ile Tyr Arg Ala Ser Asn Leu Glu Ser Gly Ile Pro Ala
    50                  55                  60

Arg Phe Gly Gly Ser Gly Ser Gly Thr Asp Phe Thr Leu Thr Ile Asp
65                  70                  75                  80

Pro Val Gln Ala Asp Asp Val Ala Thr Tyr Tyr Cys Gln Gln Ser Tyr
                85                  90                  95

Glu Asp Pro Trp Thr Phe Gly Gly Gly Thr Lys Leu Glu Ile Lys
            100                 105                 110

<210> SEQ ID NO 5
<211> LENGTH: 118
<212> TYPE: PRT
<213> ORGANISM: Artificial Sequence
<220> FEATURE:
<223> OTHER INFORMATION: Synthetic: Exemplary caninized, matured
      variable heavy chain sequence cmVH1  N35K

<400> SEQUENCE: 5
```

```
Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Lys Trp Ile Arg Lys Phe Pro Gly Asn Lys Leu Glu Tyr Met
            35                  40                  45

Gly Tyr Ile Ser Tyr Ser Gly Ile Thr Asp Tyr Asn Pro Ser Leu Lys
        50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Ser Val Thr Val Ser Ser
        115

<210> SEQ ID NO 6
<211> LENGTH: 118
<212> TYPE: PRT
<213> ORGANISM: Artificial Sequence
<220> FEATURE:
<223> OTHER INFORMATION: Synthetic: Exemplary caninized, matured
      variable heavy chain sequence cmVH2  N35K G99P

<400> SEQUENCE: 6

Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Lys Trp Ile Arg Lys Phe Pro Gly Asn Lys Leu Glu Tyr Met
            35                  40                  45

Gly Tyr Ile Ser Tyr Ser Gly Ile Thr Asp Tyr Asn Pro Ser Leu Lys
        50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Pro Asn Tyr Gly Tyr Ala Met Asp Tyr Trp Gly Gln Gly Thr
            100                 105                 110

Ser Val Thr Val Ser Ser
        115

<210> SEQ ID NO 7
<211> LENGTH: 118
<212> TYPE: PRT
<213> ORGANISM: Artificial Sequence
<220> FEATURE:
<223> OTHER INFORMATION: Synthetic: Exemplary caninized, matured
      variable heavy chain sequence cmVH3  N35K G99A

<400> SEQUENCE: 7

Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Lys Trp Ile Arg Lys Phe Pro Gly Asn Lys Leu Glu Tyr Met
            35                  40                  45
```

```
Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Ala Asn Tyr Gly Tyr Ala Met Asp Tyr Trp Gly Gln Gly Thr
                100                 105                 110

Ser Val Thr Val Ser Ser
        115
```

```
<210> SEQ ID NO 8
<211> LENGTH: 111
<212> TYPE: PRT
<213> ORGANISM: Artificial Sequence
<220> FEATURE:
<223> OTHER INFORMATION: Synthetic: Exemplary caninized, matured
      variable light chain sequence cmVL1  N34R

<400> SEQUENCE: 8

Asp Ile Val Met Thr Gln Ser Pro Ala Ser Leu Ser Val Ser Leu Gly
1               5                   10                  15

Gln Arg Ala Thr Ile Ser Cys Arg Ala Ser Glu Ser Val Asp Thr Tyr
                20                  25                  30

Gly Arg Ser Phe Met His Trp Tyr Gln Gln Lys Pro Gly Gln Ser Pro
            35                  40                  45

Lys Leu Leu Ile Tyr Arg Ala Ser Asn Leu Glu Ser Gly Ile Pro Ala
    50                  55                  60

Arg Phe Gly Gly Ser Gly Ser Gly Thr Asp Phe Thr Leu Thr Ile Asp
65                  70                  75                  80

Pro Val Gln Ala Asp Asp Val Ala Thr Tyr Tyr Cys Gln Gln Ser Tyr
                85                  90                  95

Glu Asp Pro Trp Thr Phe Gly Gly Gly Thr Lys Leu Glu Ile Lys
                100                 105                 110
```

```
<210> SEQ ID NO 9
<211> LENGTH: 111
<212> TYPE: PRT
<213> ORGANISM: Artificial Sequence
<220> FEATURE:
<223> OTHER INFORMATION: Synthetic: Exemplary caninized, matured
      variable light chain sequence cmVL2  N34R Q93Y

<400> SEQUENCE: 9

Asp Ile Val Met Thr Gln Ser Pro Ala Ser Leu Ser Val Ser Leu Gly
1               5                   10                  15

Gln Arg Ala Thr Ile Ser Cys Arg Ala Ser Glu Ser Val Asp Thr Tyr
                20                  25                  30

Gly Arg Ser Phe Met His Trp Tyr Gln Gln Lys Pro Gly Gln Ser Pro
            35                  40                  45

Lys Leu Leu Ile Tyr Arg Ala Ser Asn Leu Glu Ser Gly Ile Pro Ala
    50                  55                  60

Arg Phe Gly Gly Ser Gly Ser Gly Thr Asp Phe Thr Leu Thr Ile Asp
65                  70                  75                  80

Pro Val Gln Ala Asp Asp Val Ala Thr Tyr Tyr Cys Tyr Gln Ser Tyr
                85                  90                  95

Glu Asp Pro Trp Thr Phe Gly Gly Gly Thr Lys Leu Glu Ile Lys
                100                 105                 110
```

-continued

```
<210> SEQ ID NO 10
<211> LENGTH: 111
<212> TYPE: PRT
<213> ORGANISM: Artificial Sequence
<220> FEATURE:
<223> OTHER INFORMATION: Synthetic: Exemplary caninized, matured
      variable light chain sequence cmVL3  N34R Q93H

<400> SEQUENCE: 10

Asp Ile Val Met Thr Gln Ser Pro Ala Ser Leu Ser Val Ser Leu Gly
1               5                   10                  15

Gln Arg Ala Thr Ile Ser Cys Arg Ala Ser Glu Ser Val Asp Thr Tyr
            20                  25                  30

Gly Arg Ser Phe Met His Trp Tyr Gln Gln Lys Pro Gly Gln Ser Pro
        35                  40                  45

Lys Leu Leu Ile Tyr Arg Ala Ser Asn Leu Glu Ser Gly Ile Pro Ala
    50                  55                  60

Arg Phe Gly Gly Ser Gly Ser Gly Thr Asp Phe Thr Leu Thr Ile Asp
65                  70                  75                  80

Pro Val Gln Ala Asp Asp Val Ala Thr Tyr Tyr Cys His Gln Ser Tyr
                85                  90                  95

Glu Asp Pro Trp Thr Phe Gly Gly Gly Thr Lys Leu Glu Ile Lys
            100                 105                 110

<210> SEQ ID NO 11
<211> LENGTH: 9
<212> TYPE: PRT
<213> ORGANISM: Artificial Sequence
<220> FEATURE:
<223> OTHER INFORMATION: Synthetic: CDR-H1 of cmVH1, cmVH2, and cmVH3

<400> SEQUENCE: 11

Gly Asp Ser Ile Thr Ser Gly Tyr Trp
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic: CDR-H2 of cmVH1, cmVH2, and cmVH3

<400> SEQUENCE: 12

Tyr Ile Ser Tyr Ser Gly Ile Thr Asp Tyr
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic: CDR-H3  of cmVH1

<400> SEQUENCE: 13

Ala Arg Tyr Gly Asn Tyr Gly Tyr Ala Met Asp Tyr
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic: CDR-H3 of cmVH2
```

-continued

```
<400> SEQUENCE: 14

Ala Arg Tyr Pro Asn Tyr Gly Tyr Ala Met Asp Tyr
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic: CDR-H3 of cmVH3

<400> SEQUENCE: 15

Ala Arg Tyr Ala Asn Tyr Gly Tyr Ala Met Asp Tyr
1               5                   10

<210> SEQ ID NO 16
<211> LENGTH: 25
<212> TYPE: PRT
<213> ORGANISM: Artificial Sequence
<220> FEATURE:
<223> OTHER INFORMATION: Synthetic: HC-FR1 of cmVH1, cmVH2, and cmVH3

<400> SEQUENCE: 16

Glu Val Gln Leu Gln Glu Ser Gly Pro Ser Leu Val Lys Pro Ser Gln
1               5                   10                  15

Thr Leu Ser Leu Thr Cys Ser Val Thr
            20                  25

<210> SEQ ID NO 17
<211> LENGTH: 15
<212> TYPE: PRT
<213> ORGANISM: Artificial Sequence
<220> FEATURE:
<223> OTHER INFORMATION: Synthetic: HC-FR2 of cmVH1, cmVH2, and cmVH3

<400> SEQUENCE: 17

Lys Trp Ile Arg Lys Phe Pro Gly Asn Lys Leu Glu Tyr Met Gly
1               5                   10                  15

<210> SEQ ID NO 18
<211> LENGTH: 36
<212> TYPE: PRT
<213> ORGANISM: Artificial Sequence
<220> FEATURE:
<223> OTHER INFORMATION: Synthetic: HC-FR3 of cmVH1, cmVH2, and cmVH3

<400> SEQUENCE: 18

Asn Pro Ser Leu Lys Ser Arg Ile Ser Ile Thr Arg Asp Thr Ser Lys
1               5                   10                  15

Asn Gln Tyr Tyr Leu Gln Leu Asn Ser Val Thr Thr Glu Asp Thr Ala
            20                  25                  30

Thr Tyr Tyr Cys
        35

<210> SEQ ID NO 19
<211> LENGTH: 11
<212> TYPE: PRT
<213> ORGANISM: Artificial Sequence
<220> FEATURE:
<223> OTHER INFORMATION: Synthetic: HC-FR4 of cmVH1, cmVH2, and cmVH3

<400> SEQUENCE: 19

Trp Gly Gln Gly Thr Ser Val Thr Val Ser Ser
1               5                   10
```

```
<210> SEQ ID NO 20
<211> LENGTH: 15
<212> TYPE: PRT
<213> ORGANISM: Artificial Sequence
<220> FEATURE:
<223> OTHER INFORMATION: Synthetic: CDR-L1 of cmVL1, cmVL2, and cmVL3

<400> SEQUENCE: 20

Arg Ala Ser Glu Ser Val Asp Thr Tyr Gly Arg Ser Phe Met His
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Synthetic: CDR-L2of cmVL1, cmVL2, and cmVL3

<400> SEQUENCE: 21

Arg Ala Ser Asn Leu Glu Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic: CDR-L3of cmVL1

<400> SEQUENCE: 22

Gln Gln Ser Tyr Glu Asp Pro Trp Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic: CDR-L3 of cmVL2

<400> SEQUENCE: 23

Tyr Gln Ser Tyr Glu Asp Pro Trp Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic: CDR-L3 of cmVL3

<400> SEQUENCE: 24

His Gln Ser Tyr Glu Asp Pro Trp Thr
1               5

<210> SEQ ID NO 25
<211> LENGTH: 23
<212> TYPE: PRT
<213> ORGANISM: Artificial Sequence
<220> FEATURE:
<223> OTHER INFORMATION: Synthetic: LC-FR1 of cmVL1, cmVL2, and cmVL3

<400> SEQUENCE: 25

Asp Ile Val Leu Thr Gln Ser Pro Ala Ser Leu Ala Val Ser Leu Gly
1               5                   10                  15

Gln Arg Ala Thr Ile Ser Cys
```

```
            20

<210> SEQ ID NO 26
<211> LENGTH: 15
<212> TYPE: PRT
<213> ORGANISM: Artificial Sequence
<220> FEATURE:
<223> OTHER INFORMATION: Synthetic: LC-FR2 of cmVL1, cmVL2, and cmVL3

<400> SEQUENCE: 26

Trp Tyr Gln Gln Lys Ser Gly Gln Ser Pro Lys Leu Leu Ile Tyr
1               5                   10                  15

<210> SEQ ID NO 27
<211> LENGTH: 32
<212> TYPE: PRT
<213> ORGANISM: Artificial Sequence
<220> FEATURE:
<223> OTHER INFORMATION: Synthetic: LC-FR3 of cmVL1, cmVL2, and cmVL3

<400> SEQUENCE: 27

Gly Ile Pro Ala Arg Phe Gly Gly Ser Gly Ser Arg Thr Asp Phe Thr
1               5                   10                  15

Leu Thr Ile Asp Pro Val Glu Ala Asp Asp Val Ala Thr Tyr Tyr Cys
            20                  25                  30

<210> SEQ ID NO 28
<211> LENGTH: 10
<212> TYPE: PRT
<213> ORGANISM: Artificial Sequence
<220> FEATURE:
<223> OTHER INFORMATION: Synthetic: LC-FR4 of cmVL1, cmVL2, and cmVL3

<400> SEQUENCE: 28

Phe Gly Gly Gly Thr Lys Leu Glu Ile Lys
1               5                   10

<210> SEQ ID NO 29
<211> LENGTH: 448
<212> TYPE: PRT
<213> ORGANISM: Artificial Sequence
<220> FEATURE:
<223> OTHER INFORMATION: Synthetic: Exemplary caninized variable heavy
      chain sequence from mouse antibody clone M14 and canine IgG-A

<400> SEQUENCE: 29

Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Ser Val Thr Val Ser Ser Ala Ser Thr Thr Ala Pro Ser Val Phe Pro
        115                 120                 125
```

-continued

```
Leu Ala Pro Ser Cys Gly Ser Thr Ser Gly Ser Thr Val Ala Leu Ala
    130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu His Ser Leu Ser Ser Met Val Thr Val Pro Ser Ser
            180                 185                 190

Arg Trp Pro Ser Glu Thr Phe Thr Cys Asn Val Val His Pro Ala Ser
            195                 200                 205

Asn Thr Lys Val Asp Lys Pro Val Phe Asn Glu Cys Arg Cys Thr Asp
    210                 215                 220

Thr Pro Cys Pro Val Pro Glu Pro Leu Gly Gly Pro Ser Val Leu Ile
225                 230                 235                 240

Phe Pro Pro Lys Pro Lys Asp Ile Leu Arg Ile Thr Arg Thr Pro Glu
                245                 250                 255

Val Thr Cys Val Val Leu Asp Leu Gly Arg Glu Asp Pro Glu Val Gln
            260                 265                 270

Ile Ser Trp Phe Val Asp Gly Lys Glu Val His Thr Ala Lys Thr Gln
            275                 280                 285

Ser Arg Glu Gln Gln Phe Asn Gly Thr Tyr Arg Val Val Ser Val Leu
    290                 295                 300

Pro Ile Glu His Gln Asp Trp Leu Thr Gly Lys Glu Phe Lys Cys Arg
305                 310                 315                 320

Val Asn His Ile Asp Leu Pro Ser Pro Ile Glu Arg Thr Ile Ser Lys
            325                 330                 335

Ala Arg Gly Arg Ala His Lys Pro Ser Val Tyr Val Leu Pro Pro Ser
            340                 345                 350

Pro Lys Glu Leu Ser Ser Ser Asp Thr Val Ser Ile Thr Cys Leu Ile
    355                 360                 365

Lys Asp Phe Tyr Pro Pro Asp Ile Asp Val Glu Trp Gln Ser Asn Gly
    370                 375                 380

Gln Gln Glu Pro Glu Arg Lys His Arg Met Thr Pro Pro Gln Leu Asp
385                 390                 395                 400

Glu Asp Gly Ser Tyr Phe Leu Tyr Ser Lys Leu Ser Val Asp Lys Ser
            405                 410                 415

Arg Trp Gln Gln Gly Asp Pro Phe Thr Cys Ala Val Met His Glu Thr
            420                 425                 430

Leu Gln Asn His Tyr Thr Asp Leu Ser Leu Ser His Ser Pro Gly Lys
            435                 440                 445
```

```
<210> SEQ ID NO 30
<211> LENGTH: 453
<212> TYPE: PRT
<213> ORGANISM: Artificial Sequence
<220> FEATURE:
<223> OTHER INFORMATION: Synthetic: Exemplary caninized variable heavy
      chain sequence from mouse antibody clone M14 and canine IgG-B

<400> SEQUENCE: 30
```

```
Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
                20                  25                  30

Tyr Trp Asn Trp Ile Arg Lys Phe Pro Gly Asn Lys Leu Glu Tyr Met
            35                  40                  45
```

-continued

```
Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Ser Val Thr Val Ser Ser Ala Ser Thr Thr Ala Pro Ser Val Phe Pro
            115                 120                 125

Leu Ala Pro Ser Cys Gly Ser Thr Ser Gly Ser Thr Val Ala Leu Ala
    130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
            165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Ser
            195                 200                 205

Lys Thr Lys Val Asp Lys Pro Val Pro Lys Arg Glu Asn Gly Arg Val
    210                 215                 220

Pro Arg Pro Pro Asp Cys Pro Lys Cys Pro Ala Pro Glu Met Leu Gly
225                 230                 235                 240

Gly Pro Ser Val Phe Ile Phe Pro Pro Lys Pro Lys Asp Thr Leu Leu
            245                 250                 255

Ile Ala Arg Thr Pro Glu Val Thr Cys Val Val Val Asp Leu Asp Pro
            260                 265                 270

Glu Asp Pro Glu Val Gln Ile Ser Trp Phe Val Asp Gly Lys Gln Met
            275                 280                 285

Gln Thr Ala Lys Thr Gln Pro Arg Glu Glu Gln Phe Asn Gly Thr Tyr
    290                 295                 300

Arg Val Val Ser Val Leu Pro Ile Gly His Gln Asp Trp Leu Lys Gly
305                 310                 315                 320

Lys Gln Phe Thr Cys Lys Val Asn Asn Lys Ala Leu Pro Ser Pro Ile
            325                 330                 335

Glu Arg Thr Ile Ser Lys Ala Arg Gly Gln Ala His Gln Pro Ser Val
            340                 345                 350

Tyr Val Leu Pro Pro Ser Arg Glu Glu Leu Ser Lys Asn Thr Val Ser
            355                 360                 365

Leu Thr Cys Leu Ile Lys Asp Phe Phe Pro Pro Asp Ile Asp Val Glu
    370                 375                 380

Trp Gln Ser Asn Gly Gln Gln Glu Pro Glu Ser Lys Tyr Arg Thr Thr
385                 390                 395                 400

Pro Pro Gln Leu Asp Glu Asp Gly Ser Tyr Phe Leu Tyr Ser Lys Leu
            405                 410                 415

Ser Val Asp Lys Ser Arg Trp Gln Arg Gly Asp Thr Phe Ile Cys Ala
            420                 425                 430

Val Met His Glu Ala Leu His Asn His Tyr Thr Gln Glu Ser Leu Ser
            435                 440                 445

His Ser Pro Gly Lys
    450
```

```
<210> SEQ ID NO 31
<211> LENGTH: 451
<212> TYPE: PRT
<213> ORGANISM: Artificial Sequence
<220> FEATURE:
<223> OTHER INFORMATION: Synthetic: Exemplary caninized variable heavy
      chain sequence from mouse antibody clone M14 and canine IgG-C

<400> SEQUENCE: 31

Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
            35                  40                  45

Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Ser Val Thr Val Ser Ser Ala Ser Thr Thr Ala Pro Ser Val Phe Pro
            115                 120                 125

Leu Ala Pro Ser Cys Gly Ser Gln Ser Gly Ser Thr Val Ala Leu Ala
    130                 135                 140

Cys Leu Val Ser Gly Tyr Ile Pro Glu Pro Val Thr Val Ser Trp Asn
145                 150                 155                 160

Ser Val Ser Leu Thr Ser Gly Val His Thr Phe Pro Ser Val Leu Gln
                165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Thr
            195                 200                 205

Asn Thr Lys Val Asp Lys Pro Val Ala Lys Glu Cys Glu Cys Lys Cys
    210                 215                 220

Asn Cys Asn Asn Cys Pro Cys Pro Gly Cys Gly Leu Leu Gly Gly Pro
225                 230                 235                 240

Ser Val Phe Ile Phe Pro Pro Lys Pro Lys Asp Ile Leu Val Thr Ala
                245                 250                 255

Arg Thr Pro Thr Val Thr Cys Val Val Val Asp Leu Asp Pro Glu Asn
            260                 265                 270

Pro Glu Val Gln Ile Ser Trp Phe Val Asp Ser Lys Gln Val Gln Thr
            275                 280                 285

Ala Asn Thr Gln Pro Arg Glu Glu Gln Ser Asn Gly Thr Tyr Arg Val
    290                 295                 300

Val Ser Val Leu Pro Ile Gly His Gln Asp Trp Leu Ser Gly Lys Gln
305                 310                 315                 320

Phe Lys Cys Lys Val Asn Asn Lys Ala Leu Pro Ser Pro Ile Glu Glu
                325                 330                 335

Ile Ile Ser Lys Thr Pro Gly Gln Ala His Gln Pro Asn Val Tyr Val
            340                 345                 350

Leu Pro Pro Ser Arg Asp Glu Met Ser Lys Asn Thr Val Thr Leu Thr
            355                 360                 365
```

```
Cys Leu Val Lys Asp Phe Phe Pro Pro Glu Ile Asp Val Glu Trp Gln
    370             375             380

Ser Asn Gly Gln Gln Glu Pro Glu Ser Lys Tyr Arg Met Thr Pro Pro
385             390             395             400

Gln Leu Asp Glu Asp Gly Ser Tyr Phe Leu Tyr Ser Lys Leu Ser Val
            405             410             415

Asp Lys Ser Arg Trp Gln Arg Gly Asp Thr Phe Ile Cys Ala Val Met
            420             425             430

His Glu Ala Leu His Asn His Tyr Thr Gln Ile Ser Leu Ser His Ser
        435             440             445

Pro Gly Lys
    450

<210> SEQ ID NO 32
<211> LENGTH: 449
<212> TYPE: PRT
<213> ORGANISM: Artificial Sequence
<220> FEATURE:
<223> OTHER INFORMATION: Synthetic: Exemplary caninized variable heavy
     chain sequence from mouse antibody clone M14 and canine IgG-D

<400> SEQUENCE: 32

Glu Val Gln Leu Val Glu Ser Gly Pro Ser Leu Val Lys Pro Gly Gly
1               5               10              15

Ser Leu Arg Leu Thr Cys Ser Val Thr Gly Asp Ser Ile Thr Ser Gly
            20              25              30

Tyr Trp Asn Trp Ile Arg Lys Phe Pro Gly Asn Lys Leu Glu Tyr Met
        35              40              45

Gly Tyr Ile Ser Tyr Ser Gly Ile Thr Asp Tyr Asn Pro Ser Leu Lys
    50              55              60

Ser Arg Ile Thr Ile Ser Arg Asp Thr Ser Lys Asn Gln Tyr Tyr Leu
65              70              75              80

Gln Leu Asn Ser Val Thr Thr Glu Asp Thr Ala Thr Tyr Tyr Cys Ala
            85              90              95

Arg Tyr Gly Asn Tyr Gly Tyr Ala Met Asp Tyr Trp Gly Gln Gly Thr
            100             105             110

Ser Val Thr Val Ser Ser Ala Ser Thr Thr Ala Pro Ser Val Phe Pro
        115             120             125

Leu Ala Pro Ser Cys Gly Ser Thr Ser Gly Ser Thr Val Ala Leu Ala
    130             135             140

Cys Leu Val Ser Gly Tyr Phe Pro Glu Pro Val Thr Val Ser Trp Asn
145             150             155             160

Ser Gly Ser Leu Thr Ser Gly Val His Thr Phe Pro Ser Val Leu Gln
            165             170             175

Ser Ser Gly Leu Tyr Ser Leu Ser Ser Thr Val Thr Val Pro Ser Ser
            180             185             190

Arg Trp Pro Ser Glu Thr Phe Thr Cys Asn Val Val His Pro Ala Ser
        195             200             205

Asn Thr Lys Val Asp Lys Pro Val Pro Lys Glu Ser Thr Cys Lys Cys
    210             215             220

Ile Ser Pro Cys Pro Val Pro Glu Ser Leu Gly Gly Pro Ser Val Phe
225             230             235             240

Ile Phe Pro Pro Lys Pro Lys Asp Ile Leu Arg Ile Thr Arg Thr Pro
            245             250             255

Glu Ile Thr Cys Val Val Leu Asp Leu Gly Arg Glu Asp Pro Glu Val
```

-continued

```
                260              265              270
Gln Ile Ser Trp Phe Val Asp Gly Lys Glu Val His Thr Ala Lys Thr
        275              280              285
Gln Pro Arg Glu Gln Gln Phe Asn Ser Thr Tyr Arg Val Val Ser Val
        290              295              300
Leu Pro Ile Glu His Gln Asp Trp Leu Thr Gly Lys Glu Phe Lys Cys
305              310              315              320
Arg Val Asn His Ile Gly Leu Pro Ser Pro Ile Glu Arg Thr Ile Ser
                325              330              335
Lys Ala Arg Gly Gln Ala His Gln Pro Ser Val Tyr Val Leu Pro Pro
                340              345              350
Ser Pro Lys Glu Leu Ser Ser Ser Asp Thr Val Thr Leu Thr Cys Leu
                355              360              365
Ile Lys Asp Phe Phe Pro Pro Glu Ile Asp Val Glu Trp Gln Ser Asn
        370              375              380
Gly Gln Pro Glu Pro Glu Ser Lys Tyr His Thr Thr Ala Pro Gln Leu
385              390              395              400
Asp Glu Asp Gly Ser Tyr Phe Leu Tyr Ser Lys Leu Ser Val Asp Lys
                405              410              415
Ser Arg Trp Gln Gln Gly Asp Thr Phe Thr Cys Ala Val Met His Glu
                420              425              430
Ala Leu Gln Asn His Tyr Thr Asp Leu Ser Leu Ser His Ser Pro Gly
        435              440              445
Lys
```

<210> SEQ ID NO 33
<211> LENGTH: 221
<212> TYPE: PRT
<213> ORGANISM: Artificial Sequence
<220> FEATURE:
<223> OTHER INFORMATION: Synthetic: Exemplary caninized variable light
     chain sequence from mouse antibody clone M14 and canine light
     chain constant region

<400> SEQUENCE: 33

```
Asp Ile Val Met Thr Gln Ser Pro Ala Ser Leu Ser Val Ser Leu Gly
1               5                10               15
Gln Arg Ala Thr Ile Ser Cys Arg Ala Ser Glu Ser Val Asp Thr Tyr
            20               25               30
Gly Asn Ser Phe Met His Trp Tyr Gln Gln Lys Pro Gly Gln Ser Pro
        35               40               45
Lys Leu Leu Ile Tyr Arg Ala Ser Asn Leu Glu Ser Gly Ile Pro Ala
    50               55               60
Arg Phe Gly Gly Ser Gly Ser Gly Thr Asp Phe Thr Leu Thr Ile Asp
65               70               75               80
Pro Val Gln Ala Asp Asp Val Ala Thr Tyr Tyr Cys Gln Gln Ser Tyr
                85               90               95
Glu Asp Pro Trp Thr Phe Gly Gly Gly Thr Lys Leu Glu Ile Lys Arg
            100              105              110
Asn Asp Ala Gln Pro Ala Val Tyr Leu Phe Gln Pro Ser Pro Asp Gln
        115              120              125
Leu His Thr Gly Ser Ala Ser Val Val Cys Leu Leu Asn Ser Phe Tyr
    130              135              140
Pro Lys Asp Ile Asn Val Lys Trp Lys Val Asp Gly Val Ile Gln Asp
145              150              155              160
```

-continued

Thr Gly Ile Gln Glu Ser Val Thr Glu Gln Asp Lys Asp Ser Thr Tyr
                165                     170                     175

Ser Leu Ser Ser Thr Leu Thr Met Ser Ser Thr Glu Tyr Leu Ser His
                180                     185                     190

Glu Leu Tyr Ser Cys Glu Ile Thr His Lys Ser Leu Pro Ser Thr Leu
            195                     200                     205

Ile Lys Ser Phe Gln Arg Ser Glu Cys Gln Arg Val Asp
        210                     215                     220

<210> SEQ ID NO 34
<211> LENGTH: 448
<212> TYPE: PRT
<213> ORGANISM: Artificial Sequence
<220> FEATURE:
<223> OTHER INFORMATION: Synthetic: Exemplary caninized, matured
      variable heavy chain sequence cmVH1 and canine IgG-A

<400> SEQUENCE: 34

Glu Val Gln Leu Val Glu Ser Gly Pro Ser Leu Val Lys Pro Gly Gly
1                   5                   10                  15

Ser Leu Arg Leu Thr Cys Ser Val Thr Gly Asp Ser Ile Thr Ser Gly
                20                  25                  30

Tyr Trp Lys Trp Ile Arg Lys Phe Pro Gly Asn Lys Leu Glu Tyr Met
            35                  40                  45

Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Ser Val Thr Val Ser Ser Ala Ser Thr Thr Ala Pro Ser Val Phe Pro
            115                 120                 125

Leu Ala Pro Ser Cys Gly Ser Thr Ser Gly Ser Thr Val Ala Leu Ala
        130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu His Ser Leu Ser Ser Met Val Thr Val Pro Ser Ser
            180                 185                 190

Arg Trp Pro Ser Glu Thr Phe Thr Cys Asn Val Val His Pro Ala Ser
        195                 200                 205

Asn Thr Lys Val Asp Lys Pro Val Phe Asn Glu Cys Arg Cys Thr Asp
        210                 215                 220

Thr Pro Cys Pro Val Pro Glu Pro Leu Gly Gly Pro Ser Val Leu Ile
225                 230                 235                 240

Phe Pro Pro Lys Pro Lys Asp Ile Leu Arg Ile Thr Arg Thr Pro Glu
            245                 250                 255

Val Thr Cys Val Val Leu Asp Leu Gly Arg Glu Asp Pro Glu Val Gln
            260                 265                 270

Ile Ser Trp Phe Val Asp Gly Lys Glu Val His Thr Ala Lys Thr Gln
            275                 280                 285

Ser Arg Glu Gln Gln Phe Asn Gly Thr Tyr Arg Val Val Ser Val Leu
        290                 295                 300

-continued

```
Pro Ile Glu His Gln Asp Trp Leu Thr Gly Lys Glu Phe Lys Cys Arg
305             310             315             320

Val Asn His Ile Asp Leu Pro Ser Pro Ile Glu Arg Thr Ile Ser Lys
            325             330             335

Ala Arg Gly Arg Ala His Lys Pro Ser Val Tyr Val Leu Pro Pro Ser
        340             345             350

Pro Lys Glu Leu Ser Ser Ser Asp Thr Val Ser Ile Thr Cys Leu Ile
        355             360             365

Lys Asp Phe Tyr Pro Pro Asp Ile Asp Val Glu Trp Gln Ser Asn Gly
        370             375             380

Gln Gln Glu Pro Glu Arg Lys His Arg Met Thr Pro Pro Gln Leu Asp
385             390             395             400

Glu Asp Gly Ser Tyr Phe Leu Tyr Ser Lys Leu Ser Val Asp Lys Ser
            405             410             415

Arg Trp Gln Gln Gly Asp Pro Phe Thr Cys Ala Val Met His Glu Thr
            420             425             430

Leu Gln Asn His Tyr Thr Asp Leu Ser Leu Ser His Ser Pro Gly Lys
            435             440             445
```

```
<210> SEQ ID NO 35
<211> LENGTH: 453
<212> TYPE: PRT
<213> ORGANISM: Artificial Sequence
<220> FEATURE:
<223> OTHER INFORMATION: Synthetic: Exemplary caninized, matured
      variable heavy chain sequence cmVH1 and canine IgG-B

<400> SEQUENCE: 35
```

```
Glu Val Gln Leu Val Glu Ser Gly Pro Ser Leu Val Lys Pro Gly Gly
1               5               10              15

Ser Leu Arg Leu Thr Cys Ser Val Thr Gly Asp Ser Ile Thr Ser Gly
            20              25              30

Tyr Trp Lys Trp Ile Arg Lys Phe Pro Gly Asn Lys Leu Glu Tyr Met
        35              40              45

Gly Tyr Ile Ser Tyr Ser Gly Ile Thr Asp Tyr Asn Pro Ser Leu Lys
    50              55              60

Ser Arg Ile Thr Ile Ser Arg Asp Thr Ser Lys Asn Gln Tyr Tyr Leu
65              70              75              80

Gln Leu Asn Ser Val Thr Thr Glu Asp Thr Ala Thr Tyr Tyr Cys Ala
            85              90              95

Arg Tyr Gly Asn Tyr Gly Tyr Ala Met Asp Tyr Trp Gly Gln Gly Thr
            100             105             110

Ser Val Thr Val Ser Ser Ala Ser Thr Thr Ala Pro Ser Val Phe Pro
        115             120             125

Leu Ala Pro Ser Cys Gly Ser Thr Ser Gly Ser Thr Val Ala Leu Ala
        130             135             140

Cys Leu Val Ser Gly Tyr Phe Pro Glu Pro Val Thr Val Ser Trp Asn
145             150             155             160

Ser Gly Ser Leu Thr Ser Gly Val His Thr Phe Pro Ser Val Leu Gln
            165             170             175

Ser Ser Gly Leu Tyr Ser Leu Ser Ser Met Val Thr Val Pro Ser Ser
            180             185             190

Arg Trp Pro Ser Glu Thr Phe Thr Cys Asn Val Ala His Pro Ala Ser
        195             200             205

Lys Thr Lys Val Asp Lys Pro Val Pro Lys Arg Glu Asn Gly Arg Val
```

```
            210             215             220

Pro Arg Pro Pro Asp Cys Pro Lys Cys Pro Ala Pro Glu Met Leu Gly
225             230             235             240

Gly Pro Ser Val Phe Ile Phe Pro Pro Lys Pro Lys Asp Thr Leu Leu
                245             250             255

Ile Ala Arg Thr Pro Glu Val Thr Cys Val Val Val Asp Leu Asp Pro
                260             265             270

Glu Asp Pro Glu Val Gln Ile Ser Trp Phe Val Asp Gly Lys Gln Met
            275             280             285

Gln Thr Ala Lys Thr Gln Pro Arg Glu Glu Gln Phe Asn Gly Thr Tyr
            290             295             300

Arg Val Val Ser Val Leu Pro Ile Gly His Gln Asp Trp Leu Lys Gly
305             310             315             320

Lys Gln Phe Thr Cys Lys Val Asn Asn Lys Ala Leu Pro Ser Pro Ile
                325             330             335

Glu Arg Thr Ile Ser Lys Ala Arg Gly Gln Ala His Gln Pro Ser Val
                340             345             350

Tyr Val Leu Pro Pro Ser Arg Glu Glu Leu Ser Lys Asn Thr Val Ser
            355             360             365

Leu Thr Cys Leu Ile Lys Asp Phe Phe Pro Pro Asp Ile Asp Val Glu
            370             375             380

Trp Gln Ser Asn Gly Gln Gln Glu Pro Glu Ser Lys Tyr Arg Thr Thr
385             390             395             400

Pro Pro Gln Leu Asp Glu Asp Gly Ser Tyr Phe Leu Tyr Ser Lys Leu
                405             410             415

Ser Val Asp Lys Ser Arg Trp Gln Arg Gly Asp Thr Phe Ile Cys Ala
                420             425             430

Val Met His Glu Ala Leu His Asn His Tyr Thr Gln Glu Ser Leu Ser
            435             440             445

His Ser Pro Gly Lys
    450
```

<210> SEQ ID NO 36
<211> LENGTH: 451
<212> TYPE: PRT
<213> ORGANISM: Artificial Sequence
<220> FEATURE:
<223> OTHER INFORMATION: Synthetic: Exemplary caninized, matured
    variable heavy chain sequence cmVH1 and canine IgG-C

<400> SEQUENCE: 36

```
Glu Val Gln Leu Val Glu Ser Gly Pro Ser Leu Val Lys Pro Gly Gly
1               5               10              15

Ser Leu Arg Leu Thr Cys Ser Val Thr Gly Asp Ser Ile Thr Ser Gly
            20              25              30

Tyr Trp Lys Trp Ile Arg Lys Phe Pro Gly Asn Lys Leu Glu Tyr Met
            35              40              45

Gly Tyr Ile Ser Tyr Ser Gly Ile Thr Asp Tyr Asn Pro Ser Leu Lys
        50              55              60

Ser Arg Ile Thr Ile Ser Arg Asp Thr Ser Lys Asn Gln Tyr Tyr Leu
65              70              75              80

Gln Leu Asn Ser Val Thr Thr Glu Asp Thr Ala Thr Tyr Tyr Cys Ala
                85              90              95

Arg Tyr Gly Asn Tyr Gly Tyr Ala Met Asp Tyr Trp Gly Gln Gly Thr
            100             105             110
```

-continued

```
Ser Val Thr Val Ser Ser Ala Ser Thr Thr Ala Pro Ser Val Phe Pro
        115                 120                 125

Leu Ala Pro Ser Cys Gly Ser Gln Ser Gly Ser Thr Val Ala Leu Ala
        130                 135                 140

Cys Leu Val Ser Gly Tyr Ile Pro Glu Pro Val Thr Val Ser Trp Asn
145                 150                 155                 160

Ser Val Ser Leu Thr Ser Gly Val His Thr Phe Pro Ser Val Leu Gln
                165                 170                 175

Ser Ser Gly Leu Tyr Ser Leu Ser Ser Met Val Thr Val Pro Ser Ser
                180                 185                 190

Arg Trp Pro Ser Glu Thr Phe Thr Cys Asn Val Ala His Pro Ala Thr
        195                 200                 205

Asn Thr Lys Val Asp Lys Pro Val Ala Lys Glu Cys Glu Cys Lys Cys
        210                 215                 220

Asn Cys Asn Asn Cys Pro Cys Pro Gly Cys Gly Leu Leu Gly Gly Pro
225                 230                 235                 240

Ser Val Phe Ile Phe Pro Pro Lys Pro Lys Asp Ile Leu Val Thr Ala
                245                 250                 255

Arg Thr Pro Thr Val Thr Cys Val Val Val Asp Leu Asp Pro Glu Asn
        260                 265                 270

Pro Glu Val Gln Ile Ser Trp Phe Val Asp Ser Lys Gln Val Gln Thr
        275                 280                 285

Ala Asn Thr Gln Pro Arg Glu Glu Gln Ser Asn Gly Thr Tyr Arg Val
        290                 295                 300

Val Ser Val Leu Pro Ile Gly His Gln Asp Trp Leu Ser Gly Lys Gln
305                 310                 315                 320

Phe Lys Cys Lys Val Asn Asn Lys Ala Leu Pro Ser Pro Ile Glu Glu
                325                 330                 335

Ile Ile Ser Lys Thr Pro Gly Gln Ala His Gln Pro Asn Val Tyr Val
                340                 345                 350

Leu Pro Pro Ser Arg Asp Glu Met Ser Lys Asn Thr Val Thr Leu Thr
        355                 360                 365

Cys Leu Val Lys Asp Phe Phe Pro Pro Glu Ile Asp Val Glu Trp Gln
        370                 375                 380

Ser Asn Gly Gln Gln Glu Pro Glu Ser Lys Tyr Arg Met Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
                420                 425                 430

His Glu Ala Leu His Asn His Tyr Thr Gln Ile Ser Leu Ser His Ser
        435                 440                 445

Pro Gly Lys
    450
```

<210> SEQ ID NO 37
<211> LENGTH: 449
<212> TYPE: PRT
<213> ORGANISM: Artificial Sequence
<220> FEATURE:
<223> OTHER INFORMATION: Synthetic: Exemplary caninized, matured
      variable heavy chain sequence cmVH1 and canine IgG-D

<400> SEQUENCE: 37

```
Glu Val Gln Leu Val Glu Ser Gly Pro Ser Leu Val Lys Pro Gly Gly
1               5                   10                  15
```

```
Ser Leu Arg Leu Thr Cys Ser Val Thr Gly Asp Ser Ile Thr Ser Gly
            20                  25                  30

Tyr Trp Lys Trp Ile Arg Lys Phe Pro Gly Asn Lys Leu Glu Tyr Met
            35                  40                  45

Gly Tyr Ile Ser Tyr Ser Gly Ile Thr Asp Tyr Asn Pro Ser Leu Lys
            50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
            85                  90                  95

Arg Tyr Gly Asn Tyr Gly Tyr Ala Met Asp Tyr Trp Gly Gln Gly Thr
            100                 105                 110

Ser Val Thr Val Ser Ser Ala Ser Thr Thr Ala Pro Ser Val Phe Pro
            115                 120                 125

Leu Ala Pro Ser Cys Gly Ser Thr Ser Gly Ser Thr Val Ala Leu Ala
            130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
            165                 170                 175

Ser Ser Gly Leu Tyr Ser Leu Ser Ser Thr Val Thr Val Pro Ser Ser
            180                 185                 190

Arg Trp Pro Ser Glu Thr Phe Thr Cys Asn Val Val His Pro Ala Ser
            195                 200                 205

Asn Thr Lys Val Asp Lys Pro Val Pro Lys Glu Ser Thr Cys Lys Cys
            210                 215                 220

Ile Ser Pro Cys Pro Val Pro Glu Ser Leu Gly Gly Pro Ser Val Phe
225                 230                 235                 240

Ile Phe Pro Pro Lys Pro Lys Asp Ile Leu Arg Ile Thr Arg Thr Pro
            245                 250                 255

Glu Ile Thr Cys Val Val Leu Asp Leu Gly Arg Glu Asp Pro Glu Val
            260                 265                 270

Gln Ile Ser Trp Phe Val Asp Gly Lys Glu Val His Thr Ala Lys Thr
            275                 280                 285

Gln Pro Arg Glu Gln Gln Phe Asn Ser Thr Tyr Arg Val Val Ser Val
            290                 295                 300

Leu Pro Ile Glu His Gln Asp Trp Leu Thr Gly Lys Glu Phe Lys Cys
305                 310                 315                 320

Arg Val Asn His Ile Gly Leu Pro Ser Pro Ile Glu Arg Thr Ile Ser
            325                 330                 335

Lys Ala Arg Gly Gln Ala His Gln Pro Ser Val Tyr Val Leu Pro Pro
            340                 345                 350

Ser Pro Lys Glu Leu Ser Ser Ser Asp Thr Val Thr Leu Thr Cys Leu
            355                 360                 365

Ile Lys Asp Phe Phe Pro Pro Glu Ile Asp Val Glu Trp Gln Ser Asn
            370                 375                 380

Gly Gln Pro Glu Pro Glu Ser Lys Tyr His Thr Thr Ala Pro Gln Leu
385                 390                 395                 400

Asp Glu Asp Gly Ser Tyr Phe Leu Tyr Ser Lys Leu Ser Val Asp Lys
            405                 410                 415

Ser Arg Trp Gln Gln Gly Asp Thr Phe Thr Cys Ala Val Met His Glu
            420                 425                 430
```

-continued

```
Ala Leu Gln Asn His Tyr Thr Asp Leu Ser Leu Ser His Ser Pro Gly
        435                 440                 445

Lys

<210> SEQ ID NO 38
<211> LENGTH: 448
<212> TYPE: PRT
<213> ORGANISM: Artificial Sequence
<220> FEATURE:
<223> OTHER INFORMATION: Synthetic: Exemplary caninized, matured
      variable heavy chain sequence cmVH2 and canine IgG-A

<400> SEQUENCE: 38

Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
        20                  25                  30

Tyr Trp Lys Trp Ile Arg Lys Phe Pro Gly Asn Lys Leu Glu Tyr Met
        35                  40                  45

Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Pro Asn Tyr Gly Tyr Ala Met Asp Tyr Trp Gly Gln Gly Thr
            100                 105                 110

Ser Val Thr Val Ser Ser Ala Ser Thr Thr Ala Pro Ser Val Phe Pro
        115                 120                 125

Leu Ala Pro Ser Cys Gly Ser Thr Ser Gly Ser Thr Val Ala Leu Ala
    130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu His Ser Leu Ser Ser Met Val Thr Val Pro Ser Ser
            180                 185                 190

Arg Trp Pro Ser Glu Thr Phe Thr Cys Asn Val Val His Pro Ala Ser
            195                 200                 205

Asn Thr Lys Val Asp Lys Pro Val Phe Asn Glu Cys Arg Cys Thr Asp
    210                 215                 220

Thr Pro Cys Pro Val Pro Glu Pro Leu Gly Gly Pro Ser Val Leu Ile
225                 230                 235                 240

Phe Pro Pro Lys Pro Lys Asp Ile Leu Arg Ile Thr Arg Thr Pro Glu
            245                 250                 255

Val Thr Cys Val Val Leu Asp Leu Gly Arg Glu Asp Pro Glu Val Gln
            260                 265                 270

Ile Ser Trp Phe Val Asp Gly Lys Glu Val His Thr Ala Lys Thr Gln
        275                 280                 285

Ser Arg Glu Gln Gln Phe Asn Gly Thr Tyr Arg Val Val Ser Val Leu
    290                 295                 300

Pro Ile Glu His Gln Asp Trp Leu Thr Gly Lys Glu Phe Lys Cys Arg
305                 310                 315                 320

Val Asn His Ile Asp Leu Pro Ser Pro Ile Glu Arg Thr Ile Ser Lys
                325                 330                 335
```

-continued

Ala Arg Gly Arg Ala His Lys Pro Ser Val Tyr Val Leu Pro Pro Ser
            340             345             350

Pro Lys Glu Leu Ser Ser Ser Asp Thr Val Ser Ile Thr Cys Leu Ile
        355             360             365

Lys Asp Phe Tyr Pro Pro Asp Ile Asp Val Glu Trp Gln Ser Asn Gly
        370             375             380

Gln Gln Glu Pro Glu Arg Lys His Arg Met Thr Pro Pro Gln Leu Asp
385             390             395             400

Glu Asp Gly Ser Tyr Phe Leu Tyr Ser Lys Leu Ser Val Asp Lys Ser
            405             410             415

Arg Trp Gln Gln Gly Asp Pro Phe Thr Cys Ala Val Met His Glu Thr
        420             425             430

Leu Gln Asn His Tyr Thr Asp Leu Ser Leu Ser His Ser Pro Gly Lys
        435             440             445

<210> SEQ ID NO 39
<211> LENGTH: 453
<212> TYPE: PRT
<213> ORGANISM: Artificial Sequence
<220> FEATURE:
<223> OTHER INFORMATION: Synthetic: Exemplary caninized, matured
      variable heavy chain sequence cmVH2 and canine IgG-B

<400> SEQUENCE: 39

Glu Val Gln Leu Val Glu Ser Gly Pro Ser Leu Val Lys Pro Gly Gly
1               5               10              15

Ser Leu Arg Leu Thr Cys Ser Val Thr Gly Asp Ser Ile Thr Ser Gly
        20              25              30

Tyr Trp Lys Trp Ile Arg Lys Phe Pro Gly Asn Lys Leu Glu Tyr Met
        35              40              45

Gly Tyr Ile Ser Tyr Ser Gly Ile Thr Asp Tyr Asn Pro Ser Leu Lys
        50              55              60

Ser Arg Ile Thr Ile Ser Arg Asp Thr Ser Lys Asn Gln Tyr Tyr Leu
65              70              75              80

Gln Leu Asn Ser Val Thr Thr Glu Asp Thr Ala Thr Tyr Tyr Cys Ala
            85              90              95

Arg Tyr Pro Asn Tyr Gly Tyr Ala Met Asp Tyr Trp Gly Gln Gly Thr
        100             105             110

Ser Val Thr Val Ser Ser Ala Ser Thr Thr Ala Pro Ser Val Phe Pro
        115             120             125

Leu Ala Pro Ser Cys Gly Ser Thr Ser Gly Ser Thr Val Ala Leu Ala
        130             135             140

Cys Leu Val Ser Gly Tyr Phe Pro Glu Pro Val Thr Val Ser Trp Asn
145             150             155             160

Ser Gly Ser Leu Thr Ser Gly Val His Thr Phe Pro Ser Val Leu Gln
            165             170             175

Ser Ser Gly Leu Tyr Ser Leu Ser Ser Met Val Thr Val Pro Ser Ser
            180             185             190

Arg Trp Pro Ser Glu Thr Phe Thr Cys Asn Val Ala His Pro Ala Ser
        195             200             205

Lys Thr Lys Val Asp Lys Pro Val Pro Lys Arg Glu Asn Gly Arg Val
        210             215             220

Pro Arg Pro Pro Asp Cys Pro Lys Cys Pro Ala Pro Glu Met Leu Gly
225             230             235             240

Gly Pro Ser Val Phe Ile Phe Pro Pro Lys Pro Lys Asp Thr Leu Leu
            245             250             255

-continued

```
Ile Ala Arg Thr Pro Glu Val Thr Cys Val Val Val Asp Leu Asp Pro
            260                 265                 270

Glu Asp Pro Glu Val Gln Ile Ser Trp Phe Val Asp Gly Lys Gln Met
            275                 280                 285

Gln Thr Ala Lys Thr Gln Pro Arg Glu Glu Gln Phe Asn Gly Thr Tyr
        290                 295                 300

Arg Val Val Ser Val Leu Pro Ile Gly His Gln Asp Trp Leu Lys Gly
305                 310                 315                 320

Lys Gln Phe Thr Cys Lys Val Asn Asn Lys Ala Leu Pro Ser Pro Ile
                325                 330                 335

Glu Arg Thr Ile Ser Lys Ala Arg Gly Gln Ala His Gln Pro Ser Val
            340                 345                 350

Tyr Val Leu Pro Pro Ser Arg Glu Glu Leu Ser Lys Asn Thr Val Ser
            355                 360                 365

Leu Thr Cys Leu Ile Lys Asp Phe Phe Pro Pro Asp Ile Asp Val Glu
        370                 375                 380

Trp Gln Ser Asn Gly Gln Gln Glu Pro Glu Ser Lys Tyr Arg Thr Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Arg Gly Asp Thr Phe Ile Cys Ala
            420                 425                 430

Val Met His Glu Ala Leu His Asn His Tyr Thr Gln Glu Ser Leu Ser
        435                 440                 445

His Ser Pro Gly Lys
        450

<210> SEQ ID NO 40
<211> LENGTH: 451
<212> TYPE: PRT
<213> ORGANISM: Artificial Sequence
<220> FEATURE:
<223> OTHER INFORMATION: Synthetic: Exemplary caninized, matured
      variable heavy chain sequence cmVH2 and canine IgG-C

<400> SEQUENCE: 40

Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Lys Trp Ile Arg Lys Phe Pro Gly Asn Lys Leu Glu Tyr Met
        35                  40                  45

Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Pro Asn Tyr Gly Tyr Ala Met Asp Tyr Trp Gly Gln Gly Thr
            100                 105                 110

Ser Val Thr Val Ser Ser Ala Ser Thr Thr Ala Pro Ser Val Phe Pro
            115                 120                 125

Leu Ala Pro Ser Cys Gly Ser Gln Ser Gly Ser Thr Val Ala Leu Ala
        130                 135                 140

Cys Leu Val Ser Gly Tyr Ile Pro Glu Pro Val Thr Val Ser Trp Asn
```

```
145                 150                 155                 160

Ser Val Ser Leu Thr Ser Gly Val His Thr Phe Pro Ser Val Leu Gln
            165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Thr
            195                 200                 205

Asn Thr Lys Val Asp Lys Pro Val Ala Lys Glu Cys Glu Cys Lys Cys
            210                 215                 220

Asn Cys Asn Asn Cys Pro Cys Pro Gly Cys Gly Leu Leu Gly Gly Pro
225                 230                 235                 240

Ser Val Phe Ile Phe Pro Pro Lys Pro Lys Asp Ile Leu Val Thr Ala
                    245                 250                 255

Arg Thr Pro Thr Val Thr Cys Val Val Val Asp Leu Asp Pro Glu Asn
                    260                 265                 270

Pro Glu Val Gln Ile Ser Trp Phe Val Asp Ser Lys Gln Val Gln Thr
                    275                 280                 285

Ala Asn Thr Gln Pro Arg Glu Glu Gln Ser Asn Gly Thr Tyr Arg Val
            290                 295                 300

Val Ser Val Leu Pro Ile Gly His Gln Asp Trp Leu Ser Gly Lys Gln
305                 310                 315                 320

Phe Lys Cys Lys Val Asn Asn Lys Ala Leu Pro Ser Pro Ile Glu Glu
                    325                 330                 335

Ile Ile Ser Lys Thr Pro Gly Gln Ala His Gln Pro Asn Val Tyr Val
                    340                 345                 350

Leu Pro Pro Ser Arg Asp Glu Met Ser Lys Asn Thr Val Thr Leu Thr
                    355                 360                 365

Cys Leu Val Lys Asp Phe Phe Pro Pro Glu Ile Asp Val Glu Trp Gln
            370                 375                 380

Ser Asn Gly Gln Gln Glu Pro Glu Ser Lys Tyr Arg Met Thr Pro Pro
385                 390                 395                 400

Gln Leu Asp Glu Asp Gly Ser Tyr Phe Leu Tyr Ser Lys Leu Ser Val
                    405                 410                 415

Asp Lys Ser Arg Trp Gln Arg Gly Asp Thr Phe Ile Cys Ala Val Met
                    420                 425                 430

His Glu Ala Leu His Asn His Tyr Thr Gln Ile Ser Leu Ser His Ser
            435                 440                 445

Pro Gly Lys
        450
```

```
<210> SEQ ID NO 41
<211> LENGTH: 449
<212> TYPE: PRT
<213> ORGANISM: Artificial Sequence
<220> FEATURE:
<223> OTHER INFORMATION: Synthetic: Exemplary caninized, matured
      variable heavy chain sequence cmVH2 and canine IgG-D

<400> SEQUENCE: 41

Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Lys Trp Ile Arg Lys Phe Pro Gly Asn Lys Leu Glu Tyr Met
        35                  40                  45
```

```
Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Pro Asn Tyr Gly Tyr Ala Met Asp Tyr Trp Gly Gln Gly Thr
                100                 105                 110

Ser Val Thr Val Ser Ser Ala Ser Thr Thr Ala Pro Ser Val Phe Pro
            115                 120                 125

Leu Ala Pro Ser Cys Gly Ser Thr Ser Gly Ser Thr Val Ala Leu Ala
    130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu Tyr Ser Leu Ser Ser Thr Val Thr Val Pro Ser Ser
            180                 185                 190

Arg Trp Pro Ser Glu Thr Phe Thr Cys Asn Val Val His Pro Ala Ser
        195                 200                 205

Asn Thr Lys Val Asp Lys Pro Val Pro Lys Glu Ser Thr Cys Lys Cys
    210                 215                 220

Ile Ser Pro Cys Pro Val Pro Glu Ser Leu Gly Gly Pro Ser Val Phe
225                 230                 235                 240

Ile Phe Pro Pro Lys Pro Lys Asp Ile Leu Arg Ile Thr Arg Thr Pro
                245                 250                 255

Glu Ile Thr Cys Val Val Leu Asp Leu Gly Arg Glu Asp Pro Glu Val
                260                 265                 270

Gln Ile Ser Trp Phe Val Asp Gly Lys Glu Val His Thr Ala Lys Thr
            275                 280                 285

Gln Pro Arg Glu Gln Gln Phe Asn Ser Thr Tyr Arg Val Val Ser Val
    290                 295                 300

Leu Pro Ile Glu His Gln Asp Trp Leu Thr Gly Lys Glu Phe Lys Cys
305                 310                 315                 320

Arg Val Asn His Ile Gly Leu Pro Ser Pro Ile Glu Arg Thr Ile Ser
                325                 330                 335

Lys Ala Arg Gly Gln Ala His Gln Pro Ser Val Tyr Val Leu Pro Pro
                340                 345                 350

Ser Pro Lys Glu Leu Ser Ser Ser Asp Thr Val Thr Leu Thr Cys Leu
            355                 360                 365

Ile Lys Asp Phe Phe Pro Pro Glu Ile Asp Val Glu Trp Gln Ser Asn
    370                 375                 380

Gly Gln Pro Glu Pro Glu Ser Lys Tyr His Thr Thr Ala Pro Gln Leu
385                 390                 395                 400

Asp Glu Asp Gly Ser Tyr Phe Leu Tyr Ser Lys Leu Ser Val Asp Lys
                405                 410                 415

Ser Arg Trp Gln Gln Gly Asp Thr Phe Thr Cys Ala Val Met His Glu
            420                 425                 430

Ala Leu Gln Asn His Tyr Thr Asp Leu Ser Leu Ser His Ser Pro Gly
            435                 440                 445

Lys
```

```
<210> SEQ ID NO 42
```

-continued

```
<211> LENGTH: 448
<212> TYPE: PRT
<213> ORGANISM: Artificial Sequence
<220> FEATURE:
<223> OTHER INFORMATION: Synthetic: Exemplary caninized, matured
      variable heavy chain sequence cmVH3 and canine IgG-A

<400> SEQUENCE: 42

Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Lys Trp Ile Arg Lys Phe Pro Gly Asn Lys Leu Glu Tyr Met
        35                  40                  45

Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
            85                  90                  95

Arg Tyr Ala Asn Tyr Gly Tyr Ala Met Asp Tyr Trp Gly Gln Gly Thr
            100                 105                 110

Ser Val Thr Val Ser Ser Ala Ser Thr Thr Ala Pro Ser Val Phe Pro
        115                 120                 125

Leu Ala Pro Ser Cys Gly Ser Thr Ser Gly Ser Thr Val Ala Leu Ala
    130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
            165                 170                 175

Ser Ser Gly Leu His Ser Leu Ser Ser Met Val Thr Val Pro Ser Ser
            180                 185                 190

Arg Trp Pro Ser Glu Thr Phe Thr Cys Asn Val Val His Pro Ala Ser
            195                 200                 205

Asn Thr Lys Val Asp Lys Pro Val Phe Asn Glu Cys Arg Cys Thr Asp
    210                 215                 220

Thr Pro Cys Pro Val Pro Glu Pro Leu Gly Gly Pro Ser Val Leu Ile
225                 230                 235                 240

Phe Pro Pro Lys Pro Lys Asp Ile Leu Arg Ile Thr Arg Thr Pro Glu
            245                 250                 255

Val Thr Cys Val Val Leu Asp Leu Gly Arg Glu Asp Pro Glu Val Gln
            260                 265                 270

Ile Ser Trp Phe Val Asp Gly Lys Glu Val His Thr Ala Lys Thr Gln
        275                 280                 285

Ser Arg Glu Gln Gln Phe Asn Gly Thr Tyr Arg Val Val Ser Val Leu
    290                 295                 300

Pro Ile Glu His Gln Asp Trp Leu Thr Gly Lys Glu Phe Lys Cys Arg
305                 310                 315                 320

Val Asn His Ile Asp Leu Pro Ser Pro Ile Glu Arg Thr Ile Ser Lys
            325                 330                 335

Ala Arg Gly Arg Ala His Lys Pro Ser Val Tyr Val Leu Pro Pro Ser
            340                 345                 350

Pro Lys Glu Leu Ser Ser Ser Asp Thr Val Ser Ile Thr Cys Leu Ile
        355                 360                 365

Lys Asp Phe Tyr Pro Pro Asp Ile Asp Val Glu Trp Gln Ser Asn Gly
```

-continued

```
              370               375               380
Gln Gln Glu Pro Glu Arg Lys His Arg Met Thr Pro Pro Gln Leu Asp
385               390               395               400

Glu Asp Gly Ser Tyr Phe Leu Tyr Ser Lys Leu Ser Val Asp Lys Ser
              405               410               415

Arg Trp Gln Gln Gly Asp Pro Phe Thr Cys Ala Val Met His Glu Thr
              420               425               430

Leu Gln Asn His Tyr Thr Asp Leu Ser Leu Ser His Ser Pro Gly Lys
          435               440               445
```

```
<210> SEQ ID NO 43
<211> LENGTH: 453
<212> TYPE: PRT
<213> ORGANISM: Artificial Sequence
<220> FEATURE:
<223> OTHER INFORMATION: Synthetic: Exemplary caninized, matured
      variable heavy chain sequence cmVH3 and canine IgG-B

<400> SEQUENCE: 43
```

```
Glu Val Gln Leu Val Glu Ser Gly Pro Ser Leu Val Lys Pro Gly Gly
1               5                 10                15

Ser Leu Arg Leu Thr Cys Ser Val Thr Gly Asp Ser Ile Thr Ser Gly
              20                25                30

Tyr Trp Lys Trp Ile Arg Lys Phe Pro Gly Asn Lys Leu Glu Tyr Met
          35                40                45

Gly Tyr Ile Ser Tyr Ser Gly Ile Thr Asp Tyr Asn Pro Ser Leu Lys
      50                55                60

Ser Arg Ile Thr Ile Ser Arg Asp Thr Ser Lys Asn Gln Tyr Tyr Leu
65                70                75                80

Gln Leu Asn Ser Val Thr Thr Glu Asp Thr Ala Thr Tyr Tyr Cys Ala
              85                90                95

Arg Tyr Ala Asn Tyr Gly Tyr Ala Met Asp Tyr Trp Gly Gln Gly Thr
              100               105               110

Ser Val Thr Val Ser Ser Ala Ser Thr Thr Ala Pro Ser Val Phe Pro
          115               120               125

Leu Ala Pro Ser Cys Gly Ser Thr Ser Gly Ser Thr Val Ala Leu Ala
          130               135               140

Cys Leu Val Ser Gly Tyr Phe Pro Glu Pro Val Thr Val Ser Trp Asn
145               150               155               160

Ser Gly Ser Leu Thr Ser Gly Val His Thr Phe Pro Ser Val Leu Gln
              165               170               175

Ser Ser Gly Leu Tyr Ser Leu Ser Ser Met Val Thr Val Pro Ser Ser
              180               185               190

Arg Trp Pro Ser Glu Thr Phe Thr Cys Asn Val Ala His Pro Ala Ser
          195               200               205

Lys Thr Lys Val Asp Lys Pro Val Pro Lys Arg Glu Asn Gly Arg Val
      210               215               220

Pro Arg Pro Pro Asp Cys Pro Lys Cys Pro Ala Pro Glu Met Leu Gly
225               230               235               240

Gly Pro Ser Val Phe Ile Phe Pro Pro Lys Pro Lys Asp Thr Leu Leu
              245               250               255

Ile Ala Arg Thr Pro Glu Val Thr Cys Val Val Val Asp Leu Asp Pro
              260               265               270

Glu Asp Pro Glu Val Gln Ile Ser Trp Phe Val Asp Gly Lys Gln Met
          275               280               285
```

-continued

```
Gln Thr Ala Lys Thr Gln Pro Arg Glu Glu Gln Phe Asn Gly Thr Tyr
    290                 295                 300

Arg Val Val Ser Val Leu Pro Ile Gly His Gln Asp Trp Leu Lys Gly
305                 310                 315                 320

Lys Gln Phe Thr Cys Lys Val Asn Asn Lys Ala Leu Pro Ser Pro Ile
                325                 330                 335

Glu Arg Thr Ile Ser Lys Ala Arg Gly Gln Ala His Gln Pro Ser Val
                340                 345                 350

Tyr Val Leu Pro Pro Ser Arg Glu Glu Leu Ser Lys Asn Thr Val Ser
            355                 360                 365

Leu Thr Cys Leu Ile Lys Asp Phe Phe Pro Pro Asp Ile Asp Val Glu
    370                 375                 380

Trp Gln Ser Asn Gly Gln Gln Glu Pro Glu Ser Lys Tyr Arg Thr Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Arg Gly Asp Thr Phe Ile Cys Ala
                420                 425                 430

Val Met His Glu Ala Leu His Asn His Tyr Thr Gln Glu Ser Leu Ser
    435                 440                 445

His Ser Pro Gly Lys
    450
```

```
<210> SEQ ID NO 44
<211> LENGTH: 451
<212> TYPE: PRT
<213> ORGANISM: Artificial Sequence
<220> FEATURE:
<223> OTHER INFORMATION: Synthetic: Exemplary caninized, matured
      variable heavy chain sequence cmVH3 and canine IgG-C

<400> SEQUENCE: 44
```

```
Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Lys Trp Ile Arg Lys Phe Pro Gly Asn Lys Leu Glu Tyr Met
            35                  40                  45

Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Ala Asn Tyr Gly Tyr Ala Met Asp Tyr Trp Gly Gln Gly Thr
                100                 105                 110

Ser Val Thr Val Ser Ser Ala Ser Thr Thr Ala Pro Ser Val Phe Pro
            115                 120                 125

Leu Ala Pro Ser Cys Gly Ser Gln Ser Gly Ser Thr Val Ala Leu Ala
    130                 135                 140

Cys Leu Val Ser Gly Tyr Ile Pro Glu Pro Val Thr Val Ser Trp Asn
145                 150                 155                 160

Ser Val Ser Leu Thr Ser Gly Val His Thr Phe Pro Ser Val Leu Gln
            165                 170                 175

Ser Ser Gly Leu Tyr Ser Leu Ser Ser Met Val Thr Val Pro Ser Ser
            180                 185                 190
```

```
Arg Trp Pro Ser Glu Thr Phe Thr Cys Asn Val Ala His Pro Ala Thr
        195                 200                 205

Asn Thr Lys Val Asp Lys Pro Val Ala Lys Glu Cys Glu Cys Lys Cys
    210                 215                 220

Asn Cys Asn Asn Cys Pro Cys Pro Gly Cys Gly Leu Leu Gly Gly Pro
225                 230                 235                 240

Ser Val Phe Ile Phe Pro Pro Lys Pro Lys Asp Ile Leu Val Thr Ala
            245                 250                 255

Arg Thr Pro Thr Val Thr Cys Val Val Val Asp Leu Asp Pro Glu Asn
        260                 265                 270

Pro Glu Val Gln Ile Ser Trp Phe Val Asp Ser Lys Gln Val Gln Thr
        275                 280                 285

Ala Asn Thr Gln Pro Arg Glu Glu Gln Ser Asn Gly Thr Tyr Arg Val
    290                 295                 300

Val Ser Val Leu Pro Ile Gly His Gln Asp Trp Leu Ser Gly Lys Gln
305                 310                 315                 320

Phe Lys Cys Lys Val Asn Asn Lys Ala Leu Pro Ser Pro Ile Glu Glu
            325                 330                 335

Ile Ile Ser Lys Thr Pro Gly Gln Ala His Gln Pro Asn Val Tyr Val
        340                 345                 350

Leu Pro Pro Ser Arg Asp Glu Met Ser Lys Asn Thr Val Thr Leu Thr
        355                 360                 365

Cys Leu Val Lys Asp Phe Phe Pro Pro Glu Ile Asp Val Glu Trp Gln
    370                 375                 380

Ser Asn Gly Gln Gln Glu Pro Glu Ser Lys Tyr Arg Met Thr Pro Pro
385                 390                 395                 400

Gln Leu Asp Glu Asp Gly Ser Tyr Phe Leu Tyr Ser Lys Leu Ser Val
            405                 410                 415

Asp Lys Ser Arg Trp Gln Arg Gly Asp Thr Phe Ile Cys Ala Val Met
        420                 425                 430

His Glu Ala Leu His Asn His Tyr Thr Gln Ile Ser Leu Ser His Ser
        435                 440                 445

Pro Gly Lys
    450

<210> SEQ ID NO 45
<211> LENGTH: 449
<212> TYPE: PRT
<213> ORGANISM: Artificial Sequence
<220> FEATURE:
<223> OTHER INFORMATION: Synthetic: Exemplary caninized, matured
      variable heavy chain sequence cmVH3 and canine IgG-D

<400> SEQUENCE: 45

Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
        20                  25                  30

Tyr Trp Lys Trp Ile Arg Lys Phe Pro Gly Asn Lys Leu Glu Tyr Met
        35                  40                  45

Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
```

```
                   85                    90                    95

Arg Tyr Ala Asn Tyr Gly Tyr Ala Met Asp Tyr Trp Gly Gln Gly Thr
                100                   105                   110

Ser Val Thr Val Ser Ser Ala Ser Thr Thr Ala Pro Ser Val Phe Pro
                115                   120                   125

Leu Ala Pro Ser Cys Gly Ser Thr Ser Gly Ser Thr Val Ala Leu Ala
                130                   135                   140

Cys Leu Val Ser Gly Tyr Phe Pro Glu Pro Val Thr Val Ser Trp Asn
145                   150                   155                   160

Ser Gly Ser Leu Thr Ser Gly Val His Thr Phe Pro Ser Val Leu Gln
                165                   170                   175

Ser Ser Gly Leu Tyr Ser Leu Ser Ser Thr Val Thr Val Pro Ser Ser
                180                   185                   190

Arg Trp Pro Ser Glu Thr Phe Thr Cys Asn Val Val His Pro Ala Ser
                195                   200                   205

Asn Thr Lys Val Asp Lys Pro Val Pro Lys Glu Ser Thr Cys Lys Cys
        210                   215                   220

Ile Ser Pro Cys Pro Val Pro Glu Ser Leu Gly Gly Pro Ser Val Phe
225                   230                   235                   240

Ile Phe Pro Pro Lys Pro Lys Asp Ile Leu Arg Ile Thr Arg Thr Pro
                245                   250                   255

Glu Ile Thr Cys Val Val Leu Asp Leu Gly Arg Glu Asp Pro Glu Val
                260                   265                   270

Gln Ile Ser Trp Phe Val Asp Gly Lys Glu Val His Thr Ala Lys Thr
                275                   280                   285

Gln Pro Arg Glu Gln Gln Phe Asn Ser Thr Tyr Arg Val Val Ser Val
        290                   295                   300

Leu Pro Ile Glu His Gln Asp Trp Leu Thr Gly Lys Glu Phe Lys Cys
305                   310                   315                   320

Arg Val Asn His Ile Gly Leu Pro Ser Pro Ile Glu Arg Thr Ile Ser
                325                   330                   335

Lys Ala Arg Gly Gln Ala His Gln Pro Ser Val Tyr Val Leu Pro Pro
                340                   345                   350

Ser Pro Lys Glu Leu Ser Ser Ser Asp Thr Val Thr Leu Thr Cys Leu
        355                   360                   365

Ile Lys Asp Phe Phe Pro Pro Glu Ile Asp Val Glu Trp Gln Ser Asn
        370                   375                   380

Gly Gln Pro Glu Pro Glu Ser Lys Tyr His Thr Thr Ala Pro Gln Leu
385                   390                   395                   400

Asp Glu Asp Gly Ser Tyr Phe Leu Tyr Ser Lys Leu Ser Val Asp Lys
                405                   410                   415

Ser Arg Trp Gln Gln Gly Asp Thr Phe Thr Cys Ala Val Met His Glu
                420                   425                   430

Ala Leu Gln Asn His Tyr Thr Asp Leu Ser Leu Ser His Ser Pro Gly
        435                   440                   445

Lys
```

<210> SEQ ID NO 46
<211> LENGTH: 221
<212> TYPE: PRT
<213> ORGANISM: Artificial Sequence
<220> FEATURE:
<223> OTHER INFORMATION: Synthetic: Exemplary caninized, matured
     variable light chain sequence cmVL1 and canine light chain
     constant region

<400> SEQUENCE: 46

Asp Ile Val Met Thr Gln Ser Pro Ala Ser Leu Ser Val Ser Leu Gly
1               5                   10                  15

Gln Arg Ala Thr Ile Ser Cys Arg Ala Ser Glu Ser Val Asp Thr Tyr
                20                  25                  30

Gly Arg Ser Phe Met His Trp Tyr Gln Gln Lys Pro Gly Gln Ser Pro
                35                  40                  45

Lys Leu Leu Ile Tyr Arg Ala Ser Asn Leu Glu Ser Gly Ile Pro Ala
        50                  55                  60

Arg Phe Gly Gly Ser Gly Ser Gly Thr Asp Phe Thr Leu Thr Ile Asp
65                  70                  75                  80

Pro Val Gln Ala Asp Asp Val Ala Thr Tyr Tyr Cys Gln Gln Ser Tyr
                85                  90                  95

Glu Asp Pro Trp Thr Phe Gly Gly Gly Thr Lys Leu Glu Ile Lys Arg
                100                 105                 110

Asn Asp Ala Gln Pro Ala Val Tyr Leu Phe Gln Pro Ser Pro Asp Gln
        115                 120                 125

Leu His Thr Gly Ser Ala Ser Val Val Cys Leu Leu Asn Ser Phe Tyr
        130                 135                 140

Pro Lys Asp Ile Asn Val Lys Trp Lys Val Asp Gly Val Ile Gln Asp
145                 150                 155                 160

Thr Gly Ile Gln Glu Ser Val Thr Glu Gln Asp Lys Asp Ser Thr Tyr
                165                 170                 175

Ser Leu Ser Ser Thr Leu Thr Met Ser Ser Thr Glu Tyr Leu Ser His
                180                 185                 190

Glu Leu Tyr Ser Cys Glu Ile Thr His Lys Ser Leu Pro Ser Thr Leu
        195                 200                 205

Ile Lys Ser Phe Gln Arg Ser Glu Cys Gln Arg Val Asp
        210                 215                 220

<210> SEQ ID NO 47
<211> LENGTH: 221
<212> TYPE: PRT
<213> ORGANISM: Artificial Sequence
<220> FEATURE:
<223> OTHER INFORMATION: Synthetic: Exemplary caninized, matured
      variable light chain sequence cmVL1 and canine light chain
      constant region

<400> SEQUENCE: 47

Asp Ile Val Met Thr Gln Ser Pro Ala Ser Leu Ser Val Ser Leu Gly
1               5                   10                  15

Gln Arg Ala Thr Ile Ser Cys Arg Ala Ser Glu Ser Val Asp Thr Tyr
                20                  25                  30

Gly Arg Ser Phe Met His Trp Tyr Gln Gln Lys Pro Gly Gln Ser Pro
                35                  40                  45

Lys Leu Leu Ile Tyr Arg Ala Ser Asn Leu Glu Ser Gly Ile Pro Ala
        50                  55                  60

Arg Phe Gly Gly Ser Gly Ser Gly Thr Asp Phe Thr Leu Thr Ile Asp
65                  70                  75                  80

Pro Val Gln Ala Asp Asp Val Ala Thr Tyr Tyr Cys Tyr Gln Ser Tyr
                85                  90                  95

Glu Asp Pro Trp Thr Phe Gly Gly Gly Thr Lys Leu Glu Ile Lys Arg
                100                 105                 110

Asn Asp Ala Gln Pro Ala Val Tyr Leu Phe Gln Pro Ser Pro Asp Gln

-continued

```
         115              120              125

Leu His Thr Gly Ser Ala Ser Val Val Cys Leu Leu Asn Ser Phe Tyr
    130              135              140

Pro Lys Asp Ile Asn Val Lys Trp Lys Val Asp Gly Val Ile Gln Asp
145              150              155              160

Thr Gly Ile Gln Glu Ser Val Thr Glu Gln Asp Lys Asp Ser Thr Tyr
                 165              170              175

Ser Leu Ser Ser Thr Leu Thr Met Ser Ser Thr Glu Tyr Leu Ser His
                 180              185              190

Glu Leu Tyr Ser Cys Glu Ile Thr His Lys Ser Leu Pro Ser Thr Leu
                 195              200              205

Ile Lys Ser Phe Gln Arg Ser Glu Cys Gln Arg Val Asp
    210              215              220

<210> SEQ ID NO 48
<211> LENGTH: 221
<212> TYPE: PRT
<213> ORGANISM: Artificial Sequence
<220> FEATURE:
<223> OTHER INFORMATION: Synthetic: Exemplary caninized, matured
      variable light chain sequence cmVL1 and canine light chain
      constant region

<400> SEQUENCE: 48

Asp Ile Val Met Thr Gln Ser Pro Ala Ser Leu Ser Val Ser Leu Gly
1               5               10              15

Gln Arg Ala Thr Ile Ser Cys Arg Ala Ser Glu Ser Val Asp Thr Tyr
                20              25              30

Gly Arg Ser Phe Met His Trp Tyr Gln Gln Lys Pro Gly Gln Ser Pro
                35              40              45

Lys Leu Leu Ile Tyr Arg Ala Ser Asn Leu Glu Ser Gly Ile Pro Ala
    50              55              60

Arg Phe Gly Gly Ser Gly Ser Gly Thr Asp Phe Thr Leu Thr Ile Asp
65              70              75              80

Pro Val Gln Ala Asp Asp Val Ala Thr Tyr Tyr Cys His Gln Ser Tyr
                85              90              95

Glu Asp Pro Trp Thr Phe Gly Gly Gly Thr Lys Leu Glu Ile Lys Arg
                100             105             110

Asn Asp Ala Gln Pro Ala Val Tyr Leu Phe Gln Pro Ser Pro Asp Gln
    115              120              125

Leu His Thr Gly Ser Ala Ser Val Val Cys Leu Leu Asn Ser Phe Tyr
    130              135              140

Pro Lys Asp Ile Asn Val Lys Trp Lys Val Asp Gly Val Ile Gln Asp
145              150              155              160

Thr Gly Ile Gln Glu Ser Val Thr Glu Gln Asp Lys Asp Ser Thr Tyr
                165              170              175

Ser Leu Ser Ser Thr Leu Thr Met Ser Ser Thr Glu Tyr Leu Ser His
                180              185              190

Glu Leu Tyr Ser Cys Glu Ile Thr His Lys Ser Leu Pro Ser Thr Leu
                195              200              205

Ile Lys Ser Phe Gln Arg Ser Glu Cys Gln Arg Val Asp
    210              215              220

<210> SEQ ID NO 49
<211> LENGTH: 118
<212> TYPE: PRT
<213> ORGANISM: Artificial Sequence
```

```
<220> FEATURE:
<223> OTHER INFORMATION: Synthetic: Exemplary felinized, matured
      variable heavy chain sequence fmVH3a  N35K G99A

<400> SEQUENCE: 49

Gln Leu Thr Leu Arg Glu Ser Gly Pro Gly Leu Val Lys Pro Ser Gln
1               5                   10                  15

Ser Leu Ser Leu Thr Cys Ser Val Thr Gly Asp Ser Ile Thr Ser Gly
            20                  25                  30

Tyr Trp Lys Trp Ile Arg Gln Arg Pro Gly Arg Gly Leu Glu Trp Leu
        35                  40                  45

Gly Tyr Ile Ser Tyr Ser Gly Ile Thr Asp Tyr Asn Pro Ser Leu Lys
    50                  55                  60

Ser Arg Ile Ser Ile Thr Ala Asp Thr Ala Gln Asn Gln Phe Ser Leu
65                  70                  75                  80

Gln Leu Ser Ser Met Thr Thr Glu Asp Thr Ala Val Tyr Tyr Cys Ala
                85                  90                  95

Arg Tyr Ala Asn Tyr Gly Tyr Ala Met Asp Tyr Trp Gly Pro Gly Ala
            100                 105                 110

Leu Val Thr Val Ser Ser
        115

<210> SEQ ID NO 50
<211> LENGTH: 118
<212> TYPE: PRT
<213> ORGANISM: Artificial Sequence
<220> FEATURE:
<223> OTHER INFORMATION: Synthetic: Exemplary felinized, matured
      variable heavy chain sequence fmVH3b  N35K G99A

<400> SEQUENCE: 50

Asp Val Gln Leu Val Glu Ser Gly Gly Asp Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Lys Trp Val Arg Gln Ala Pro Gly Lys Gly Leu Gln Trp Val
        35                  40                  45

Ala Tyr Ile Ser Tyr Ser Gly Ile Thr Asp Tyr Asn Pro Ser Leu Lys
    50                  55                  60

Ser Arg Phe Thr Ile Ser Arg Asp Asn Ala Lys Asn Thr Leu Tyr Leu
65                  70                  75                  80

Gln Met Asn Ser Leu Lys Thr Glu Asp Thr Ala Thr Tyr Tyr Cys Ala
                85                  90                  95

Arg Tyr Ala Asn Tyr Gly Tyr Ala Met Asp Tyr Trp Gly Gln Gly Ala
            100                 105                 110

Leu Val Thr Val Ser Ser
        115

<210> SEQ ID NO 51
<211> LENGTH: 118
<212> TYPE: PRT
<213> ORGANISM: Artificial Sequence
<220> FEATURE:
<223> OTHER INFORMATION: Synthetic: Exemplary felinized, matured
      variable heavy chain sequence fmVH3c  N35K G99A

<400> SEQUENCE: 51

Asp Val Gln Leu Val Glu Ser Gly Gly Asp Leu Val Lys Pro Gly Gly
1               5                   10                  15
```

-continued

```
Ser Leu Arg Leu Thr Cys Ser Val Thr Gly Asp Ser Ile Thr Ser Gly
        20              25                  30

Tyr Trp Lys Trp Ile Arg Lys Phe Pro Gly Asn Lys Leu Glu Tyr Met
        35              40                  45

Gly Tyr Ile Ser Tyr Ser Gly Ile Thr Asp Tyr Asn Pro Ser Leu Lys
    50              55                  60

Ser Arg Phe Thr Ile Ser Arg Asp Asn Ala Lys Asn Thr Leu Tyr Leu
65              70                  75                  80

Gln Met Asn Ser Leu Lys Thr Glu Asp Thr Ala Thr Tyr Tyr Cys Ala
                85                  90                  95

Arg Tyr Ala Asn Tyr Gly Tyr Ala Met Asp Tyr Trp Gly Gln Gly Ala
            100                 105                 110

Leu Val Thr Val Ser Ser
            115
```

```
<210> SEQ ID NO 52
<211> LENGTH: 111
<212> TYPE: PRT
<213> ORGANISM: Artificial Sequence
<220> FEATURE:
<223> OTHER INFORMATION: Synthetic: Exemplary felinized, matured
      variable light chain sequence fmVL3a  N34R Q93H

<400> SEQUENCE: 52
```

```
Asp Ile Val Met Thr Gln Thr Pro Leu Ser Leu Ser Val Thr Pro Gly
1               5                   10                  15

Glu Pro Ala Ser Ile Ser Cys Arg Ala Ser Glu Ser Val Asp Thr Tyr
            20                  25                  30

Gly Arg Ser Phe Met His Trp Tyr Leu Gln Lys Pro Gly Gln Ser Pro
        35                  40                  45

Arg Arg Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Arg Ile Ser
65                  70                  75                  80

Arg Val Glu Ala Asp Asp Val Gly Val Tyr Tyr Cys His Gln Ser Tyr
                85                  90                  95

Glu Asp Pro Trp Thr Phe Gly Pro Gly Thr Lys Leu Glu Ile Lys
            100                 105                 110
```

```
<210> SEQ ID NO 53
<211> LENGTH: 111
<212> TYPE: PRT
<213> ORGANISM: Artificial Sequence
<220> FEATURE:
<223> OTHER INFORMATION: Synthetic: Exemplary felinized, matured
      variable light chain sequence fmVL3b  N34R Q93H

<400> SEQUENCE: 53
```

```
Asp Val Val Met Thr Gln Thr Pro Leu Ser Leu Pro Val Thr Pro Gly
1               5                   10                  15

Glu Pro Ala Ser Ile Ser Cys Arg Ala Ser Glu Ser Val Asp Thr Tyr
            20                  25                  30

Gly Arg Ser Phe Met His Trp Tyr Leu Gln Lys Pro Gly Gln Ser Pro
        35                  40                  45

Arg Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Arg Ile Ser
65                  70                  75                  80
```

-continued

```
Arg Val Glu Ala Asp Asp Val Ala Thr Tyr Tyr Cys His Gln Ser Tyr
            85              90              95

Glu Asp Pro Trp Thr Phe Gly Gln Gly Thr Lys Leu Glu Val Lys
            100             105             110

<210> SEQ ID NO 54
<211> LENGTH: 111
<212> TYPE: PRT
<213> ORGANISM: Artificial Sequence
<220> FEATURE:
<223> OTHER INFORMATION: Synthetic: Exemplary felinized, matured
      variable light chain sequence fmVL3c  N34R Q93H

<400> SEQUENCE: 54

Asp Ile Val Met Thr Gln Thr Pro Leu Ser Leu Ser Val Thr Pro Gly
1               5               10              15

Glu Pro Ala Ser Ile Ser Cys Arg Ala Ser Glu Ser Val Asp Thr Tyr
            20              25              30

Gly Arg Ser Phe Met His Trp Tyr Gln Gln Lys Pro Gly Gln Ser Pro
        35              40              45

Lys Leu Leu Ile Tyr Arg Ala Ser Asn Leu Glu Ser Gly Val Pro Asp
    50              55              60

Arg Phe Ser Gly Ser Gly Ser Gly Thr Asp Phe Thr Leu Arg Ile Ser
65              70              75              80

Arg Val Glu Ala Asp Asp Val Gly Val Tyr Tyr Cys His Gln Ser Tyr
            85              90              95

Glu Asp Pro Trp Thr Phe Gly Pro Gly Thr Lys Leu Glu Ile Lys
            100             105             110

<210> SEQ ID NO 55
<211> LENGTH: 25
<212> TYPE: PRT
<213> ORGANISM: Artificial Sequence
<220> FEATURE:
<223> OTHER INFORMATION: Synthetic: Exemplary felinized, matured HCFR1

<400> SEQUENCE: 55

Gln Leu Thr Leu Arg Glu Ser Gly Pro Gly Leu Val Lys Pro Ser Gln
1               5               10              15

Ser Leu Ser Leu Thr Cys Ser Val Thr
            20              25

<210> SEQ ID NO 56
<211> LENGTH: 25
<212> TYPE: PRT
<213> ORGANISM: Artificial Sequence
<220> FEATURE:
<223> OTHER INFORMATION: Synthetic: Exemplary felinized, matured HCFR1

<400> SEQUENCE: 56

Asp Val Gln Leu Val Glu Ser Gly Gly Asp Leu Val Lys Pro Gly Gly
1               5               10              15

Ser Leu Arg Leu Thr Cys Ser Val Thr
            20              25

<210> SEQ ID NO 57
<211> LENGTH: 15
<212> TYPE: PRT
<213> ORGANISM: Artificial Sequence
<220> FEATURE:
<223> OTHER INFORMATION: Synthetic: Exemplary felinized, matured HCFR2

<400> SEQUENCE: 57
```

Lys Trp Ile Arg Gln Arg Pro Gly Arg Gly Leu Glu Trp Leu Gly
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthetic: Exemplary felinized, matured HCFR2

<400> SEQUENCE: 58

Lys Trp Val Arg Gln Ala Pro Gly Lys Gly Leu Gln Trp Val Ala
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic: Exemplary felinized, matured HCFR2

<400> SEQUENCE: 59

Lys Trp Ile Arg Lys Phe Pro Gly Asn Lys Leu Glu Tyr Met Gly
1               5                   10                  15

<210> SEQ ID NO 60
<211> LENGTH: 36
<212> TYPE: PRT
<213> ORGANISM: Artificial Sequence
<220> FEATURE:
<223> OTHER INFORMATION: Synthetic: Exemplary felinized, matured HCFR3

<400> SEQUENCE: 60

Asn Pro Ser Leu Lys Ser Arg Ile Ser Ile Thr Ala Asp Thr Ala Gln
1               5                   10                  15

Asn Gln Phe Ser Leu Gln Leu Ser Ser Met Thr Thr Glu Asp Thr Ala
            20                  25                  30

Val Tyr Tyr Cys
        35

<210> SEQ ID NO 61
<211> LENGTH: 36
<212> TYPE: PRT
<213> ORGANISM: Artificial Sequence
<220> FEATURE:
<223> OTHER INFORMATION: Synthetic: Exemplary felinized, matured HCFR3

<400> SEQUENCE: 61

Asn Pro Ser Leu Lys Ser Arg Phe Thr Ile Ser Arg Asp Asn Ala Lys
1               5                   10                  15

Asn Thr Leu Tyr Leu Gln Met Asn Ser Leu Lys Thr Glu Asp Thr Ala
            20                  25                  30

Thr Tyr Tyr Cys
        35

<210> SEQ ID NO 62
<211> LENGTH: 11
<212> TYPE: PRT
<213> ORGANISM: Artificial Sequence
<220> FEATURE:
<223> OTHER INFORMATION: Synthetic: Exemplary felinized, matured HCFR4

<400> SEQUENCE: 62

Trp Gly Pro Gly Ala Leu Val Thr Val Ser Ser

-continued 1                    5                        10

<210> SEQ ID NO 63
<211> LENGTH: 11
<212> TYPE: PRT
<213> ORGANISM: Artificial Sequence
<220> FEATURE:
<223> OTHER INFORMATION: Synthetic: Exemplary felinized, matured HCFR4

<400> SEQUENCE: 63

Trp Gly Gln Gly Ala Leu Val Thr Val Ser Ser
1                    5                        10

<210> SEQ ID NO 64
<211> LENGTH: 23
<212> TYPE: PRT
<213> ORGANISM: Artificial Sequence
<220> FEATURE:
<223> OTHER INFORMATION: Synthetic: Exemplary felinized, matured LCFR1

<400> SEQUENCE: 64

Asp Ile Val Met Thr Gln Thr Pro Leu Ser Leu Ser Val Thr Pro Gly
1                    5                        10                       15

Glu Pro Ala Ser Ile Ser Cys
            20

<210> SEQ ID NO 65
<211> LENGTH: 23
<212> TYPE: PRT
<213> ORGANISM: Artificial Sequence
<220> FEATURE:
<223> OTHER INFORMATION: Synthetic: Exemplary felinized, matured LCFR1

<400> SEQUENCE: 65

Asp Val Val Met Thr Gln Thr Pro Leu Ser Leu Pro Val Thr Pro Gly
1                    5                        10                       15

Glu Pro Ala Ser Ile Ser Cys
            20

<210> SEQ ID NO 66
<211> LENGTH: 15
<212> TYPE: PRT
<213> ORGANISM: Artificial Sequence
<220> FEATURE:
<223> OTHER INFORMATION: Synthetic: Exemplary felinized, matured LCFR2

<400> SEQUENCE: 66

Trp Tyr Leu Gln Lys Pro Gly Gln Ser Pro Arg Arg Leu Ile Tyr
1                    5                        10                       15

<210> SEQ ID NO 67
<211> LENGTH: 15
<212> TYPE: PRT
<213> ORGANISM: Artificial Sequence
<220> FEATURE:
<223> OTHER INFORMATION: Synthetic: Exemplary felinized, matured LCFR2

<400> SEQUENCE: 67

Trp Tyr Leu Gln Lys Pro Gly Gln Ser Pro Arg Leu Leu Ile Tyr
1                    5                        10                       15

<210> SEQ ID NO 68
<211> LENGTH: 15
<212> TYPE: PRT
<213> ORGANISM: Artificial Sequence
<220> FEATURE:

-continued

<223> OTHER INFORMATION: Synthetic: Exemplary felinized, matured LCFR2

<400> SEQUENCE: 68

Trp Tyr Gln Gln Lys Pro Gly Gln Ser Pro Lys Leu Leu Ile Tyr
1               5                   10                  15

<210> SEQ ID NO 69
<211> LENGTH: 32
<212> TYPE: PRT
<213> ORGANISM: Artificial Sequence
<220> FEATURE:
<223> OTHER INFORMATION: Synthetic: Exemplary felinized, matured LCFR3

<400> SEQUENCE: 69

Gly Val Pro Asp Arg Phe Ser Gly Ser Gly Ser Gly Thr Asp Phe Thr
1               5                   10                  15

Leu Arg Ile Ser Arg Val Glu Ala Asp Asp Val Gly Val Tyr Tyr Cys
            20                  25                  30

<210> SEQ ID NO 70
<211> LENGTH: 32
<212> TYPE: PRT
<213> ORGANISM: Artificial Sequence
<220> FEATURE:
<223> OTHER INFORMATION: Synthetic: Exemplary felinized, matured LCFR3

<400> SEQUENCE: 70

Gly Val Pro Asp Arg Phe Ser Gly Ser Gly Ser Gly Thr Asp Phe Thr
1               5                   10                  15

Leu Arg Ile Ser Arg Val Glu Ala Asp Asp Val Ala Thr Tyr Tyr Cys
            20                  25                  30

<210> SEQ ID NO 71
<211> LENGTH: 10
<212> TYPE: PRT
<213> ORGANISM: Artificial Sequence
<220> FEATURE:
<223> OTHER INFORMATION: Synthetic: Exemplary felinized, matured LCFR4

<400> SEQUENCE: 71

Phe Gly Pro Gly Thr Lys Leu Glu Ile Lys
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic: Exemplary felinized, matured LCFR4

<400> SEQUENCE: 72

Phe Gly Gln Gly Thr Lys Leu Glu Val Lys
1               5                   10

<210> SEQ ID NO 73
<211> LENGTH: 453
<212> TYPE: PRT
<213> ORGANISM: Artificial Sequence
<220> FEATURE:
<223> OTHER INFORMATION: Synthetic: Exemplary felinized, matured
      variable heavy chain sequence fmVH3a and feline heavy chain
      constant region

<400> SEQUENCE: 73

Gln Leu Thr Leu Arg Glu Ser Gly Pro Gly Leu Val Lys Pro Ser Gln
1               5                   10                  15

```
Ser Leu Ser Leu Thr Cys Ser Val Thr Gly Asp Ser Ile Thr Ser Gly
         20              25              30

Tyr Trp Lys Trp Ile Arg Gln Arg Pro Gly Arg Gly Leu Glu Trp Leu
         35              40              45

Gly Tyr Ile Ser Tyr Ser Gly Ile Thr Asp Tyr Asn Pro Ser Leu Lys
     50              55              60

Ser Arg Ile Ser Ile Thr Ala Asp Thr Ala Gln Asn Gln Phe Ser Leu
 65              70              75              80

Gln Leu Ser Ser Met Thr Thr Glu Asp Thr Ala Val Tyr Tyr Cys Ala
             85              90              95

Arg Tyr Ala Asn Tyr Gly Tyr Ala Met Asp Tyr Trp Gly Pro Gly Ala
             100             105             110

Leu Val Thr Val Ser Ser Ala Ser Thr Thr Ala Pro Ser Val Phe Pro
         115             120             125

Leu Ala Pro Ser Cys Gly Thr Thr Ser Gly Ala Thr Val Ala Leu Ala
     130             135             140

Cys Leu Val Leu Gly Tyr Phe Pro Glu Pro Val Thr Val Ser Trp Asn
145             150             155             160

Ser Gly Ala Leu Thr Ser Gly Val His Thr Phe Pro Ala Val Leu Gln
             165             170             175

Ala Ser Gly Leu Tyr Ser Leu Ser Ser Met Val Thr Val Pro Ser Ser
             180             185             190

Arg Trp Leu Ser Asp Thr Phe Thr Cys Asn Val Ala His Pro Pro Ser
         195             200             205

Asn Thr Lys Val Asp Lys Thr Val Arg Lys Thr Asp His Pro Pro Gly
     210             215             220

Pro Lys Pro Cys Asp Cys Pro Lys Cys Pro Pro Pro Glu Met Leu Gly
225             230             235             240

Gly Pro Ser Ile Phe Ile Phe Pro Pro Lys Pro Lys Asp Thr Leu Ser
             245             250             255

Ile Ser Arg Thr Pro Glu Val Thr Cys Leu Val Val Asp Leu Gly Pro
             260             265             270

Asp Asp Ser Asp Val Gln Ile Thr Trp Phe Val Asp Asn Thr Gln Val
         275             280             285

Tyr Thr Ala Lys Thr Ser Pro Arg Glu Glu Gln Phe Asn Ser Thr Tyr
     290             295             300

Arg Val Val Ser Val Leu Pro Ile Leu His Gln Asp Trp Leu Lys Gly
305             310             315             320

Lys Glu Phe Lys Cys Lys Val Asn Ser Lys Ser Leu Pro Ser Pro Ile
             325             330             335

Glu Arg Thr Ile Ser Lys Ala Lys Gly Gln Pro His Glu Pro Gln Val
             340             345             350

Tyr Val Leu Pro Pro Ala Gln Glu Glu Leu Ser Arg Asn Lys Val Ser
         355             360             365

Val Thr Cys Leu Ile Lys Ser Phe His Pro Pro Asp Ile Ala Val Glu
     370             375             380

Trp Glu Ile Thr Gly Gln Pro Glu Pro Glu Asn Asn Tyr Arg Thr Thr
385             390             395             400

Pro Pro Gln Leu Asp Ser Asp Gly Thr Tyr Phe Val Tyr Ser Lys Leu
             405             410             415

Ser Val Asp Arg Ser His Trp Gln Arg Gly Asn Thr Tyr Thr Cys Ser
             420             425             430
```

-continued

```
Val Ser His Glu Ala Leu His Ser His His Thr Gln Lys Ser Leu Thr
    435                 440                 445

Gln Ser Pro Gly Lys
    450

<210> SEQ ID NO 74
<211> LENGTH: 453
<212> TYPE: PRT
<213> ORGANISM: Artificial Sequence
<220> FEATURE:
<223> OTHER INFORMATION: Synthetic: Exemplary felinized, matured
      variable heavy chain sequence fmVH3b and feline heavy chain
      constant region

<400> SEQUENCE: 74

Asp Val Gln Leu Val Glu Ser Gly Gly Asp Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Lys Trp Val Arg Gln Ala Pro Gly Lys Gly Leu Gln Trp Val
            35                  40                  45

Ala Tyr Ile Ser Tyr Ser Gly Ile Thr Asp Tyr Asn Pro Ser Leu Lys
    50                  55                  60

Ser Arg Phe Thr Ile Ser Arg Asp Asn Ala Lys Asn Thr Leu Tyr Leu
65                  70                  75                  80

Gln Met Asn Ser Leu Lys Thr Glu Asp Thr Ala Thr Tyr Tyr Cys Ala
                85                  90                  95

Arg Tyr Ala Asn Tyr Gly Tyr Ala Met Asp Tyr Trp Gly Gln Gly Ala
            100                 105                 110

Leu Val Thr Val Ser Ser Ala Ser Thr Thr Ala Pro Ser Val Phe Pro
            115                 120                 125

Leu Ala Pro Ser Cys Gly Thr Thr Ser Gly Ala Thr Val Ala Leu Ala
    130                 135                 140

Cys Leu Val Leu Gly Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ala Ser Gly Leu Tyr Ser Leu Ser Ser Met Val Thr Val Pro Ser Ser
            180                 185                 190

Arg Trp Leu Ser Asp Thr Phe Thr Cys Asn Val Ala His Pro Pro Ser
            195                 200                 205

Asn Thr Lys Val Asp Lys Thr Val Arg Lys Thr Asp His Pro Pro Gly
    210                 215                 220

Pro Lys Pro Cys Asp Cys Pro Lys Cys Pro Pro Pro Glu Met Leu Gly
225                 230                 235                 240

Gly Pro Ser Ile Phe Ile Phe Pro Pro Lys Pro Lys Asp Thr Leu Ser
            245                 250                 255

Ile Ser Arg Thr Pro Glu Val Thr Cys Leu Val Val Asp Leu Gly Pro
            260                 265                 270

Asp Asp Ser Asp Val Gln Ile Thr Trp Phe Val Asp Asn Thr Gln Val
            275                 280                 285

Tyr Thr Ala Lys Thr Ser Pro Arg Glu Glu Gln Phe Asn Ser Thr Tyr
    290                 295                 300

Arg Val Val Ser Val Leu Pro Ile Leu His Gln Asp Trp Leu Lys Gly
305                 310                 315                 320

Lys Glu Phe Lys Cys Lys Val Asn Ser Lys Ser Leu Pro Ser Pro Ile
```

```
                      325                 330                 335

Glu Arg Thr Ile Ser Lys Ala Lys Gly Gln Pro His Glu Pro Gln Val
            340                 345                 350

Tyr Val Leu Pro Pro Ala Gln Glu Glu Leu Ser Arg Asn Lys Val Ser
            355                 360                 365

Val Thr Cys Leu Ile Lys Ser Phe His Pro Pro Asp Ile Ala Val Glu
            370                 375                 380

Trp Glu Ile Thr Gly Gln Pro Glu Pro Glu Asn Asn Tyr Arg Thr Thr
385                 390                 395                 400

Pro Pro Gln Leu Asp Ser Asp Gly Thr Tyr Phe Val Tyr Ser Lys Leu
                405                 410                 415

Ser Val Asp Arg Ser His Trp Gln Arg Gly Asn Thr Tyr Thr Cys Ser
                420                 425                 430

Val Ser His Glu Ala Leu His Ser His His Thr Gln Lys Ser Leu Thr
                435                 440                 445

Gln Ser Pro Gly Lys
            450
```

```
<210> SEQ ID NO 75
<211> LENGTH: 453
<212> TYPE: PRT
<213> ORGANISM: Artificial Sequence
<220> FEATURE:
<223> OTHER INFORMATION: Synthetic: Exemplary felinized, matured
      variable heavy chain sequence fmVH3c and feline heavy chain
      constant region

<400> SEQUENCE: 75

Asp Val Gln Leu Val Glu Ser Gly Gly Asp Leu Val Lys Pro Gly Gly
1                 5                   10                  15

Ser Leu Arg Leu Thr Cys Ser Val Thr Gly Asp Ser Ile Thr Ser Gly
            20                  25                  30

Tyr Trp Lys Trp Ile Arg Lys Phe Pro Gly Asn Lys Leu Glu Tyr Met
            35                  40                  45

Gly Tyr Ile Ser Tyr Ser Gly Ile Thr Asp Tyr Asn Pro Ser Leu Lys
        50                  55                  60

Ser Arg Phe Thr Ile Ser Arg Asp Asn Ala Lys Asn Thr Leu Tyr Leu
65                  70                  75                  80

Gln Met Asn Ser Leu Lys Thr Glu Asp Thr Ala Thr Tyr Tyr Cys Ala
                85                  90                  95

Arg Tyr Ala Asn Tyr Gly Tyr Ala Met Asp Tyr Trp Gly Gln Gly Ala
            100                 105                 110

Leu Val Thr Val Ser Ser Ala Ser Thr Thr Ala Pro Ser Val Phe Pro
            115                 120                 125

Leu Ala Pro Ser Cys Gly Thr Thr Ser Gly Ala Thr Val Ala Leu Ala
        130                 135                 140

Cys Leu Val Leu Gly Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ala Ser Gly Leu Tyr Ser Leu Ser Ser Met Val Thr Val Pro Ser Ser
            180                 185                 190

Arg Trp Leu Ser Asp Thr Phe Thr Cys Asn Val Ala His Pro Pro Ser
            195                 200                 205

Asn Thr Lys Val Asp Lys Thr Val Arg Lys Thr Asp His Pro Pro Gly
        210                 215                 220
```

-continued

```
Pro Lys Pro Cys Asp Cys Pro Lys Cys Pro Pro Pro Glu Met Leu Gly
225             230             Lys Cys Pro     235         Met Leu 240

Gly Pro Ser Ile Phe Ile Phe Pro Pro Lys Pro Lys Asp Thr Leu Ser
            245             250             Asp Thr 255

Ile Ser Arg Thr Pro Glu Val Thr Cys Leu Val Val Asp Leu Gly Pro
            260             265             Asp Leu 270

Asp Asp Ser Asp Val Gln Ile Thr Trp Phe Val Asp Asn Thr Gln Val
        275             280             Asn Thr 285

Tyr Thr Ala Lys Thr Ser Pro Arg Glu Glu Gln Phe Asn Ser Thr Tyr
    290             295             Phe Asn 300

Arg Val Val Ser Val Leu Pro Ile Leu His Gln Asp Trp Leu Lys Gly
305             310             His Gln 315             320

Lys Glu Phe Lys Cys Lys Val Asn Ser Lys Ser Leu Pro Ser Pro Ile
            325             330             Ser Pro 335

Glu Arg Thr Ile Ser Lys Ala Lys Gly Gln Pro His Glu Pro Gln Val
            340             345             Glu Pro 350

Tyr Val Leu Pro Pro Ala Gln Glu Glu Leu Ser Arg Asn Lys Val Ser
            355             360             Asn Lys 365

Val Thr Cys Leu Ile Lys Ser Phe His Pro Pro Asp Ile Ala Val Glu
            370             375             Ile Ala 380

Trp Glu Ile Thr Gly Gln Pro Glu Pro Glu Asn Asn Tyr Arg Thr Thr
385             390             Asn Asn 395             400

Pro Pro Gln Leu Asp Ser Asp Gly Thr Tyr Phe Val Tyr Ser Lys Leu
            405             410             Tyr Ser 415

Ser Val Asp Arg Ser His Trp Gln Arg Gly Asn Thr Tyr Thr Cys Ser
            420             425             Thr Cys 430

Val Ser His Glu Ala Leu His Ser His His Thr Gln Lys Ser Leu Thr
            435             440             Lys Ser 445

Gln Ser Pro Gly Lys
    450
```

```
<210> SEQ ID NO 76
<211> LENGTH: 221
<212> TYPE: PRT
<213> ORGANISM: Artificial Sequence
<220> FEATURE:
<223> OTHER INFORMATION: Synthetic: Exemplary felinized, matured
      variable light chain sequence fmVL3a and feline light chain
      constant region

<400> SEQUENCE: 76
```

```
Asp Ile Val Met Thr Gln Thr Pro Leu Ser Leu Ser Val Thr Pro Gly
1               5               10              15

Glu Pro Ala Ser Ile Ser Cys Arg Ala Ser Glu Ser Val Asp Thr Tyr
            20              25              30

Gly Arg Ser Phe Met His Trp Tyr Leu Gln Lys Pro Gly Gln Ser Pro
            35              40              45

Arg Arg Leu Ile Tyr Arg Ala Ser Asn Leu Glu Ser Gly Val Pro Asp
    50              55              60

Arg Phe Ser Gly Ser Gly Ser Gly Thr Asp Phe Thr Leu Arg Ile Ser
65              70              75              80

Arg Val Glu Ala Asp Asp Val Gly Val Tyr Tyr Cys His Gln Ser Tyr
            85              90              95

Glu Asp Pro Trp Thr Phe Gly Pro Gly Thr Lys Leu Glu Ile Lys Arg
            100             105             110
```

-continued

```
Ser Asp Ala Gln Pro Ser Val Phe Leu Phe Gln Pro Ser Leu Asp Glu
        115                 120                 125

Leu His Thr Gly Ser Ala Ser Ile Val Cys Ile Leu Asn Asp Phe Tyr
        130                 135                 140

Pro Lys Glu Val Asn Val Lys Trp Lys Val Asp Gly Val Val Gln Asn
145                 150                 155                 160

Lys Gly Ile Gln Glu Ser Thr Thr Glu Gln Asn Ser Lys Asp Ser Thr
                165                 170                 175

Tyr Ser Leu Ser Ser Thr Leu Thr Met Ser Ser Thr Glu Tyr Gln Ser
                180                 185                 190

His Glu Lys Phe Ser Cys Glu Val Thr His Lys Ser Leu Ala Ser Thr
                195                 200                 205

Leu Val Lys Ser Phe Asn Arg Ser Glu Cys Gln Arg Glu
        210                 215                 220
```

```
<210> SEQ ID NO 77
<211> LENGTH: 221
<212> TYPE: PRT
<213> ORGANISM: Artificial Sequence
<220> FEATURE:
<223> OTHER INFORMATION: Synthetic: Exemplary felinized, matured
      variable light chain sequence fmVL3b and feline light chain
      constant region

<400> SEQUENCE: 77
```

```
Asp Val Val Met Thr Gln Thr Pro Leu Ser Leu Pro Val Thr Pro Gly
1               5                   10                  15

Glu Pro Ala Ser Ile Ser Cys Arg Ala Ser Glu Ser Val Asp Thr Tyr
                20                  25                  30

Gly Arg Ser Phe Met His Trp Tyr Leu Gln Lys Pro Gly Gln Ser Pro
            35                  40                  45

Arg Leu Leu Ile Tyr Arg Ala Ser Asn Leu Glu Ser Gly Val Pro Asp
        50                  55                  60

Arg Phe Ser Gly Ser Gly Ser Gly Thr Asp Phe Thr Leu Arg Ile Ser
65                  70                  75                  80

Arg Val Glu Ala Asp Asp Val Ala Thr Tyr Tyr Cys His Gln Ser Tyr
                85                  90                  95

Glu Asp Pro Trp Thr Phe Gly Gln Gly Thr Lys Leu Glu Val Lys Arg
            100                 105                 110

Ser Asp Ala Gln Pro Ser Val Phe Leu Phe Gln Pro Ser Leu Asp Glu
        115                 120                 125

Leu His Thr Gly Ser Ala Ser Ile Val Cys Ile Leu Asn Asp Phe Tyr
        130                 135                 140

Pro Lys Glu Val Asn Val Lys Trp Lys Val Asp Gly Val Val Gln Asn
145                 150                 155                 160

Lys Gly Ile Gln Glu Ser Thr Thr Glu Gln Asn Ser Lys Asp Ser Thr
                165                 170                 175

Tyr Ser Leu Ser Ser Thr Leu Thr Met Ser Ser Thr Glu Tyr Gln Ser
                180                 185                 190

His Glu Lys Phe Ser Cys Glu Val Thr His Lys Ser Leu Ala Ser Thr
                195                 200                 205

Leu Val Lys Ser Phe Asn Arg Ser Glu Cys Gln Arg Glu
        210                 215                 220
```

```
<210> SEQ ID NO 78
<211> LENGTH: 221
<212> TYPE: PRT
```

-continued

```
<213> ORGANISM: Artificial Sequence
<220> FEATURE:
<223> OTHER INFORMATION: Synthetic: Exemplary felinized, matured
      variable light chain sequence fmVL3c and feline light chain
      constant region

<400> SEQUENCE: 78

Asp Ile Val Met Thr Gln Thr Pro Leu Ser Leu Ser Val Thr Pro Gly
1               5                   10                  15

Glu Pro Ala Ser Ile Ser Cys Arg Ala Ser Glu Ser Val Asp Thr Tyr
            20                  25                  30

Gly Arg Ser Phe Met His Trp Tyr Gln Gln Lys Pro Gly Gln Ser Pro
            35                  40                  45

Lys Leu Leu Ile Tyr Arg Ala Ser Asn Leu Glu Ser Gly Val Pro Asp
        50                  55                  60

Arg Phe Ser Gly Ser Gly Ser Gly Thr Asp Phe Thr Leu Arg Ile Ser
65                  70                  75                  80

Arg Val Glu Ala Asp Asp Val Gly Val Tyr Tyr Cys His Gln Ser Tyr
                85                  90                  95

Glu Asp Pro Trp Thr Phe Gly Pro Gly Thr Lys Leu Glu Ile Lys Arg
            100                 105                 110

Ser Asp Ala Gln Pro Ser Val Phe Leu Phe Gln Pro Ser Leu Asp Glu
            115                 120                 125

Leu His Thr Gly Ser Ala Ser Ile Val Cys Ile Leu Asn Asp Phe Tyr
        130                 135                 140

Pro Lys Glu Val Asn Val Lys Trp Lys Val Asp Gly Val Val Gln Asn
145                 150                 155                 160

Lys Gly Ile Gln Glu Ser Thr Thr Glu Gln Asn Ser Lys Asp Ser Thr
                165                 170                 175

Tyr Ser Leu Ser Ser Thr Leu Thr Met Ser Ser Thr Glu Tyr Gln Ser
            180                 185                 190

His Glu Lys Phe Ser Cys Glu Val Thr His Lys Ser Leu Ala Ser Thr
            195                 200                 205

Leu Val Lys Ser Phe Asn Arg Ser Glu Cys Gln Arg Glu
    210                 215                 220

<210> SEQ ID NO 79
<211> LENGTH: 159
<212> TYPE: PRT
<213> ORGANISM: Canis lupus familiaris
<220> FEATURE:
<221> NAME/KEY: misc_feature
<222> LOCATION: (1)..(159)
<223> OTHER INFORMATION: Canine IL31 amino acid sequence

<400> SEQUENCE: 79

Met Leu Ser His Thr Gly Pro Ser Arg Phe Ala Leu Phe Leu Leu Cys
1               5                   10                  15

Ser Met Glu Thr Leu Leu Ser Ser His Met Ala Pro Thr His Gln Leu
            20                  25                  30

Pro Pro Ser Asp Val Arg Lys Ile Ile Leu Glu Leu Gln Pro Leu Ser
            35                  40                  45

Arg Gly Leu Leu Glu Asp Tyr Gln Lys Lys Glu Thr Gly Val Pro Glu
        50                  55                  60

Ser Asn Arg Thr Leu Leu Leu Cys Leu Thr Ser Asp Ser Gln Pro Pro
65                  70                  75                  80

Arg Leu Asn Ser Ser Ala Ile Leu Pro Tyr Phe Arg Ala Ile Arg Pro
                85                  90                  95
```

```
Leu Ser Asp Lys Asn Ile Ile Asp Lys Ile Ile Glu Gln Leu Asp Lys
          100             105             110

Leu Lys Phe Gln His Glu Pro Glu Thr Glu Ile Ser Val Pro Ala Asp
          115             120             125

Thr Phe Glu Cys Lys Ser Phe Ile Leu Thr Ile Leu Gln Gln Phe Ser
     130             135             140

Ala Cys Leu Glu Ser Val Phe Lys Ser Leu Asn Ser Gly Pro Gln
145             150             155

<210> SEQ ID NO 80
<211> LENGTH: 137
<212> TYPE: PRT
<213> ORGANISM: Canis lupus familiaris
<220> FEATURE:
<221> NAME/KEY: misc_feature
<222> LOCATION: (1)..(137)
<223> OTHER INFORMATION: Mature canine IL31 amino acid sequence

<400> SEQUENCE: 80

Ser Ser His Met Ala Pro Thr His Gln Leu Pro Pro Ser Asp Val Arg
1               5              10              15

Lys Ile Ile Leu Glu Leu Gln Pro Leu Ser Arg Gly Leu Leu Glu Asp
          20              25              30

Tyr Gln Lys Lys Glu Thr Gly Val Pro Glu Ser Asn Arg Thr Leu Leu
          35              40              45

Leu Cys Leu Thr Ser Asp Ser Gln Pro Pro Arg Leu Asn Ser Ser Ala
     50              55              60

Ile Leu Pro Tyr Phe Arg Ala Ile Arg Pro Leu Ser Asp Lys Asn Ile
65              70              75              80

Ile Asp Lys Ile Ile Glu Gln Leu Asp Lys Leu Lys Phe Gln His Glu
          85              90              95

Pro Glu Thr Glu Ile Ser Val Pro Ala Asp Thr Phe Glu Cys Lys Ser
          100             105             110

Phe Ile Leu Thr Ile Leu Gln Gln Phe Ser Ala Cys Leu Glu Ser Val
          115             120             125

Phe Lys Ser Leu Asn Ser Gly Pro Gln
     130             135

<210> SEQ ID NO 81
<211> LENGTH: 159
<212> TYPE: PRT
<213> ORGANISM: Felis catus
<220> FEATURE:
<221> NAME/KEY: misc_feature
<222> LOCATION: (1)..(159)
<223> OTHER INFORMATION: Feline IL31 amino acid sequence

<400> SEQUENCE: 81

Met Leu Ser His Ala Gly Pro Ala Arg Phe Ala Leu Phe Leu Leu Cys
1               5              10              15

Cys Met Glu Thr Leu Leu Pro Ser His Met Ala Pro Ala His Arg Leu
          20              25              30

Gln Pro Ser Asp Val Arg Lys Ile Ile Leu Glu Leu Arg Pro Met Ser
          35              40              45

Lys Gly Leu Leu Gln Asp Tyr Leu Lys Lys Glu Ile Gly Leu Pro Glu
     50              55              60

Ser Asn His Ser Ser Leu Pro Cys Leu Ser Ser Asp Ser Gln Leu Pro
65              70              75              80
```

```
His Ile Asn Gly Ser Ala Ile Leu Pro Tyr Phe Arg Ala Ile Arg Pro
                85              90              95

Leu Ser Asp Lys Asn Thr Ile Asp Lys Ile Ile Glu Gln Leu Asp Lys
            100             105             110

Leu Lys Phe Gln Arg Glu Pro Glu Ala Lys Val Ser Met Pro Ala Asp
        115             120             125

Asn Phe Glu Arg Lys Asn Phe Ile Leu Ala Val Leu Gln Gln Phe Ser
    130             135             140

Ala Cys Leu Glu His Val Leu Gln Ser Leu Asn Ser Gly Pro Gln
145             150             155
```

```
<210> SEQ ID NO 82
<211> LENGTH: 163
<212> TYPE: PRT
<213> ORGANISM: Mus musculus
<220> FEATURE:
<221> NAME/KEY: misc_feature
<222> LOCATION: (1)..(163)
<223> OTHER INFORMATION: Murine IL31 precursor amino acid sequence

<400> SEQUENCE: 82
```

```
Met Ile Phe His Thr Gly Thr Thr Lys Pro Thr Leu Val Leu Leu Cys
1               5               10              15

Cys Ile Gly Thr Trp Leu Ala Thr Cys Ser Leu Ser Phe Gly Ala Pro
            20              25              30

Ile Ser Lys Glu Asp Leu Arg Thr Thr Ile Asp Leu Leu Lys Gln Glu
        35              40              45

Ser Gln Asp Leu Tyr Asn Asn Tyr Ser Ile Lys Gln Ala Ser Gly Met
    50              55              60

Ser Ala Asp Glu Ser Ile Gln Leu Pro Cys Phe Ser Leu Asp Arg Glu
65              70              75              80

Ala Leu Thr Asn Ile Ser Val Ile Ile Ala His Leu Glu Lys Val Lys
                85              90              95

Val Leu Ser Glu Asn Thr Val Asp Thr Ser Trp Val Ile Arg Trp Leu
            100             105             110

Thr Asn Ile Ser Cys Phe Asn Pro Leu Asn Leu Asn Ile Ser Val Pro
        115             120             125

Gly Asn Thr Asp Glu Ser Tyr Asp Cys Lys Val Phe Val Leu Thr Val
    130             135             140

Leu Lys Gln Phe Ser Asn Cys Met Ala Glu Leu Gln Ala Lys Asp Asn
145             150             155             160

Thr Thr Cys
```

```
<210> SEQ ID NO 83
<211> LENGTH: 330
<212> TYPE: PRT
<213> ORGANISM: Artificial Sequence
<220> FEATURE:
<223> OTHER INFORMATION: Synthetic: Exemplary canine constant heavy
      chain IgG-A

<400> SEQUENCE: 83
```

```
Ala Ser Thr Thr Ala Pro Ser Val Phe Pro Leu Ala Pro Ser Cys Gly
1               5               10              15

Ser Thr Ser Gly Ser Thr Val Ala Leu Ala Cys Leu Val Ser Gly Tyr
            20              25              30

Phe Pro Glu Pro Val Thr Val Ser Trp Asn Ser Gly Ser Leu Thr Ser
        35              40              45
```

-continued

```
Gly Val His Thr Phe Pro Ser Val Leu Gln Ser Ser Gly Leu His Ser
    50                  55                  60

Leu Ser Ser Met Val Thr Val Pro Ser Ser Arg Trp Pro Ser Glu Thr
65                  70                  75                  80

Phe Thr Cys Asn Val Val His Pro Ala Ser Asn Thr Lys Val Asp Lys
                85                  90                  95

Pro Val Phe Asn Glu Cys Arg Cys Thr Asp Thr Pro Cys Pro Val Pro
                100                 105                 110

Glu Pro Leu Gly Gly Pro Ser Val Leu Ile Phe Pro Pro Lys Pro Lys
                115                 120                 125

Asp Ile Leu Arg Ile Thr Arg Thr Pro Glu Val Thr Cys Val Val Leu
    130                 135                 140

Asp Leu Gly Arg Glu Asp Pro Glu Val Gln Ile Ser Trp Phe Val Asp
145                 150                 155                 160

Gly Lys Glu Val His Thr Ala Lys Thr Gln Ser Arg Glu Gln Gln Phe
                165                 170                 175

Asn Gly Thr Tyr Arg Val Val Ser Val Leu Pro Ile Glu His Gln Asp
                180                 185                 190

Trp Leu Thr Gly Lys Glu Phe Lys Cys Arg Val Asn His Ile Asp Leu
                195                 200                 205

Pro Ser Pro Ile Glu Arg Thr Ile Ser Lys Ala Arg Gly Arg Ala His
    210                 215                 220

Lys Pro Ser Val Tyr Val Leu Pro Pro Ser Pro Lys Glu Leu Ser Ser
225                 230                 235                 240

Ser Asp Thr Val Ser Ile Thr Cys Leu Ile Lys Asp Phe Tyr Pro Pro
                245                 250                 255

Asp Ile Asp Val Glu Trp Gln Ser Asn Gly Gln Gln Glu Pro Glu Arg
                260                 265                 270

Lys His Arg Met Thr Pro Pro Gln Leu Asp Glu Asp Gly Ser Tyr Phe
                275                 280                 285

Leu Tyr Ser Lys Leu Ser Val Asp Lys Ser Arg Trp Gln Gln Gly Asp
    290                 295                 300

Pro Phe Thr Cys Ala Val Met His Glu Thr Leu Gln Asn His Tyr Thr
305                 310                 315                 320

Asp Leu Ser Leu Ser His Ser Pro Gly Lys
                325                 330
```

```
<210> SEQ ID NO 84
<211> LENGTH: 335
<212> TYPE: PRT
<213> ORGANISM: Artificial Sequence
<220> FEATURE:
<223> OTHER INFORMATION: Synthetic: Exemplary canine constant heavy
      chain IgG-B

<400> SEQUENCE: 84
```

```
Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
                20                  25                  30

Phe Pro Glu Pro Val Thr Val Ser Trp Asn Ser Gly Ser Leu Thr Ser
                35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80
```

```
Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
            115                 120                 125

Phe Pro Pro Lys Pro Lys Asp Thr Leu Leu Ile Ala Arg Thr Pro Glu
        130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
            195                 200                 205

Val Asn Asn Lys Ala Leu Pro Ser Pro Ile Glu Arg Thr Ile Ser Lys
        210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
                260                 265                 270

Gln Glu Pro Glu Ser Lys Tyr Arg Thr Thr Pro Pro Gln Leu Asp Glu
            275                 280                 285

Asp Gly Ser Tyr Phe Leu Tyr Ser Lys Leu Ser Val Asp Lys Ser Arg
        290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                325                 330                 335
```

```
<210> SEQ ID NO 85
<211> LENGTH: 333
<212> TYPE: PRT
<213> ORGANISM: Artificial Sequence
<220> FEATURE:
<223> OTHER INFORMATION: Synthetic: Exemplary canine constant heavy
      chain IgG-C

<400> SEQUENCE: 85
```

```
Ala Ser Thr Thr Ala Pro Ser Val Phe Pro Leu Ala Pro Ser Cys Gly
1               5                   10                  15

Ser Gln Ser Gly Ser Thr Val Ala Leu Ala Cys Leu Val Ser Gly Tyr
            20                  25                  30

Ile Pro Glu Pro Val Thr Val Ser Trp Asn Ser Val Ser Leu Thr Ser
            35                  40                  45

Gly Val His Thr Phe Pro Ser Val Leu Gln Ser Ser Gly Leu Tyr Ser
        50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Thr Asn Thr Lys Val Asp Lys
                85                  90                  95

Pro Val Ala Lys Glu Cys Glu Cys Lys Cys Asn Cys Asn Asn Cys Pro
```

```
                100                 105                 110

Cys Pro Gly Cys Gly Leu Leu Gly Gly Pro Ser Val Phe Ile Phe Pro
            115                 120                 125

Pro Lys Pro Lys Asp Ile Leu Val Thr Ala Arg Thr Pro Thr Val Thr
        130                 135                 140

Cys Val Val Val Asp Leu Asp Pro Glu Asn Pro Glu Val Gln Ile Ser
145                 150                 155                 160

Trp Phe Val Asp Ser Lys Gln Val Gln Thr Ala Asn Thr Gln Pro Arg
                165                 170                 175

Glu Glu Gln Ser Asn Gly Thr Tyr Arg Val Val Ser Val Leu Pro Ile
                180                 185                 190

Gly His Gln Asp Trp Leu Ser Gly Lys Gln Phe Lys Cys Lys Val Asn
            195                 200                 205

Asn Lys Ala Leu Pro Ser Pro Ile Glu Glu Ile Ile Ser Lys Thr Pro
        210                 215                 220

Gly Gln Ala His Gln Pro Asn Val Tyr Val Leu Pro Pro Ser Arg Asp
225                 230                 235                 240

Glu Met Ser Lys Asn Thr Val Thr Leu Thr Cys Leu Val Lys Asp Phe
                245                 250                 255

Phe Pro Pro Glu Ile Asp Val Glu Trp Gln Ser Asn Gly Gln Gln Glu
                260                 265                 270

Pro Glu Ser Lys Tyr Arg Met Thr Pro Pro Gln Leu Asp Glu Asp Gly
            275                 280                 285

Ser Tyr Phe Leu Tyr Ser Lys Leu Ser Val Asp Lys Ser Arg Trp Gln
        290                 295                 300

Arg Gly Asp Thr Phe Ile Cys Ala Val Met His Glu Ala Leu His Asn
305                 310                 315                 320

His Tyr Thr Gln Ile Ser Leu Ser His Ser Pro Gly Lys
            325                 330

<210> SEQ ID NO 86
<211> LENGTH: 331
<212> TYPE: PRT
<213> ORGANISM: Artificial Sequence
<220> FEATURE:
<223> OTHER INFORMATION: Synthetic: Exemplary canine constant heavy
      chain IgG-D

<400> SEQUENCE: 86

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Thr Val Thr Val Pro Ser Ser Arg Trp Pro Ser Glu Thr
65                  70                  75                  80

Phe Thr Cys Asn Val Val His Pro Ala Ser Asn Thr Lys Val Asp Lys
                85                  90                  95

Pro Val Pro Lys Glu Ser Thr Cys Lys Cys Ile Ser Pro Cys Pro Val
            100                 105                 110

Pro Glu Ser Leu Gly Gly Pro Ser Val Phe Ile Phe Pro Pro Lys Pro
        115                 120                 125
```

-continued

```
Lys Asp Ile Leu Arg Ile Thr Arg Thr Pro Glu Ile Thr Cys Val Val
    130                 135                 140

Leu Asp Leu Gly Arg Glu Asp Pro Glu Val Gln Ile Ser Trp Phe Val
145                 150                 155                 160

Asp Gly Lys Glu Val His Thr Ala Lys Thr Gln Pro Arg Glu Gln Gln
                165                 170                 175

Phe Asn Ser Thr Tyr Arg Val Val Ser Val Leu Pro Ile Glu His Gln
                180                 185                 190

Asp Trp Leu Thr Gly Lys Glu Phe Lys Cys Arg Val Asn His Ile Gly
                195                 200                 205

Leu Pro Ser Pro Ile Glu Arg Thr Ile Ser Lys Ala Arg Gly Gln Ala
    210                 215                 220

His Gln Pro Ser Val Tyr Val Leu Pro Pro Ser Pro Lys Glu Leu Ser
225                 230                 235                 240

Ser Ser Asp Thr Val Thr Leu Thr Cys Leu Ile Lys Asp Phe Phe Pro
                245                 250                 255

Pro Glu Ile Asp Val Glu Trp Gln Ser Asn Gly Gln Pro Glu Pro Glu
                260                 265                 270

Ser Lys Tyr His Thr Thr Ala Pro Gln Leu Asp Glu Asp Gly Ser Tyr
                275                 280                 285

Phe Leu Tyr Ser Lys Leu Ser Val Asp Lys Ser Arg Trp Gln Gln Gly
    290                 295                 300

Asp Thr Phe Thr Cys Ala Val Met His Glu Ala Leu Gln Asn His Tyr
305                 310                 315                 320

Thr Asp Leu Ser Leu Ser His Ser Pro Gly Lys
                325                 330
```

```
<210> SEQ ID NO 87
<211> LENGTH: 110
<212> TYPE: PRT
<213> ORGANISM: Artificial Sequence
<220> FEATURE:
<223> OTHER INFORMATION: Synthetic: Exemplary canine constant light
      chain

<400> SEQUENCE: 87

Arg Asn Asp Ala Gln Pro Ala Val Tyr Leu Phe Gln Pro Ser Pro Asp
1               5                   10                  15

Gln Leu His Thr Gly Ser Ala Ser Val Val Cys Leu Leu Asn Ser Phe
                20                  25                  30

Tyr Pro Lys Asp Ile Asn Val Lys Trp Lys Val Asp Gly Val Ile Gln
        35                  40                  45

Asp Thr Gly Ile Gln Glu Ser Val Thr Glu Gln Asp Lys Asp Ser Thr
    50                  55                  60

Tyr Ser Leu Ser Ser Thr Leu Thr Met Ser Ser Thr Glu Tyr Leu Ser
65                  70                  75                  80

His Glu Leu Tyr Ser Cys Glu Ile Thr His Lys Ser Leu Pro Ser Thr
                85                  90                  95

Leu Ile Lys Ser Phe Gln Arg Ser Glu Cys Gln Arg Val Asp
                100                 105                 110
```

```
<210> SEQ ID NO 88
<211> LENGTH: 335
<212> TYPE: PRT
<213> ORGANISM: Artificial Sequence
<220> FEATURE:
<223> OTHER INFORMATION: Synthetic: Exemplary feline constant heavy
      chain IgG
```

<400> SEQUENCE: 88

```
Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
        50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
            115                 120                 125

Phe Pro Pro Lys Pro Lys Asp Thr Leu Ser Ile Ser Arg Thr Pro Glu
        130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
            195                 200                 205

Val Asn Ser Lys Ser Leu Pro Ser Pro Ile Glu Arg Thr Ile Ser Lys
            210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
            275                 280                 285

Asp Gly Thr Tyr Phe Val Tyr Ser Lys Leu Ser Val Asp Arg Ser His
        290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335
```

<210> SEQ ID NO 89
<211> LENGTH: 110
<212> TYPE: PRT
<213> ORGANISM: Artificial Sequence
<220> FEATURE:
<223> OTHER INFORMATION: Synthetic: Exemplary feline constant light
      chain

<400> SEQUENCE: 89

```
Arg Ser Asp Ala Gln Pro Ser Val Phe Leu Phe Gln Pro Ser Leu Asp
1               5                   10                  15
```

```
Glu Leu His Thr Gly Ser Ala Ser Ile Val Cys Ile Leu Asn Asp Phe
            20                  25                  30

Tyr Pro Lys Glu Val Asn Val Lys Trp Lys Val Asp Gly Val Val Gln
            35                  40                  45

Asn Lys Gly Ile Gln Glu Ser Thr Thr Glu Gln Asn Ser Lys Asp Ser
        50                  55                  60

Thr Tyr Ser Leu Ser Ser Thr Leu Thr Met Ser Ser Thr Glu Tyr Gln
65                  70                  75                  80

Ser His Glu Lys Phe Ser Cys Glu Val Thr His Lys Ser Leu Ala Ser
                85                  90                  95

Thr Leu Val Lys Ser Phe Asn Arg Ser Glu Cys Gln Arg Glu
            100                 105                 110
```

<210> SEQ ID NO 90
<211> LENGTH: 118
<212> TYPE: PRT
<213> ORGANISM: Artificial Sequence
<220> FEATURE:
<223> OTHER INFORMATION: Synthetic: Exemplary felinized, matured
      variable heavy chain sequence fmVH2  N35K G99P

<400> SEQUENCE: 90

```
Gln Leu Thr Leu Arg Glu Ser Gly Pro Gly Leu Val Lys Pro Ser Gln
1                   5                   10                  15

Ser Leu Ser Leu Thr Cys Ser Val Thr Gly Asp Ser Ile Thr Ser Gly
                20                  25                  30

Tyr Trp Lys Trp Ile Arg Gln Arg Pro Gly Asn Lys Leu Glu Tyr Met
            35                  40                  45

Gly Tyr Ile Ser Tyr Ser Gly Ile Thr Asp Tyr Asn Pro Ala Phe Gln
        50                  55                  60

Gly Arg Ile Ser Ile Thr Ala Asp Thr Ala Gln Asn Gln Phe Ser Leu
65                  70                  75                  80

Gln Leu Ser Ser Met Thr Thr Glu Asp Thr Ala Val Tyr Tyr Cys Ala
                85                  90                  95

Arg Tyr Pro Asn Tyr Gly Tyr Ala Met Asp Tyr Trp Gly Pro Gly Thr
            100                 105                 110

Leu Val Thr Val Ser Ser
        115
```

<210> SEQ ID NO 91
<211> LENGTH: 453
<212> TYPE: PRT
<213> ORGANISM: Artificial Sequence
<220> FEATURE:
<223> OTHER INFORMATION: Synthetic: Exemplary felinized, matured
      variable heavy chain sequence fmVH2 and feline heavy chain
      constant region

<400> SEQUENCE: 91

```
Gln Leu Thr Leu Arg Glu Ser Gly Pro Gly Leu Val Lys Pro Ser Gln
1                   5                   10                  15

Ser Leu Ser Leu Thr Cys Ser Val Thr Gly Asp Ser Ile Thr Ser Gly
                20                  25                  30

Tyr Trp Lys Trp Ile Arg Gln Arg Pro Gly Asn Lys Leu Glu Tyr Met
            35                  40                  45

Gly Tyr Ile Ser Tyr Ser Gly Ile Thr Asp Tyr Asn Pro Ala Phe Gln
        50                  55                  60

Gly Arg Ile Ser Ile Thr Ala Asp Thr Ala Gln Asn Gln Phe Ser Leu
```

-continued

```
65              70              75              80

Gln Leu Ser Ser Met Thr Thr Glu Asp Thr Ala Val Tyr Tyr Cys Ala
                85              90              95

Arg Tyr Pro Asn Tyr Gly Tyr Ala Met Asp Tyr Trp Gly Pro Gly Thr
                100             105             110

Leu Val Thr Val Ser Ser Ala Ser Thr Thr Ala Pro Ser Val Phe Pro
                115             120             125

Leu Ala Pro Ser Cys Gly Thr Thr Ser Gly Ala Thr Val Ala Leu Ala
        130             135             140

Cys Leu Val Leu Gly Tyr Phe Pro Glu Pro Val Thr Val Ser Trp Asn
145             150             155             160

Ser Gly Ala Leu Thr Ser Gly Val His Thr Phe Pro Ala Val Leu Gln
                165             170             175

Ala Ser Gly Leu Tyr Ser Leu Ser Ser Met Val Thr Val Pro Ser Ser
                180             185             190

Arg Trp Leu Ser Asp Thr Phe Thr Cys Asn Val Ala His Pro Pro Ser
                195             200             205

Asn Thr Lys Val Asp Lys Thr Val Arg Lys Thr Asp His Pro Pro Gly
        210             215             220

Pro Lys Pro Cys Asp Cys Pro Lys Cys Pro Pro Pro Glu Met Leu Gly
225             230             235             240

Gly Pro Ser Ile Phe Ile Phe Pro Pro Lys Pro Lys Asp Thr Leu Tyr
                245             250             255

Ile Thr Arg Glu Pro Glu Val Thr Cys Leu Val Val Asp Leu Gly Pro
                260             265             270

Asp Asp Ser Asp Val Gln Ile Thr Trp Phe Val Asp Asn Thr Gln Val
                275             280             285

Tyr Thr Ala Lys Thr Ser Pro Arg Glu Glu Gln Phe Asn Ser Thr Tyr
        290             295             300

Arg Val Val Ser Val Leu Pro Ile Leu His Gln Asp Trp Leu Lys Gly
305             310             315             320

Lys Glu Phe Lys Cys Lys Val Asn Ser Lys Ser Leu Pro Ser Pro Ile
                325             330             335

Glu Arg Thr Ile Ser Lys Ala Lys Gly Gln Pro His Glu Pro Gln Val
                340             345             350

Tyr Val Leu Pro Pro Ala Gln Glu Glu Leu Ser Arg Asn Lys Val Ser
                355             360             365

Val Thr Cys Leu Ile Lys Ser Phe His Pro Pro Asp Ile Ala Val Glu
        370             375             380

Trp Glu Ile Thr Gly Gln Pro Glu Pro Glu Asn Asn Tyr Arg Thr Thr
385             390             395             400

Pro Pro Gln Leu Asp Ser Asp Gly Thr Tyr Phe Val Tyr Ser Lys Leu
                405             410             415

Ser Val Asp Arg Ser His Trp Gln Arg Gly Asn Thr Tyr Thr Cys Ser
                420             425             430

Val Ser His Glu Ala Leu His Ser His His Thr Gln Lys Ser Leu Thr
                435             440             445

Gln Ser Pro Gly Lys
        450
```

```
<210> SEQ ID NO 92
<211> LENGTH: 722
<212> TYPE: PRT
<213> ORGANISM: Artificial Sequence
```

<220> FEATURE:
<223> OTHER INFORMATION: Synthetic: Canine IL31Ra amino acid sequence
      with linker, flag and signal sequence

<400> SEQUENCE: 92

Met Met Trp Ala Lys Val Leu Trp Met Leu Leu Leu Cys Lys Leu
1               5                   10                  15

Ser Leu Ala Val Leu Pro Ala Lys Pro Glu Asn Ile Ser Cys Ile Phe
            20                  25                  30

Tyr Tyr Glu Glu Asn Phe Thr Cys Thr Trp Ser Pro Glu Lys Glu Ala
            35                  40                  45

Ser Tyr Thr Trp Tyr Lys Val Lys Arg Thr Tyr Ser Tyr Gly Tyr Lys
    50                  55                  60

Ser Asp Ile Cys Ser Thr Asp Asn Ser Thr Arg Gly Asn His Ala Ser
65                  70                  75                  80

Cys Ser Phe Leu Pro Pro Thr Ile Thr Asn Pro Asp Asn Tyr Thr Ile
            85                  90                  95

Gln Val Glu Ala Gln Asn Ala Asp Gly Ile Met Lys Ser Asp Ile Thr
            100                 105                 110

Tyr Trp Asn Leu Asp Ala Ile Met Lys Ile Glu Pro Pro Glu Ile Phe
            115                 120                 125

Ser Val Lys Ser Val Leu Gly Ile Lys Arg Met Leu Gln Ile Lys Trp
    130                 135                 140

Ile Arg Pro Val Leu Ala Pro His Ser Ser Thr Leu Lys Tyr Thr Leu
145                 150                 155                 160

Arg Phe Arg Thr Ile Asn Ser Ala Tyr Trp Met Glu Val Asn Phe Thr
                165                 170                 175

Lys Glu Asp Ile Asp Arg Asp Glu Thr Tyr Asn Leu Thr Glu Leu Gln
            180                 185                 190

Ala Phe Thr Glu Tyr Val Met Thr Leu Arg Cys Ala Pro Ala Glu Ser
            195                 200                 205

Met Phe Trp Ser Gly Trp Ser Gln Glu Lys Val Gly Thr Thr Glu Glu
    210                 215                 220

Glu Ala Pro Tyr Gly Leu Asp Leu Trp Arg Val Leu Lys Pro Ala Met
225                 230                 235                 240

Val Asp Gly Arg Arg Pro Val Gln Leu Met Trp Lys Lys Ala Thr Gly
                245                 250                 255

Ala Pro Val Leu Glu Lys Ala Leu Gly Tyr Asn Ile Trp Tyr Phe Pro
            260                 265                 270

Glu Asn Asn Thr Asn Leu Thr Glu Thr Val Asn Thr Thr Asn Gln Thr
            275                 280                 285

His Glu Leu Tyr Leu Gly Gly Lys Thr Tyr Trp Val Tyr Val Val Ser
    290                 295                 300

Tyr Asn Ser Leu Gly Glu Ser Pro Val Ala Thr Leu Arg Ile Pro Ala
305                 310                 315                 320

Leu Asn Glu Lys Thr Phe Gln Cys Ile Glu Ala Met Gln Ala Cys Leu
                325                 330                 335

Thr Gln Asp Gln Leu Val Val Glu Trp Gln Ser Ser Ala Pro Glu Val
            340                 345                 350

Asp Thr Trp Met Val Glu Trp Phe Pro Asp Val Asp Ser Glu Pro Ser
            355                 360                 365

Ser Phe Ser Trp Glu Ser Val Ser Gln Ala Arg Asn Trp Thr Ile Gln
    370                 375                 380

Lys Asp Glu Leu Lys Pro Leu Trp Cys Tyr Asn Ile Ser Val Tyr Pro

-continued

```
385                 390                 395                 400

Val Leu Arg Asp Arg Val Gly Gln Pro Tyr Ser Thr Gln Ala Tyr Val
            405                 410                 415

Gln Glu Gly Ile Pro Ser Ala Gly Pro Val Thr Gln Ala Asp Ser Ile
            420                 425                 430

Gly Val Lys Thr Val Thr Ile Thr Trp Lys Glu Ile Pro Lys Ser Lys
            435                 440                 445

Arg Asn Gly Phe Ile Lys Asn Tyr Thr Ile Phe Tyr Gln Ala Glu Asp
    450                 455                 460

Gly Lys Glu Phe Ser Lys Thr Val Asn Ser Asn Ile Leu Gln Tyr Arg
465                 470                 475                 480

Leu Glu Ser Leu Thr Arg Arg Thr Ser Tyr Ser Leu Gln Val Met Ala
            485                 490                 495

Ser Thr Asn Ala Gly Gly Thr Asn Gly Thr Lys Ile Asn Phe Lys Thr
            500                 505                 510

Leu Ser Ile Ser Val Leu Glu Ile Phe Phe Ile Thr Ser Leu Val Gly
            515                 520                 525

Gly Gly Phe Leu Ile Leu Ile Met Leu Thr Val Ala Tyr Gly Leu Lys
    530                 535                 540

Lys Pro Asn Lys Leu Lys His Leu Cys Trp Pro Asp Val Pro Asn Pro
545                 550                 555                 560

Ala Glu Ser Ser Ile Ala Thr Trp Arg Gly Asp Asp Phe Lys Asp Lys
            565                 570                 575

Leu Asn Leu Lys Glu Ser Asp Asp Pro Val Asn Met Glu Glu Asp Gln
            580                 585                 590

Val Leu Lys Pro Tyr Ser Ala Pro Thr Asp Phe Ile Asp Lys Leu Val
            595                 600                 605

Val Asn Phe Glu Asn Phe Leu Glu Glu Val Ser Thr Glu Glu Leu Gly
    610                 615                 620

Lys Ser Gln Glu Asn Ile Leu Lys Glu Glu Lys Asn Lys His Val Thr
625                 630                 635                 640

Ser Pro Tyr Cys Leu His His Pro Pro Ile Ser Thr Glu Ile Pro Gln
            645                 650                 655

Arg Lys Pro Gln Gln Leu Cys Ser Arg Ile Pro Glu Gly Thr Cys Ser
            660                 665                 670

Glu Thr Lys Glu Gln Leu Phe Ser Ser Val Gln Ser Leu Gly Pro Asp
            675                 680                 685

His Leu Cys Glu Glu Gly Glu Pro Asn Pro Tyr Leu Lys Asn Ser Val
    690                 695                 700

Thr Thr Arg Glu Phe Val Gly Ser Gly Ser Asp Tyr Lys Asp Asp Asp
705                 710                 715                 720

Asp Lys
```

```
<210> SEQ ID NO 93
<211> LENGTH: 808
<212> TYPE: PRT
<213> ORGANISM: Artificial Sequence
<220> FEATURE:
<223> OTHER INFORMATION: Synthetic: Feline IL31Ra amino acid sequence
      with linker, flag and signal sequence

<400> SEQUENCE: 93
```

```
Met Lys Glu Phe Ala Leu Gln Phe Ser His Ile Gly Arg Pro Pro Asn
1               5                   10                  15

Gly Val Thr Trp Ala Arg Val Leu Tyr Cys Asn Ser Phe Gln Arg Leu
```

```
                20                  25                  30

Gln Cys Thr Gly Cys Thr Pro Asn Trp Met Trp Gly Gly Gln Leu Ser
            35                  40                  45

Pro Val Arg Pro Ala Arg Thr Ser Ser Gly Tyr His Arg Glu Phe Ser
        50                  55                  60

Pro Gln Pro Ala Cys Ile Asp Leu Gly Met Met Trp Ala His Ala Leu
65                  70                  75                  80

Trp Thr Leu Leu Leu Leu Cys Lys Phe Ser Leu Ala Val Leu Pro Ala
                85                  90                  95

Lys Pro Glu Asn Ile Ser Cys Val Phe Tyr Tyr Glu Glu Asn Phe Thr
                100                 105                 110

Cys Thr Trp Ser Pro Glu Lys Glu Ala Ser Tyr Thr Trp Tyr Lys Val
            115                 120                 125

Lys Arg Thr Tyr Ser Tyr Gly Tyr Lys Ser Asp Ile Cys Pro Ser Asp
        130                 135                 140

Asn Ser Thr Arg Gly Asn His Thr Phe Cys Ser Phe Leu Pro Pro Thr
145                 150                 155                 160

Ile Thr Asn Pro Asp Asn Tyr Thr Ile Gln Val Glu Ala Gln Asn Ala
                165                 170                 175

Asp Gly Ile Ile Lys Ser Asp Ile Thr His Trp Ser Leu Asp Ala Ile
                180                 185                 190

Thr Lys Ile Glu Pro Pro Glu Ile Phe Ser Val Lys Pro Val Leu Gly
            195                 200                 205

Val Lys Arg Met Val Gln Ile Lys Trp Ile Arg Pro Val Leu Ala Pro
        210                 215                 220

Val Ser Ser Thr Leu Lys Tyr Thr Leu Arg Phe Lys Thr Val Asn Ser
225                 230                 235                 240

Ala Tyr Trp Met Glu Val Asn Phe Thr Lys Glu Asp Ile Asp Arg Asp
                245                 250                 255

Glu Thr Tyr Asn Leu Thr Gly Leu Gln Ala Phe Thr Glu Tyr Val Leu
                260                 265                 270

Ala Leu Arg Cys Ala Thr Lys Glu Ser Met Phe Trp Ser Gly Trp Ser
            275                 280                 285

Gln Glu Lys Met Gly Thr Thr Glu Glu Glu Ala Pro His Gly Leu Asp
        290                 295                 300

Leu Trp Arg Val Leu Arg Pro Ala Thr Val Asp Gly Arg Arg Leu Val
305                 310                 315                 320

Gln Leu Met Trp Lys Lys Ala Ser Gly Ala Pro Val Leu Glu Lys Ala
            325                 330                 335

Leu Gly Tyr Asn Ile Trp Tyr Phe Pro Glu Asn Ser Thr Asn Leu Thr
            340                 345                 350

Lys Thr Leu Asn Thr Thr Asn Glu Lys Leu Glu Leu Tyr Leu Gly Gly
            355                 360                 365

Lys Thr Tyr Trp Val Cys Val Val Ser Tyr Asn Ser Leu Gly Glu Ser
        370                 375                 380

Pro Val Ala Thr Leu Arg Ile Pro Ala Ile Asp Glu Lys Ser Phe Gln
385                 390                 395                 400

Cys Ile Glu Ala Met Gln Ala Cys Leu Thr Gln Asp Gln Leu Val Val
                405                 410                 415

Glu Trp Arg Ser Ser Ala Pro Glu Val Asp Thr Trp Met Val Glu Trp
            420                 425                 430

Phe Pro Asp Leu Asp Ser Glu Pro Ser Thr Phe Ser Trp Glu Ser Val
            435                 440                 445
```

-continued

```
Ser Gln Ala Thr Asn Trp Thr Ile Lys Gln Asp Glu Leu Lys Pro Phe
    450                 455                 460

Trp Cys Tyr Asn Ile Ser Val Tyr Pro Val Leu Gln Asp Arg Val Gly
465                 470                 475                 480

Lys Pro Phe Ser Ile Gln Ala Tyr Val Arg Glu Gly Ile Pro Ser Ala
                485                 490                 495

Gly Pro Val Thr Gln Val Asp Asn Ile Gly Val Lys Thr Val Thr Ile
                500                 505                 510

Thr Trp Lys Glu Ile Pro Lys Ser Gln Arg Asn Gly Phe Ile Thr Asn
                515                 520                 525

Tyr Thr Ile Phe Tyr Gln Ala Glu Asp Gly Lys Glu Phe Ser Lys Thr
    530                 535                 540

Val Asn Ser Asn Ile Leu Gln Tyr Asp Leu Glu Ser Leu Thr Arg Lys
545                 550                 555                 560

Thr Ser Tyr Ser Leu Gln Val Met Ala Ser Thr Ser Ala Gly Gly Ile
                565                 570                 575

Asn Gly Thr Thr Met Asn Phe Lys Thr Leu Ser Ile Ser Ile Leu Glu
                580                 585                 590

Ile Phe Leu Ile Ile Ser Leu Val Gly Gly Gly Leu Leu Ile Leu Ile
                595                 600                 605

Ile Leu Ser Val Ala Tyr Gly Leu Lys Lys Pro Asn Arg Leu Lys His
    610                 615                 620

Leu Cys Trp Pro Asp Val Pro Asn Pro Ala Glu Ser Ser Ile Ala Thr
625                 630                 635                 640

Trp Arg Gly Asp Asp Phe Lys Asp Lys Ile Asn Leu Lys Glu Ser Asp
                645                 650                 655

Asp Pro Val Asn Met Glu Glu Asp Arg Val Leu Lys Pro Tyr Ser Ser
                660                 665                 670

Pro Arg Asp Leu Ile Asp Lys Leu Val Val Asn Phe Glu Thr Phe Leu
                675                 680                 685

Glu Asp Val Ser Thr Glu Glu Leu Gly Lys Gly Gln Glu Asn Ile Leu
    690                 695                 700

Arg Glu Glu Lys Asn Glu Tyr Val Thr Ser Pro Tyr Arg Pro Tyr Cys
705                 710                 715                 720

Pro Pro Ile Ser Thr Glu Ile Pro Gln Arg Lys Ser Gln Gln Leu Cys
                725                 730                 735

Ser Arg Ile Pro Glu Gly Ile Cys Leu Glu Thr Thr Glu Gln Leu Leu
                740                 745                 750

Ser Ser Val Pro Asn Leu Gly Arg Asp Arg Ile Cys Glu Glu Gly Glu
                755                 760                 765

Pro Asn Pro Tyr Leu Lys Asn Ser Val Thr Thr Arg Glu Phe Leu Thr
    770                 775                 780

Ser Glu Lys Leu Pro Glu Gln Thr Lys Arg Glu Val Gly Ser Gly Ser
785                 790                 795                 800

Asp Tyr Lys Asp Asp Asp Asp Lys
                805
```